(12) United States Patent
Bedzyk et al.

(10) Patent No.: US 8,748,399 B2
(45) Date of Patent: Jun. 10, 2014

(54) ACID-CLEAVABLE LINKERS EXHIBITING ALTERED RATES OF ACID HYDROLYSIS

(71) Applicant: E I du Pont de Nemours and Company, Wilmington, DE (US)

(72) Inventors: Laura A Bedzyk, Odessa, DE (US); Stephen R Fahnestock, Wilmington, DE (US); Tanja Maria Gruber, Media, PA (US); Daniel P O'Keefe, Ridley Park, PA (US); Pierre E Rouviere, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 14/077,342

(22) Filed: Nov. 12, 2013

(65) Prior Publication Data

US 2014/0080998 A1    Mar. 20, 2014

Related U.S. Application Data

(62) Division of application No. 13/226,610, filed on Sep. 7, 2011, now Pat. No. 8,609,621.

(60) Provisional application No. 61/413,501, filed on Nov. 15, 2010.

(51) Int. Cl.
  *A61K 38/08*  (2006.01)
  *C07K 1/12*  (2006.01)
  *C12P 21/06*  (2006.01)
  *C12N 15/62*  (2006.01)

(52) U.S. Cl.
  CPC .............. *C12P 21/06* (2013.01); *C07K 2319/01* (2013.01); *C07K 1/12* (2013.01); *C07K 2319/00* (2013.01); *C07K 2319/50* (2013.01); *C12N 15/62* (2013.01)
  USPC ....................................................... 514/21.7

(58) Field of Classification Search
  None
  See application file for complete search history.

(56) References Cited

U.S. PATENT DOCUMENTS

| | | | |
|---|---|---|---|
| 5,013,653 A | 5/1991 | Huston et al. |
| 5,496,924 A | 3/1996 | Habermann et al. |
| 5,851,802 A | 12/1998 | Better et al. |
| 6,242,219 B1 | 6/2001 | Better et al. |
| 6,303,340 B1 | 10/2001 | Pollitt et al. |
| 6,500,648 B1 | 12/2002 | Better et al. |
| 6,790,942 B1 | 9/2004 | Schiavon et al. |
| 7,247,454 B2 | 7/2007 | Better et al. |
| 7,579,005 B2 | 8/2009 | Keeler et al. |
| 7,749,731 B2 | 7/2010 | Better et al. |
| 7,829,311 B2 | 11/2010 | DeCarolis et al. |
| 7,951,559 B2 | 5/2011 | Alsop et al. |
| 2007/0274931 A9 | 11/2007 | Buseman-Williams et al. |
| 2008/0206809 A1 | 8/2008 | Decarolis et al. |

OTHER PUBLICATIONS

US 5,382,513, 01/1995, Lam et al. (withdrawn)

*Primary Examiner* — Thomas Heard

(57) ABSTRACT

An acid-cleavable peptide linker comprising aspartic acid and proline residues is disclosed. The acid-cleavable peptide linker provides an altered sensitivity to acid-hydrolytic release of peptides of interest from fusion peptides of the formula PEP1-L-PEP2. The inventive linker, L, is described in various embodiments, each of which provides substantially more rapid acid-release of peptides of interest than does a single aspartic acid-proline pair. In an additional aspect, a method of increasing the stability of an acid cleavable linkage to acid hydrolysis is also provided.

41 Claims, 12 Drawing Sheets

ACID-CLEAVABLE LINKERS EXHIBITING ALTERED RATES OF ACID HYDROLYSIS

CROSS-REFERENCE TO RELATED APPLICATIONS

This application is a divisional of co-pending U.S. patent application Ser. No. 13/226,610, filed Sep. 7, 2011, which claims benefit of expired U.S. Provisional Patent Application No. 61/413,501, filed Nov. 15, 2010, both of which are incorporated by reference herein in its entirety.

FIELD OF THE INVENTION

The invention relates to the field of protein expression and purification from microbial cells. More specifically, peptide linkers having an altered sensitivity to acid hydrolysis are provided as well as methods of their use.

BACKGROUND OF THE INVENTION

The efficient production of bioactive proteins and peptides has become a hallmark of the biomedical and industrial biochemical industry. Bioactive peptides and proteins are used as curative agents in a variety of diseases such as diabetes (insulin), viral infections and leukemia (interferon), diseases of the immune system (interleukins), and red blood cell deficiencies (erythropoietin) to name a few. Additionally, large quantities of proteins and peptides are needed for various industrial applications including, for example, the pulp and paper and pulp industries, textiles, food industries, personal care and cosmetics industries, sugar refining, wastewater treatment, production of alcoholic beverages and as catalysts for the generation of new pharmaceuticals.

With the advent of the discovery and implementation of combinatorial peptide screening technologies such as bacterial display, yeast display, phage display, ribosome display, and mRNA display technology new applications for peptides having strong affinity for a target surface have been developed. In particular, peptides are being looked to as linkers in biomedical fields for the attachment of diagnostic and pharmaceutical agents to surfaces (see Grinstaff et al, U.S. Patent Application Publication No. 2003-0185870 and Linter in U.S. Pat. No. 6,620,419), as well as in the personal care industry for the attachment of benefit agents to body surfaces such as hair and skin (see commonly owned U.S. Pat. No. 7,220,405, and Janssen et al. U.S. Pat. No. 7,129,326), and in the printing industry for the attachment of pigments to print media (see commonly owned U.S. Patent Application Publication No. 2005-0054752).

In some cases commercially useful proteins and peptides may be synthetically generated or isolated from natural sources. However, these methods are often expensive, time consuming and characterized by limited production capacity. The preferred method of protein and peptide production is through the fermentation of recombinantly constructed organisms, engineered to over-express the protein or peptide of interest. Although preferable to synthesis or isolation, recombinant expression of peptides has a number of obstacles to be overcome in order to be a cost-effective means of production. For example, peptides (and in particular short peptides) produced in a cellular environment are susceptible to degradation from the action of native cellular proteases. Additionally, purification can be difficult, resulting in poor yields depending on the nature of the protein or peptide of interest.

One means to mitigate the above difficulties is the use of genetic chimera for protein and peptide expression. A chimeric protein or "fusion protein" is a polypeptide comprising at least one portion of a desired protein product fused to at least one portion comprising a peptide tag. The peptide tag may be used to assist protein folding, assist in purification, alter polypeptide solubility, protect the protein from the action of degradative enzymes, and/or assist the protein in various transport and targeting processes.

In many cases it is useful to express a protein or peptide in insoluble form, particularly when the peptide of interest is rather short, normally soluble, and/or subject to proteolytic degradation within the host cell. Production of the peptide in insoluble form both facilitates simple recovery and protects the peptide from undesirable proteolytic degradation. One means to produce the peptide in insoluble form is to recombinantly produce the peptide as part of an insoluble fusion protein by including in the fusion construct, at least one peptide tag (i.e., an inclusion body tag) that induces inclusion body formation. Typically, the fusion protein is designed to include at least one cleavable peptide linker so that the peptide of interest can be subsequently recovered from the fusion protein. The fusion protein may be designed to include a plurality of solubility tags, cleavable peptide linkers, and regions encoding the peptide of interest.

Fusion proteins comprising a peptide tag that facilitate the expression of insoluble proteins are well known in the art. Typically, the tag portion of the chimeric or fusion protein is large, increasing the likelihood that the fusion protein will be insoluble. Examples of large peptides that are typically used include, but are not limited to chloramphenicol acetyltransferase (Dykes et al., *Eur. J. Biochem.*, 174:411 (1988), β-galactosidase (Schellenberger et al., *Int. J. Peptide Protein Res.*, 41:326 (1993); Shen et al., *Proc. Nat. Acad. Sci. USA* 281: 4627 (1984); and Kempe et al., *Gene*, 39:239 (1985)), glutathione-S-transferase (Ray et al., *Bio/Technology*, 11:64 (1993) and Hancock et al. (WO94/04688)), the N-terminus of L-ribulokinase (U.S. Pat. No. 5,206,154 and Lai et al., *Antimicrob. Agents & Chemo.*, 37:1614 (1993), bacteriophage T4 gp55 protein (Gramm et al., *Bio/Technology*, 12:1017 (1994), bacterial ketosteroid isomerase protein (Kuliopulos et al., *J. Am. Chem. Soc.* 116:4599 (1994), ubiquitin (Pilon et al., *Biotechnol. Prog.*, 13:374-79 (1997), bovine prochymosin (Naught et al., *Biotechnol. Bioengineer.* 57:55-61 (1998), and bactericidal/permeability-increasing protein ("BPI"; Better, M. D. and Gavit, P D., U.S. Pat. No. 6,242,219). The art is replete with specific examples of this technology, see for example U.S. Pat. No. 6,613,548, describing fusion protein of proteinaceous tag and a soluble protein and subsequent purification from cell lysate; U.S. Pat. No. 6,037,145, teaching a tag that protects the expressed chimeric protein from a specific protease; U.S. Pat. No. 5,648,244, teaching the synthesis of a fusion protein having a tag and a cleavable linker for facile purification of the desired protein; and U.S. Pat. No. 5,215,896; U.S. Pat. No. 5,302,526; and U.S. Pat. No. 5,330, 902; and U.S. Patent Application Publication No. 2005-221444, describing fusion tags containing amino acid compositions specifically designed to increase insolubility of the chimeric protein or peptide.

Shorter solubility tags have been developed from the *Zea mays* zein protein (co-owned U.S. Pat. No. 7,732,569) the *Daucus carota* cystatin (co-owned U.S. Pat. No. 7,662,913), and an amyloid-like hypothetical protein from *Caenorhabditis elegans* (co-owned U.S. Pat. No. 7,427,656; each hereby incorporated by reference in their entirety.) The use of short inclusion body tags increases the yield of the target peptide produced within the recombinant host cell.

Aspartic acid-proline linkages can be cleaved using acid treatment. However, the conditions typically used include at least one strong acid, such as HCl or $H_2SO_4$, and may require subsequent neutralization with base and may increase the cost of peptide recovery due the amount of salt produced. Further, acid hydrolysis conditions for the intended aspartic acid-proline pair may be accompanied by undesirable hydrolysis at other sites where aspartic acid residues occur or may lead to the deamidation of glutamine or asparagine.

One problem to be solved is to provide peptide linkers that are more sensitive to acid hydrolysis when compared to a single aspartic acid-proline linkage. Increased sensitivity may permit the use of weaker acids, reduce the amount of base that may be needed for neutralization, and may help to protect the peptide of interest from unwanted hydrolysis at other locations within the peptide of interest.

Situations may occur where a peptide or protein of interest contains one or more acid labile aspartic acid-proline linkages where acid hydrolysis is not desired. As such, another problem to be solved is to provide a method to increase the stability of aspartic acid-proline linkages to acid treatment in peptides or proteins wherein acid hydrolysis is undesirable.

SUMMARY OF THE INVENTION

The stated problem has been solved though the discovery of peptide linkers characterized by increased sensitivity to acid hydrolysis when compared to a single aspartic acid-proline (i.e., DP) linkage.

In one embodiment, peptide linkers characterized by greater sensitivity to acid treatment are provided, wherein the peptide linkers comprise an amino acid sequence selected from the group consisting of:

```
A. DPDP        (SEQ ID NO: 1)
B. DPDPDP      (SEQ ID NO: 2)
C. DPDPDPDP    (SEQ ID NO: 3)
D. DPDPDPP     (SEQ ID NO: 4)
E. DPDPPDPP    (SEQ ID NO: 5)
F. DPDPPDP     (SEQ ID NO: 6),
   and
G. DPPDPPDP    (SEQ ID NO: 7),
``` wherein D is aspartic acid and P is proline.

In a further embodiment, the invention disclosed herein encompasses a fusion peptide according to the structure PEP1-L-PEP2, wherein,
 a) PEP1 and PEP2 are independently functional peptides wherein at least one is a peptide of interest ("POI"); and
 b) L is an acid-cleavable linker comprising a peptide selected from the group consisting of:

```
A. DPDP,       (SEQ ID NO: 1)
B. DPDPDP,     (SEQ ID NO: 2)
C. DPDPDPDP,   (SEQ ID NO: 3)
D. DPDPDPP,    (SEQ ID NO: 4)
E. DPDPPDPP,   (SEQ ID NO: 5)
F. DPDPPDP,    (SEQ ID NO: 6)
   and
G. DPPDPPDP,   (SEQ ID NO: 7)
``` wherein D is aspartic acid and P is proline.

The linker, L, provides for increased efficiency of acid release of a peptide from a fusion peptide comprising L. This increase may be defined as the enhancement in acid hydrolysis rate of an intact fusion peptide having a linker of the formula according to the invention when compared to the acid hydrolysis rate of the fusion peptide, PEP1-L-PEP2, having a single DP pair as the linker, L.

In this embodiment, the peptides PEP1 and PEP2 may each be a peptide of interest (i.e., "POI"). Alternatively, one of PEP1 or PEP2 may be an inclusion body tag (i.e., "IBT") whereas the remaining peptide may be a POI. In the context of the present invention an IBT is a peptide or polypeptide that directs newly synthesized fusion peptide molecules to precipitate or accumulate in insoluble inclusion bodies that can form in recombinant cells expressing heterologous, i.e., foreign, polynucleotides encoding peptides, polypeptides, fusion peptides and the like.

The POI of the fusion peptide may be virtually any peptide or polypeptide. The POI may be one of many targeting peptides that are identifiable by known biopanning methods after their expression in a recombinant bacteriophage. Such targeting peptides have high affinity for various targets of interest, including but not limited to skin, hair, nails, print media, woven or nonwoven fabric, polymers, tooth enamel, tooth pellicle, and clay and the like. POIs may also include antimicrobial peptides, pigment-binding peptides, and cellulose-binding peptides.

Such POIs may have functional applications such as diagnostic markers, pharmaceuticals, stimulators or inhibitors of enzymatic or receptor-mediated processes, and the like. Thus, the fusion peptide comprising the linker L can be employed in an isolation and purification scheme for any POI or polypeptide that can be cleaved from the fusion peptide as a result of being contacted with a sufficiently acidic environment.

In one embodiment, the invention encompasses a method of isolating a peptide of interest ("POI") from a recombinant cell expressing a heterologous fusion peptide comprising the linker L. The recombinant cell may be any prokaryotic or eukaryotic cell type, including any type of recombinant microbial cell. Preferred recombinant microbial cells include recombinant yeast cells and recombinant bacterial cells. An additional embodiment contemplates taking advantage of the fact that heterologous peptide expression in recombinant cells is often accompanied by the newly synthesized heterologous peptides accumulating in insoluble inclusion bodies within the nucleus or the cytoplasm of the cell. When such insoluble fusion peptides having a POI also comprise the acid-cleavable linker L, it is contemplated herein that acid hydrolysis of L will liberate the POI from the inclusion body, preferably converting it to a more soluble form. The released soluble form of the POI is then more easily separable from remaining inclusion bodies and insoluble remnants thereof.

However, the fusion peptide is equally suitable to embodiments wherein the chemistry of PEP1 and PEP2 result in the synthesis of a soluble fusion peptide that remains soluble in the cytoplasm and does not precipitate or form inclusion bodies. In such cases the acid cleavable linker provides a simple method to separate a soluble POI from the soluble fusion peptide or cleaved fragment thereof.

Thus, an additional embodiment of the invention comprises a method of preparing at least one peptide of interest ("POI") from a fusion peptide comprising the at least one POI, comprising:
 a) providing a recombinant cell synthesizing a fusion peptide having the structure

PEP1-L-PEP2 wherein,
i) PEP1 and PEP2 are independently functional peptides wherein at least one is a peptide of interest ("POI"); and
ii) L is an acid-cleavable linker comprising a peptide selected from the group consisting of:

```
A. DPDP,        (SEQ ID NO: 1)
B. DPDPDP,      (SEQ ID NO: 2)
C. DPDPDPDP,    (SEQ ID NO: 3)
D. DPDPDPP,     (SEQ ID NO: 4)
E. DPDPPDPP,    (SEQ ID NO: 5)
F. DPDPPDP,     (SEQ ID NO: 6)
and
G. DPPDPPDP,    (SEQ ID NO: 7)
``` wherein D is aspartic acid and P is proline; and
b) contacting the fusion peptide with a solution of sufficiently acidic pH so that linker L is cleaved, and
c) isolating the at least one POI.

In an even further embodiment, the invention encompasses a recombinant cell, preferably a microbial cell, and more preferably a bacterial cell that expresses such a fusion peptide. In this context an especially desirable bacterial cell is *E. coli*.

Situations may exist where there is a need to increase the stability of a peptide or protein comprising at least one aspartic acid-proline linkage to an acid treatment. As such, a method to increase the stability of an acid cleavable linkage to acid hydrolysis is also provided comprising:
a) providing a peptide or protein of interest comprising at least one acid cleavable linkage having the following structure:

XDP;

wherein D is aspartic acid and P is proline and X is any amino acid other than tryptophan or phenylalanine; and
b) altering said at least one acid cleavable linkage by substituting X with tryptophan or phenylalanine; whereby the stability of the acid cleavable linkage to acid hydrolysis is increased by the substitution.

BRIEF DESCRIPTION OF THE BIOLOGICAL SEQUENCES

Figure 1:
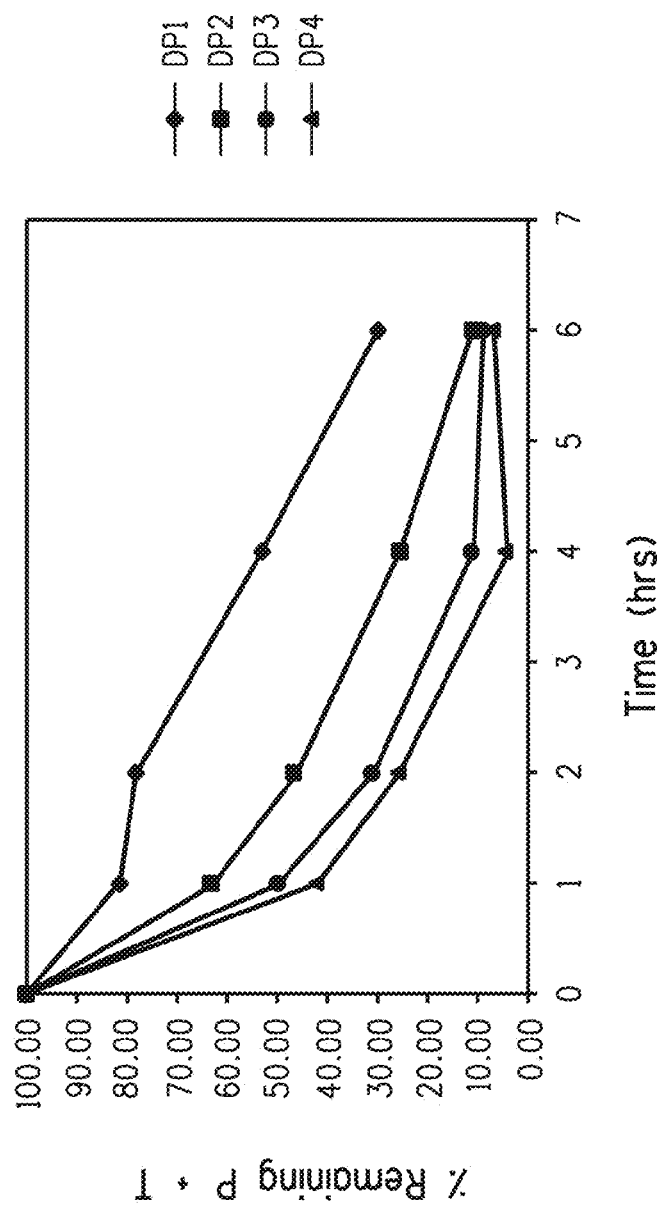
FIG. 1 shows the relative rates of acid cleavage of an intact fusion peptide having a DP cleavage site ("DP1"), a DPDP cleavage site ("DP2"; SEQ ID NO: 1), a DPDPDP cleavage site ("DP3"; SEQ ID NO: 2) or a DPDPDPDP cleavage site ("DP4"; SEQ ID NO: 3).

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the EPC and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs: 1-7 are the amino acid sequences of various embodiments of the present acid-cleavable linkers.

SEQ ID NOs: 8-25 are the polynucleotide sequences of the primers, oligonucleotides and plasmids used in preparing the polynucleotides encoding recombinant fusion peptides INK101, INK101DP, INK101DP2, INK101DP3, and INK101DP4.

SEQ ID NO: 26 is the amino acid sequence of the core acid-cleavable peptide, INK101DP.

SEQ ID NOs: 27-102 are primer sequences for performing mutagenesis of the immediately amino- and carboxy-terminal neighboring amino acids of the DP pair in INK101DP.

SEQ ID NOs: 103-110 are mutagenesis primer sequences that direct the insertion of additional proline residues into the acid-cleavable linker of INK101DP3.

SEQ ID NOs: 111-235 are amino acid sequences of various target-specific binding peptides as provided in Table 1 below:

TABLE 1

| SEQ ID NOs: | Target Specificity |
| --- | --- |
| 111-121 | Hair |
| 122-132 | Skin |
| 133-134 | Finger/toe nail |
| 135-143 | Tooth (pellicle) |
| 144-154 | Tooth (enamel) |
| 155-161 | Antimicrobial |
| 162-172 | Clay |
| 173-185 | Calcium carbonate |
| 186-192 | Polypropylene |
| 193-201 | Polytetrafluoroethylene |
| 202-208 | Polyethylene |
| 209-214 | Nylon |
| 215-217 | Polystyrene |
| 218-221 | Cellulose acetate |
| 222-225 | Carbon black |
| 226-230 | Cromophtal yellow |
| 231-235 | Sunfast magenta |

SEQ ID NOs: 236-249 are the amino acid sequences of peptides that function as inclusion body tags (IBTs).

SEQ ID NO: 250 is plasmid PLX121 that provides for expression of the INK101DP peptide.

SEQ ID NO: 251 is the sequence of the polynucleotide encoding the INK101DP peptide.

SEQ ID NO: 252 is the amino acid sequence of solubility tag KSI(C4E).

SEQ ID NO: 253 is the amino acid sequence of the peptide of interest HC353.

SEQ ID NO: 254 is the nucleic acid sequence of plasmid pLD001.

SEQ ID NO: 255 is the nucleic acid sequence encoding fusion peptide KSI(C4E).DP.HC353.

SEQ ID NO: 256 is the amino acid sequence of fusion peptide KSI(C4E).DP.HC353.

SEQ ID NO: 257 is the nucleic acid sequence of primer 353.DP3 UP.

SEQ DI NO: 258 is the nucleic acid sequence of primer 353.DP3 DOWN.

SEQ ID NO: 259 is the nucleic acid sequence encoding fusion peptide KSI(C4E).DPDPDP.HC353.

SEQ ID NO: 260 is the amino acid sequence of fusion peptide KSI(C4E).DPDPDP.HC353.

SEQ ID NO: 261 is the nucleic acid sequence of primer PP2 HC353 UP.

SEQ DI NO: 262 is the nucleic acid sequence of primer PP2 HC353 DOWN.

SEQ ID NO: 263 is the nucleic acid sequence encoding fusion peptide KSI(C4E).DPDPPDPP.HC353.

SEQ ID NO: 264 is the amino acid sequence of fusion peptide KSI(C4E).DPDPPDPP.HC353.

SEQ ID NO: 265 is the nucleic acid sequence of primer 353 PP4 UP.

SEQ ID NO: 266 is the nucleic acid sequence of primer 353 PP4 DOWN.

SEQ ID NO: 267 is the nucleic acid sequence encoding fusion peptide KSI(C4E).DPPDPPDP.HC353.

SEQ ID NO: 268 is the amino acid sequence of fusion peptide KSI(C4E).DPPDPPDP.HC353.

Several of the peptides listed above and the methods by which they were identified and prepared have been previously described in detail in U.S. Patent Application Publication Nos. U.S. 2009-0048428 and U.S. 2005-0054752, both of which are hereby incorporated by reference.

Persons of ordinary skill in the art will readily appreciate that the foregoing non-limiting listing of distinct classes of peptides is provided for illustrative purposes only, as examples of the scope of distinct sets of targeting peptides that may be incorporated into a fusion peptide of the formula PEP1-L-PEP2 wherein L is an acid-cleavable linker encompassed by the invention disclosed herein.

DETAILED DESCRIPTION OF THE INVENTION

The following definitions are used herein and should be referred to for interpretation of the claims and the specification. Unless otherwise noted, all U.S. patents and U.S. Patent Applications referenced herein are incorporated by reference in their entirety.

As used herein, the articles "a", "an", and "the" preceding an element or component of the invention are intended to be nonrestrictive regarding the number of instances (i.e., occurrences) of the element or component. Therefore "a", "an", and "the" should be read to include one or at least one, and the singular word form of the element or component also includes the plural unless the number is obviously meant to be singular.

As used herein, the term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein, the term "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

As used herein, the term "pigment" refers to an insoluble, organic or inorganic colorant.

As used herein, the term "hair" as used herein refers to human hair, eyebrows, and eyelashes.

As used herein, the term "skin" as used herein refers to human skin, or substitutes for human skin, such as pig skin, VITRO-SKIN® and EPIDERMT™. Skin, as used herein, will refer to a body surface generally comprising a layer of epithelial cells and may additionally comprise a layer of endothelial cells.

As used herein, the term "nails" as used herein refers to human fingernails and toenails.

As used herein, "PBP" means polymer-binding peptide. As used herein, the term "polymer-binding peptide" refers to peptide sequences that bind with high affinity to a specific polymer (U.S. Pat. No. 7,427,656). Examples include peptides that bind to polyethylene (SEQ ID NO:202-208), polypropylene (SEQ ID NOs: 186-192), polystyrene (SEQ ID NOs: 215-217), Nylon (SEQ ID NOs: 209-214), and poly (tetrafluoroethylene) (SEQ ID NOs: 193-201).

As used herein, "HBP" means hair-binding peptide. As used herein, the term "hair-binding peptide" refers to peptide sequences that bind with high affinity to hair. The hair-binding peptide may be comprised of a single hair-binding domain or multiple binding domains wherein at least one of the binding-domains binds to hair (i.e. multi-block peptides). Examples of hair binding peptides have been reported (U.S. patent application Ser. No. 11/074,473 to Huang et al.; WO 0179479; U.S. Patent Application Publication No. 2002/0098524 to Murray et al.; Janssen et al., U.S. Patent Application Publication No. 2003/0152976 to Janssen et al.; WO 2004048399; U.S. application Ser. No. 11/512,910, and U.S. patent application Ser. No. 11/696,380). Examples of hair-binding peptides are provided as SEQ ID NOs: 111-121.

As used herein, "SBP" means skin-binding peptide. As used herein, the term "skin-binding peptide" refers to peptide sequences that bind with high affinity to skin. Examples of skin binding peptides have also been reported (U.S. patent application Ser. No. 11/069,858 to Buseman-Williams; Rothe et. al., WO 2004/000257; and U.S. patent application Ser. No. 11/696,380). Skin as used herein as a body surface will generally comprise a layer of epithelial cells and may additionally comprise a layer of endothelial cells. Examples of skin-binding peptides are provided as SEQ ID NOs: 122-132.

As used herein, "NBP" means nail-binding peptide. As used herein, the term "nail-binding peptide" refers to peptide sequences that bind with high affinity to nail. Examples of nail binding peptides have been reported (U.S. patent application Ser. No. 11/696,380). Examples of nail-binding peptides are provided as SEQ ID NOs: 133-134.

As used herein, an "antimicrobial peptide" is a peptide having the ability to kill microbial cell populations (U.S. Pat. No. 7,427,656). Examples of antimicrobial peptides are provided as SEQ ID NOs: 155-161.

As used herein, "cellulose acetate-binding peptide" refers to a peptide that binds with high affinity to cellulose acetate. Examples of cellulose acetate-binding peptides are provided as SEQ ID NOs: 218-221.

As used herein, "clay-binding peptide" refers to a peptide that binds with high affinity to clay (U.S. patent application Ser. No. 11/696,380). Examples of clay-binding peptides are provided as SEQ ID NOs: 162-172.

As used herein, "calcium carbonate-binding peptide" refers to a peptide that binds with high affinity to calcium carbonate. Examples of calcium carbonate-binding peptides are provided as SEQ ID NOs: 173-185.

As used herein, "tooth-pellicle-binding peptide" refers to a peptide that binds with high affinity to the proteinaceous tooth pellicle layer that lies external to the enamel. Examples of tooth pellicle-binding peptides are provided as SEQ ID NOs: 135-143.

As used herein, "tooth-enamel-binding peptide" refers to a peptide that binds with high affinity to the enamel of the tooth. Examples of tooth enamel-binding peptides are provided as SEQ ID NOs: 144-154.

As used herein, "pigment-binding peptide" refers to a peptide that binds with high affinity to pigment particles of various types. Examples of pigment-binding peptides are peptides that bind to carbon black (SEQ ID NOs: 222-225), Cromophtal yellow (SEQ ID NOs: 226-230) and Sunfast Magenta (SEQ ID NOs: 231-235).

As used herein, the term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). In a further embodiment, the definition of "operably linked" may also be extended to describe the products of chimeric genes, such as fusion peptides. As such, "operably linked" will also refer to the linking of an inclusion body tag to a peptide of interest to be produced and recovered. The inclusion body tag is "operably linked" to the peptide of interest if upon expression the fusion protein is insoluble and accumulates as inclusion bodies in the expressing host cell.

Means to prepare the present peptides are well known in the art (see, for example, Stewart et al., *Solid Phase Peptide Synthesis*, Pierce Chemical Co., Rockford, Ill., 1984; Bodanszky, *Principles of Peptide Synthesis*, Springer-Verlag, New York, 1984; and Pennington et al., Peptide Synthesis Protocols, Humana Press, Totowa, N.J., 1994). The various components of the fusion peptides (inclusion body tag, peptide of interest, and the cleavable linker/cleavage sequence) described herein can be combined using carbodiimide coupling agents (see for example, Hermanson, Greg T., *Bioconjugate Techniques*, Academic Press, New York (1996)), diacid chlorides, diisocyanates and other difunctional coupling reagents that are reactive to terminal amine and/or carboxylic acid groups on the peptides. However, chemical synthesis is often limited to peptides of less than about 50 amino acids length due to cost and/or impurities. In a preferred embodiment, the biological molecules described herein are prepared using standard recombinant DNA and molecular cloning techniques.

As used herein, the terms "polypeptide" and "peptide" will be used interchangeably to refer to a polymer of two or more amino acids joined together by a peptide bond, wherein the peptide is of unspecified length, thus, peptides, oligopeptides, polypeptides, and proteins are included within the present definition. In one aspect, this term also includes post expression modifications of the polypeptide, for example, glycosylations, acetylations, phosphorylations and the like. Included within the definition are, for example, peptides containing one or more analogues of an amino acid or labeled amino acids and peptidomimetics. In a preferred embodiment, the present IBTs are comprised of L-amino acids.

As used herein, the term "bioactive" or "peptide of interest activity" refers to the activity or characteristic associated with the peptide and/or protein of interest. The bioactive peptides may be used in a variety of applications including, but not limited to curative agents for diseases (e.g., insulin, interferon, interleukins, anti-angiogenic peptides (U.S. Pat. No.

6,815,426), and polypeptides that bind to defined cellular targets (with the proviso that the peptide of interest is not an antibody or the $F_{ab}$ fragment of an antibody) such as receptors, channels, lipids, cytosolic proteins, and membrane proteins, to name a few), peptides having antimicrobial activity, peptides having an affinity for a particular material (e.g., hair binding polypeptides, skin binding polypeptides, nail binding polypeptides, tooth enamel-binding polypeptides, pellicle-binding peptides, cellulose binding polypeptides, polymer binding polypeptides, clay binding polypeptides, silicon binding polypeptides, carbon nanotube binding polypeptides, and peptides that have an affinity for particular animal or plant tissues) for targeted delivery of benefit agents. The peptide of interest is typically no more than 300 amino acids in length, preferably less than 200 amino acids in length, and most preferably less than 100 amino acids in length. In a preferred embodiment, the peptide of interest is a peptide selected from a combinatorially generated library wherein the peptide is selected based on a specific affinity for a target substrate.

As used herein, the "benefit agent" refers to a molecule that imparts a desired functionality to a complex involving the peptide of interest for a defined application. The benefit agent may be a peptide of interest itself or may be one or more molecules bound to (covalently or non-covalently), or associated with, the peptide of interest wherein the binding affinity of the targeted polypeptide is used to selectively target the benefit agent to the targeted material. In another embodiment, the targeted polypeptide comprises at least one region having an affinity for at least one target material (e.g., biological molecules, polymers, hair, skin, nail, clays, other peptides, etc.) and at least one region having an affinity for the benefit agent (e.g., pharmaceutical agents, pigments, conditioners, dyes, fragrances, etc.). In another embodiment, the peptide of interest comprises a plurality of regions having an affinity for the target material and a plurality of regions having an affinity for the benefit agent. In yet another embodiment, the peptide of interest comprises at least one region having an affinity for a targeted material and a plurality of regions having an affinity for a variety of benefit agents wherein the benefit agents may be the same of different. Examples of benefits agents may include, but are not limited to conditioners for personal care products, pigments, dyes, fragrances, pharmaceutical agents (e.g., targeted delivery of cancer treatment agents), diagnostic/labeling agents, ultraviolet light blocking agents (i.e., active agents in sunscreen protectants), and antimicrobial agents (e.g., antimicrobial peptides), to name a few.

"Codon degeneracy" refers to the nature in the genetic code permitting variation of the nucleotide sequence without affecting the amino acid sequence of an encoded polypeptide. Accordingly, the instant invention relates to any nucleic acid fragment that encodes the present amino acid sequences. The skilled artisan is well aware of the "codon-bias" exhibited by a specific host cell in usage of nucleotide codons to specify a given amino acid. Therefore, when synthesizing a gene for expression in a host cell, it is desirable to design the gene such that its frequency of codon usage approaches the frequency of preferred codon usage of the host cell.

As used herein, the term "solubility" refers to the amount of a substance that can be dissolved in a unit volume of a liquid under specified conditions. In the present application, the term "solubility" is used to describe the ability of a peptide (inclusion body tag, peptide of interest, or fusion peptides) to be resuspended in a volume of solvent, such as a biological buffer. In one embodiment, the peptides targeted for production ("peptides of interest") are normally soluble in the cell and/or cell lysate under normal physiological conditions. Fusion of one or more inclusion body tags (IBTs) to the target peptide results in the formation of a fusion peptide that is insoluble under normal physiological conditions, resulting in the formation of inclusion bodies. In one embodiment, the peptide of interest is insoluble in an aqueous medium having a pH range of 5-12, preferably 6-10; and a temperature range of 5° C. to 50° C., preferably 10° C. to 40° C.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any naturally-occurring amino acid (or as defined by the formulas described herein) | Xaa | X |

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences (including coding regions engineered to encode fusion peptides) that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes.

As used herein, the term "coding sequence" refers to a DNA sequence that encodes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, ribosomal binding sites, translation leader sequences, introns, polyadenylation recognition sequences, RNA processing site, effector binding sites, and stem-loop structures. One of skill in the art recognizes that selection of suitable regulatory sequences will depend upon host cell and/or expression system used.

As used herein, the term "genetic construct" refers to a series of contiguous nucleic acids useful for modulating the genotype or phenotype of an organism. Non-limiting examples of genetic constructs include but are not limited to a nucleic acid molecule, and open reading frame, a gene, a plasmid and the like.

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, $5^{th}$ Ed. Current Protocols and John Wiley and Sons, Inc., N.Y., 2002.

As used herein, the terms "fusion peptide", "fusion protein", "chimeric protein", and "chimeric peptide" can be used interchangeably and refer to a polymer of amino acids (peptide, oligopeptide, polypeptide, or protein) comprising at least two portions, each portion comprising a distinct functionally independent peptide. In a fusion peptide wherein a first peptide PEP1 and a second peptide, PEP2, are both directly and covalently bound to an acid cleavable linker, L, through peptide bonds, a result of acid cleavage of the acid cleavable peptide linker, L, will be to disrupt the covalent bond between PEP1 and PEP2 rendering them soluble but no longer covalently joined. The result is that PEP1 and PEP2 would be separable by conventional biochemical methodology.

As used herein, the term "heterologous" refers to peptides and polypeptides that are not naturally encoded by a cell's genome, but are programmed to be synthesized by a cell that has been recombinantly engineered by standard gene transfer methods. As used herein, the term heterologous encompasses the fusion peptides of the invention, which are encoded by expression vectors that are introduced into the desired cell type. As used herein, a recombinant cell, a recombinant microbial cell, a recombinant yeast cell and a recombinant bacterial cell are cells that have been genetically or recombinantly engineered to synthesize the heterologous fusion peptides of the invention. In some cases, the synthesis of a heterologous peptide or polypeptide may be the result of the infection of a cell by either a eukaryotic virus or a prokaryotic bacteriophage.

In one embodiment, the invention encompasses a method of isolating a peptide of interest ("POI") from a recombinant cell expressing a heterologous fusion peptide comprising the linker L. The recombinant cell may be any prokaryotic or eukaryotic cell type, including microbial cells. Preferred recombinant microbial cells include recombinant yeast and recombinant bacterial cells. An additional embodiment contemplates taking advantage of the fact that heterologous peptide expression in recombinant cells is often accompanied by the newly synthesized heterologous fusion peptides accumulating in insoluble inclusion bodies within the nucleus or the cytoplasm of the cell. When such insoluble fusion peptides having a POI also comprise the acid-cleavable linker L, it is contemplated herein that acid hydrolysis of L will liberate the POI from the inclusion body, preferably to a more soluble form. The released soluble form of the POI is then more easily separable from remaining inclusion bodies and insoluble remnants thereof.

As used herein, an "inclusion body" is an insoluble intracellular deposit of aggregated heterologous polypeptide(s) found in the cytoplasm or nucleus of a recombinant prokaryotic or eukaryotic cell. In a preferred embodiment the inclusion body is found in a recombinant microbial cell. In an even more preferred embodiment the recombinant microbial cell is a recombinant yeast cell or a recombinant bacterial cell. In a further preferred embodiment the recombinant bacterial cell is a recombinant *Escherichia coli*.

As used herein, the term "solubility tag" or "inclusion body tag," i.e., "IBT," will refer to a peptide or polypeptide that facilitates formation of inclusion bodies when fused to a peptide of interest. The peptide of interest is preferably soluble within the host cell and/or host cell lysate when not fused to an inclusion body tag. Fusion of the peptide of interest to an inclusion body tag produces a fusion protein that accumulates into intracellular bodies (inclusion bodies) within the host cell.

Peptides of interest that are typically soluble within the host cell and/or cell lysates can be fused to one or more inclusion body tags to facilitate formation of an insoluble fusion protein. In an alternative embodiment, the peptide of interest may be partially insoluble in the host cell, but produced at relatively lows levels where significant inclusion body formation does not occur. As such, the formation of inclusion bodies will increase peptide production. In a further embodiment, fusion of the peptide of interest to one or more inclusion body tags (IBTs) increases the amount of protein produced in the host cell. Formation of the inclusion body facilitates simple and efficient purification of the fusion peptide from the cell lysate using techniques well known in the art such as centrifugation and filtration. In another embodiment, the inclusion body tag comprises an effective number of cross-linkable cysteine residues useful for separating the IBT from the peptide of interest (post cleavage into a mixture of peptide fragments) with the proviso that the peptide of interest is devoid of cysteine residues. The fusion protein typically includes one or more cleavable peptide linkers used to separate the protein/polypeptide of interest from the inclusion body tag(s). The cleavable peptide linker is designed so that the inclusion body tag(s) and the protein/polypeptide(s) of interest can be easily separated by cleaving the linker element. The peptide linker can be cleaved chemically (e.g., acid hydrolysis) or enzymatically (i.e., use of a protease/peptidase that preferentially recognizes an amino acid cleavage site and/or sequence within the cleavable peptide linker).

After the inclusion bodies are separated and/or partially-purified or purified from the cell lysate, the cleavable linker elements can be cleaved chemically and/or enzymatically to separate the inclusion body tag from the peptide of interest. The fusion peptide may also include a plurality of regions encoding one or more peptides of interest separated by one or more cleavable peptide linkers.

As used herein, "acid-cleavable linker," "acid-labile linker," "acid-cleavable peptide," and "acid cleavage site" may be used interchangeably and refers to a peptide that displays at least one acid-cleavable peptide bond under the conditions specified herein. The linker function of the acid-cleavable peptide is based on the fact that the linker is covalently bonded to at least two peptides, PEP1 and PEP2 wherein the at least two peptides are either identical or distinct from each other. Cleaving the linker, L, results in the breaking of a peptide bond, e.g., the bond between an aspartic acid and a proline residue or between two proline residues. The result would be that PEP1 and PEP2 would no longer be covalently joined.

In one embodiment, the acid-cleavable linker is bonded at either its carboxy terminus or amino terminus to an inclusion body tag ("IBT") and a peptide of interest ("POI") at the opposite terminus. Schematically, this may be represented according to the structural formula PEP1-L-PEP2, where either PEP1 or PEP2 may be either an IBT or POI and L represents an acid-cleavable linker.

In a further embodiment of PEP1-L-PEP2, both PEP1 and PEP2 are POIs. In such an embodiment, the fusion peptide is likely to be soluble, as would be the cleaved forms of PEP1 and PEP2. In an additional embodiment, wherein both PEP1 and PEP2 are POIs, it may unexpectedly arise that the fusion peptide is insoluble in the recombinant cell. This is likely to arise when either of the POIs unexpectedly functions as an IBT. In such cases, the acid-cleavage and peptide isolation may proceed as in the case where one of either PEP1 or PEP2 is a known IBT peptide.

In the context of the present invention, the term "isolate" or "isolated" refers to separating a given peptide or cellular component (e.g., inclusion body) from other cellular proteins, structures, components, debris, molecules, and the like, without any inference of having achieved a specific degree of purity. For illustration purposes, isolating a fusion peptide, POI or an inclusion body may arise when a mixture of components comprising a fusion peptide, POI or inclusion body is submitted to one or more process steps resulting in an enrichment of the fusion peptide, inclusion body or POI over the starting mixture of components. Isolating any given component separates it from some, but not necessarily all components of a cell homogenate, lysate or extract. Put another way, the term "isolated" may refer to either a purified component or a partially purified component. In the latter, no degree of purity should be inferred. Similarly, the term "separated" or "separating" and the like can be used interchangeably with "isolated" and "isolating," as well as other similarly used terms.

In the context of the claimed invention the term "solution of sufficiently acidic pH" refers to any aqueous or organic liquid having a pH value that is sufficiently low to cleave the acid-cleavable linker L. These include organic solvents, water, or any saline, or buffered saline, or growth medium having a pH value that is sufficiently low to cleave the acid-cleavable linker L. A solution of sufficiently acidic pH encompasses solutions that are formulated to lower the intracellular pH of intact cells, the pH of the environment of disrupted or solubilized cells, or any mixture of cellular components, in order to promote the cleavage of linker L within the fusion peptide PEP1-L-PEP2.

A "POI" (i.e., protein of interest) is any peptide having one or more activities or functions that render it of interest to persons of ordinary skill in the art. Accordingly, the POI can possess any kind of functionality including, but not limited to, receptors, ligands, enzymes, diagnostic markers, cellular or viral structural components and the like. The term "independently functional" indicates that a POI or IBT demonstrates its activities or functions without participation by, or interaction with, an additional component of the fusion peptide PEP1-L-PEP2. Thus, for example, after hydrolytic release from either a soluble or insoluble fusion peptide, a POI will demonstrate its relevant properties, activities or functions under the proper conditions.

As used herein, a non-POI portion of the fusion peptide PEP1-L-PEP2 is what remains of the fusion peptide after the POI is removed by acid cleavage. Thus, in some instances, the non-POI portion of the fusion peptide could be represented by the IBT alone, or the IBT fused to a portion of the cleaved linker L. When the fusion peptide is insoluble, the non-POI portion of the fusion peptide refers to the insoluble portion of the fusion peptide remaining after acid cleavage of linker L.

Acid Cleavable Linkers and Fusion Peptides

Figure 4:
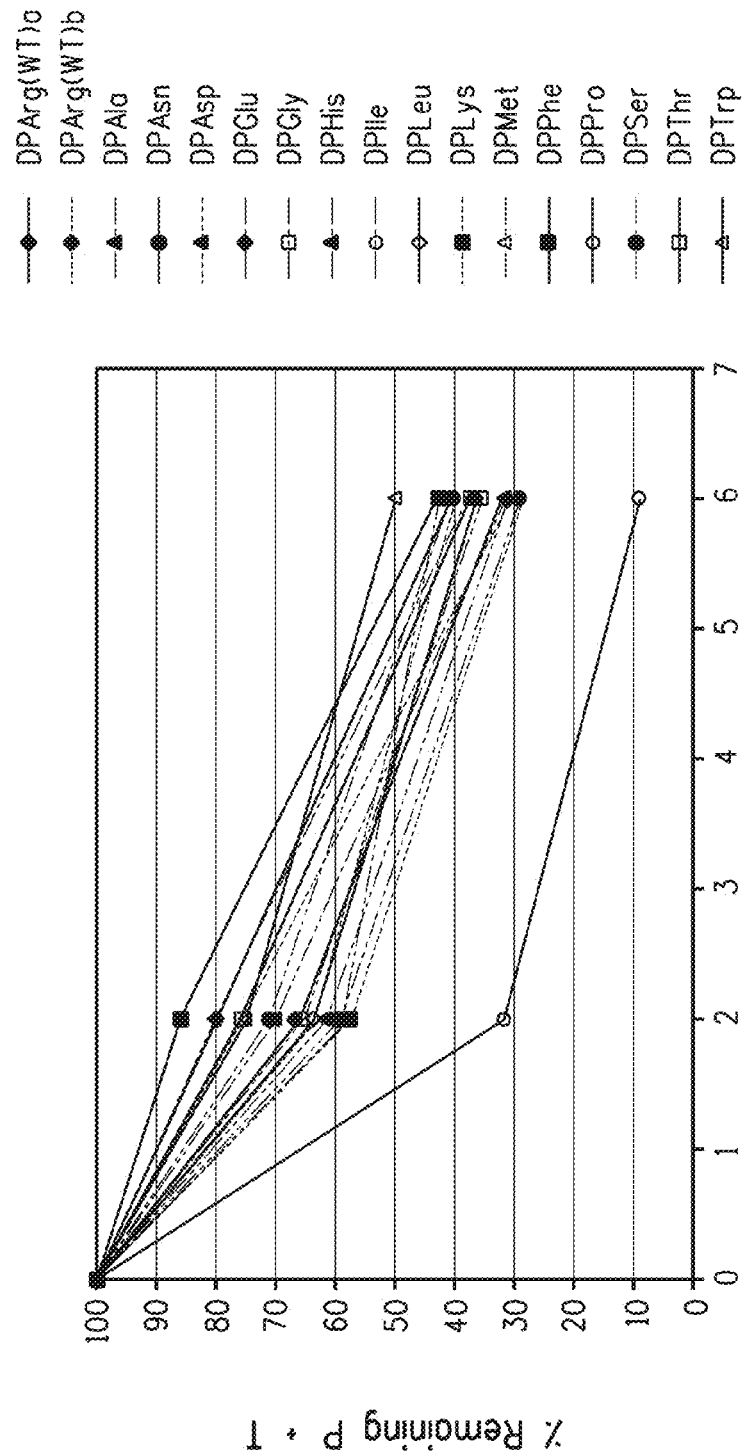
FIG. 4 demonstrates the effect on acid hydrolysis rates of an intact fusion peptide having an amino acid substitution in the position immediately to the carboxy terminal side of the proline residue of a single DP linker; i.e., an aspartic acid-proline pair.

A shown in FIG. 1, multimers of the single acid-cleavable DP pair provided enhanced rates of acid hydrolysis of an intact fusion peptide according to the order DP4>DP3>DP2>DP1 (see Table 2). Experiments in which individual amino acid substitutions were made at the position immediately following (i.e., on the carboxy side) the proline residue in the DP pair indicated that adding the aspartic acid had little if any effect (FIG. 4). The only amino acid substitution at this position that significantly enhanced the rate of acid hydrolysis was an additional proline (FIG. 4). Thus, the resultant sequence DPP reduced the half-time of acid hydrolysis by approximately two-fold over rate observed with the DP pair (FIG. 4).

Figure 3:
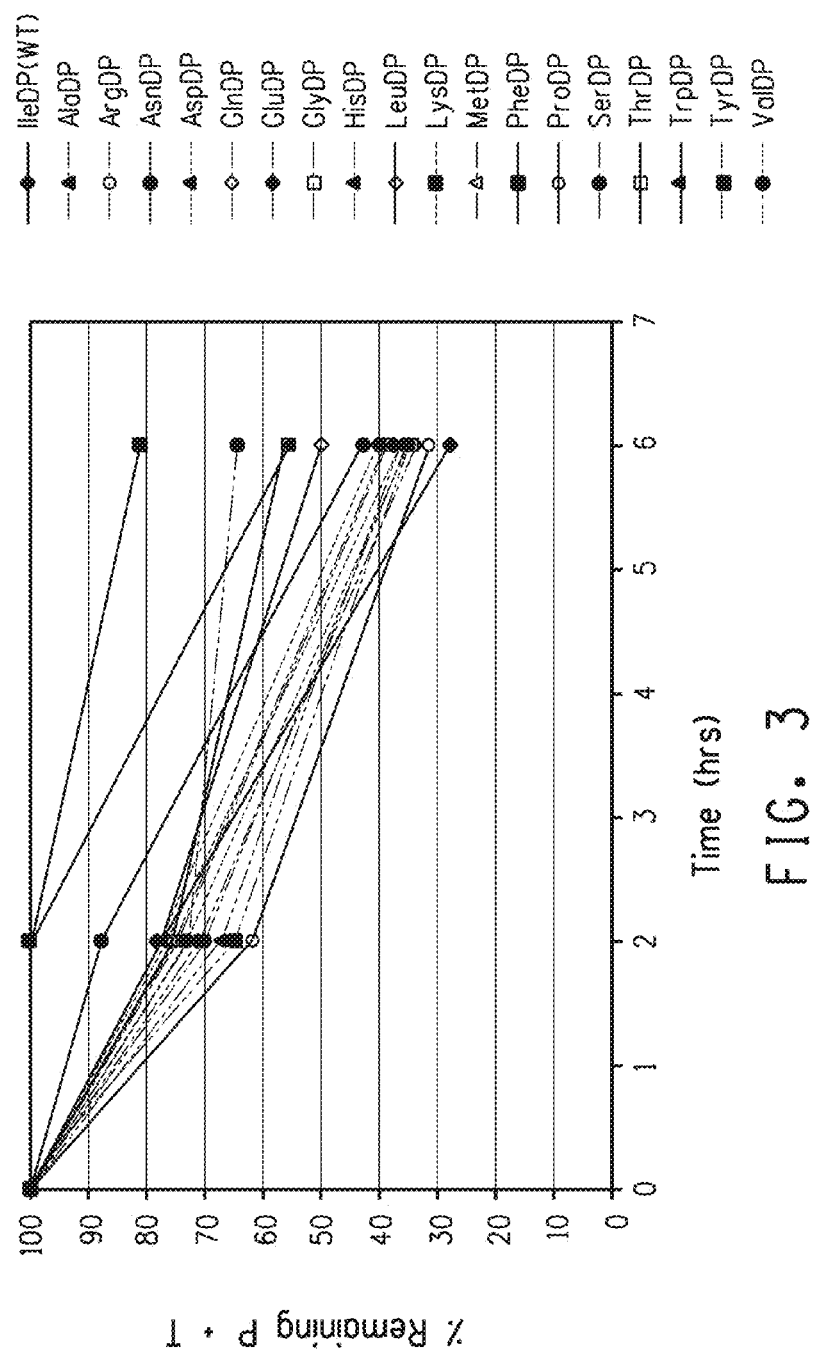
FIG. 3 demonstrates the effect on acid hydrolysis rates of an intact fusion peptide having an amino acid substitution in the position immediately to the amino terminal side of the aspartic acid residue of a single DP linker; i.e., an aspartic acid-proline pair.

Similar amino acid substitutions were made on the amino terminal side of the DP pair's aspartic acid residue (FIG. 3). While not as marked an effect as in the previous experiment, proline on the amino terminus side of the DP pair also had the shortest $t_{1/2}$ of all amino acid substitutions. Of note is that the hydrophobic amino acids tryptophan and phenylalanine were actually significantly more inhibiting the acid hydrolysis than the other amino acids.

With this background, additional linkers were designed and prepared as indicated in Table 2. For illustration purposes only Table 2 provides a non-limiting number of embodiments of acid-cleavable peptide linkers that can be achieved given the empirical observations disclosed herein. Given this background and the technical guidance disclosed herein persons of ordinary skill in the art would be able to add to the list of acid-cleavable linkers that are encompassed by the inventive concept detailed in this specification and to the numerous uses for which cleavable peptide linkers are generally known in the art. For example the invention is useful for the expression and recovery of recombinantly produced peptides and proteins. Such proteins typically have high value in any number of applications including, but not limited to medical, biomedical, diagnostic, personal care, and affinity applications where the peptides of interest are used as linkers to various surfaces.

In one embodiment, the invention encompasses an acid-cleavable peptide linker, L, selected from the group consisting of:

```
A.  DPDP,           (SEQ ID NO: 1)

B.  DPDPDP,         (SEQ ID NO: 2)

C.  DPDPDPDP,       (SEQ ID NO: 3)

D.  DPDPDPP,        (SEQ ID NO: 4)

E.  DPDPPDPP,       (SEQ ID NO: 5)

F.  DPDPPDP,        (SEQ ID NO: 6)
and

G.  DPPDPPDP,       (SEQ ID NO: 7)
``` wherein D is aspartic acid and P is proline;

In a preferred embodiment, the acid-cleavable peptide linker, L, is selected from the group consisting of DPDPDPP (SEQ ID NO:4), DPDPPDPP (SEQ ID NO:5), DPDPPDP (SEQ ID NO:6), and DPPDPPDP (SEQ ID NO:7).

The enhancement in the rate of acid hydrolysis demonstrated by the linkers of the invention is defined as the rate of acid hydrolysis of an intact fusion peptide comprising the acid-cleavable linker of the invention, as compared to the rate of acid hydrolysis of a fusion peptide when the linker comprises a single DP pair. In the context of this invention and throughout the specification, the acid-cleavable linkers may be referred to in a short-hand notation. Table 2 provides a nonlimiting illustrative list of specific embodiments of the acid-cleavable linkers showing their short-hand designations as well as their sequences and SEQ ID NO:.

TABLE 2

Embodiments of Linker L

| Linker Name | Amino Acid Sequence | SEQ ID NO: |
|---|---|---|
| DP2 | DPDP | 1 |
| DP3 | DPDPDP | 2 |
| DP4 | DPDPDPDP | 3 |
| PP1 | DPDPDPP | 4 |
| PP2 | DPDPPDPP | 5 |
| PP3 | DPDPPDP | 6 |
| PP4 | DPPDPPDP | 7 |

An additional embodiment of the invention encompasses a fusion peptide or fusion polypeptide comprising the acid-cleavable peptide linker wherein the fusion peptide has the structure,

PEP1-L-PEP2, wherein PEP1 and PEP2 are functional peptides or polypeptides that are covalently linked to one another through the acid-cleavable peptide linker L.

In an additional embodiment of the invention, a fusion peptide or fusion polypeptide consisting essentially of one of the present acid-cleavable peptide linkers is provided wherein the fusion peptide has the structure,

PEP1-L-PEP2, wherein PEP1 and PEP2 are functional peptides or polypeptides that are covalently linked to one another through the acid-cleavable peptide linker L.

Either PEP1 or PEP2, or both, may be a peptide of interest ("POI"). Such an embodiment of the fusion peptide may be soluble or insoluble in the cytoplasm of a recombinant cell. In the case wherein PEP1 and PEP2 are POIs that confer cytoplasmic solubility to the fusion peptide, the fusion peptide may be isolated from cellular components or even purified prior to acidic cleavage of linker L. Thus, the acid-cleavable linkers and fusion peptide of the present invention provide suitable means for the separation of a POI from a soluble fusion peptide.

As a nonlimiting illustrative example, the POI (e.g., PEP1) may be fused through L to an antigenic peptide (e.g., PEP2) to which specific antibodies are known. Conventional methodology thereby allows the fusion peptide to be isolated by immunological means, e.g., affinity chromatography on a column comprising an immobilized antibody directed to the antigenic peptide, as a first isolation step. Then after subsequent acid hydrolysis of the purified fusion peptide, the antigenic peptide may be separated from the POI by again submitting the acid-treated mixture to another round of affinity chromatography or immunoadsorption; e.g., on an affinity column or other affinity-substrate. Thus, the fusion peptide PEP1-L-PEP2 is suitably versatile to aid in the purification of POIs from soluble fusion peptides as well as from insoluble inclusion bodies.

As an additional nonlimiting illustrative example, the POI (e.g., PEP1) may be fused through L to a metal ion binding domain (e.g., PEP2) for which methods of adsorption to an ion-containing substrate are incorporated to purify the fusion peptide. Examples of such metal-binding domains include the 6×-His tag, or the metallothionein polypeptide or zinc-binding fragment thereof. Persons of ordinary skill in the art will recognize that these methods can be adapted to many situations wherein the newly synthesized fusion peptide remains soluble in the cell cytoplasm and PEP2, i.e. the non-POI portion of the fusion peptide is a known ligand or receptor that can be isolated by adsorption to an appropriate ligand-containing or receptor-containing substrate or support.

In an additional embodiment, one of PEP1 or PEP2 is a POI whereas the other of PEP1 or PEP2 is an inclusion body tag ("IBT"). In the context of this description an IBT functions to direct newly synthesized fusion peptide molecules into insoluble inclusion bodies within the recombinant cell, e.g., bacterial cell cytoplasm. In this embodiment, the acid-cleavable peptide linker provides a relatively simple means to release a POI from the insoluble portion of the fusion peptide comprising the IBT. For example, one could prepare an isolated preparation of inclusion bodies containing the desired fusion peptide wherein either of PEP1 or PEP2 is a POI with the remaining peptide being an IBT. Resuspending, contacting, or incubating the inclusion bodies in an acidic medium of sufficiently low pH and at the appropriate temperature for sufficient time would cleave the acid-cleavable peptide linker joining PEP1 to PEP2, thereby selectively cleaving the linker thereby yielding the POI in a soluble form while the IBT (or non-POI portion of the fusion peptide) remains insoluble. Therefore, the ease of separating the released soluble POI from the insoluble inclusion bodies provides a convenient and effective peptide purification step that can be combined with conventional biochemical peptide isolation methodology.

An additional type of fusion peptide may arise fortuitously, specifically wherein either of PEP1 or PEP2 unexpectedly acts to direct the newly synthesized fusion peptide into inclusion bodies. Stated another way, the situation may arise where a fusion peptide having a specific combination of PEP1 and PEP2, neither of which was known to have IBT-like properties, may unexpectedly accumulate in inclusion bodies. As long as at least one of either PEP1 or PEP2 becomes soluble after acid cleavage, isolation of a POI can be achieved according to the methods disclosed herein.

The acid-cleavable linkers within the fusion peptide cleave at an acidic pH of between about pH 1 and about pH 6, preferably between a pH of about pH 1 and about pH 4, more preferably between about pH 2 and about pH 4, even more preferably between about pH 3 and about pH 4, and most preferably about pH 4. Thus, it follows that the fusion peptide of the present invention would also be expected to be cleaved within the same pH ranges.

The enhanced rates of acid hydrolysis of the linkers and fusion peptides of the present invention are evidenced at a range of temperatures at the appropriate pH. Suitable temperature ranges are between about 40° C. to about 90° C., preferably from about 50° C. to about 80° C., more preferably between about 60° C. to about 70° C., and most preferably about 60° C.

In a further embodiment, the acid-cleavable linker is cleaved by incubating the fusion peptide at a pH of about pH 2 to about pH 4 and at a temperature of about 50° C. to about 80° C.

In view of this description, an even further embodiment of the invention encompassed herein comprises a method of preparing at least one peptide of interest ("POI") from a fusion peptide comprising at least one POI, comprising:

a) providing a recombinant cell synthesizing a fusion peptide having the structure

PEP1-L-PEP2 wherein,
i) PEP1 and PEP2 are independently functional peptides wherein at least one is a peptide of interest ("POI"); and ii) L is an acid-cleavable linker comprising a peptide selected from the group consisting of:

| | | |
|---|---|---|
| A. | DPDP, | (SEQ ID NO: 1) |
| B. | DPDPDP, | (SEQ ID NO: 2) |
| C. | DPDPDPDP, | (SEQ ID NO: 3) |
| D. | DPDPDPP, | (SEQ ID NO: 4) |
| E. | DPDPPDPP, | (SEQ ID NO: 5) |
| F. | DPDPPPDP, and | (SEQ ID NO: 6) |
| G. | DPPDPPDP, | (SEQ ID NO: 7) | wherein D is aspartic acid and P is proline;
b) contacting the fusion peptide with a solution of sufficiently acidic pH so that linker L is cleaved, and
c) isolating the at least one POI.

It is contemplated that the recombinant cell be either prokaryotic or eukaryotic. Preferably, the recombinant cell is a microbial cell, and more preferably a recombinant bacterial cell. A preferred recombinant bacterial cell is a recombinant *Escherichia coli* cell.

The method of preparing the POI comprises an acid cleaving step that is performed at an acidic pH of between about 1 and about 6, preferably between a pH of about 1 and about 4, and more preferably between about 2 and about 3.

With respect to temperature, the acid cleaving step is performed at a suitable temperature range of between about 40° C. to about 90° C., preferably from about 50° C. to about 80° C., and more preferably between about 50° C. or 60° C. to about 70° C.

For the purpose of practicing the inventive method inclusion bodies may be isolated from recombinant cells using any known methods. The release of the POI from the insoluble IBT-containing complex can be affected in preparations of inclusion bodies of varied purity. Therefore the inventive method may be used in conjunction with various additional methods of isolating inclusion bodies based on the specific needs of persons of ordinary skill in the art. In another embodiment, the inclusion bodies in whole recombinant cell homogenates or whole recombinant cell extracts may be acid treated without further enrichment or purification and still provide acid hydrolytic release of the POI to a soluble form that is separable from the insoluble remnant of the fusion peptide and the remaining inclusion bodies. In an even further embodiment, the invention encompasses a recombinant cell, more specifically a recombinant yeast cell or recombinant bacterial cell, which expresses such a fusion peptide. In this context an especially desirable recombinant bacterial cell is *Escherichia coli*.

A still further embodiment of the invention is the isolated or purified inclusion bodies comprising a fusion peptide of interest. The inclusion bodies comprising the fusion peptide PEP1-L-PEP2 function as a convenient means to store, freeze, transport POIs in a form from which they are easily separated from the unwanted portion by acid hydrolysis and isolated by conventional biochemical techniques.

Inclusion Body Tags

The fusion peptide comprising an IBT may further comprise an effective number of cross-linkable cysteine residues. As described in co-pending U.S. Provisional Patent Application No. 60/951,754 entitled "Recombinant Peptide Production Using a Cross-Linkable Solubility Tag", the inclusion of an effective number of cross-linkable cysteine residues is useful to selectively precipitate and separate the IBT from the POI during processing. Upon acidic cleavage of the fusion peptide, the mixture of fragments (IBTs and POIs) is subjected to oxidizing conditions for a period of time sufficient to cross-link the effective number of cysteine residues incorporated into the IBT. The oxidative cross-linking selectively precipitates the IBTs from the soluble peptide of interest with the proviso that the peptide of interest is devoid of cross-linkable cysteine residues.

IBTs comprising cysteine residues may be effectively used as solubility tags in combination with a peptide of interest having cross-linkable cysteine residues. However, in such situations an oxidative-cross linking step will typically be omitted during subsequent POI isolation.

Peptides of Interest

The peptide of interest ("POI") targeted for production using the present method is one that is appreciably soluble in the host cell and/or host cell liquid lysate under normal physiological conditions. In a preferred aspect, the peptides of interest are generally short (<300 amino acids in length) and difficult to produce in sufficient amounts due to proteolytic degradation. Fusion of the peptide of interest to at least one of the present inclusion body forming tags creates a fusion peptide that is insoluble in the host cell and/or host cell lysate under normal physiological conditions. Production of the peptide of interest is typically increased when expressed and accumulated in the form of an insoluble inclusion body as the peptide is generally more protected from proteolytic degradation. Furthermore, the insoluble fusion protein can be easily separated from the host cell lysate using centrifugation or filtration.

In general, the inventive acid-cleavable linkers can be used in a process to produce any peptide of interest that is (1) typically soluble in the cell and/or cell lysate under typical physiological conditions and/or (2) those that can be produced at significantly higher levels when expressed in the form of an inclusion body. In a preferred embodiment, the peptide of interest is appreciably soluble in the host cell and/or corresponding cell lysate under normal physiological and/or process conditions.

The length of the peptide of interest may vary as long as (1) the peptide is appreciably soluble in the host cell and/or cell lysate, and/or (2) the amount of the targeted peptide produced is significantly increased when expressed in the form of an insoluble fusion peptide/inclusion body (i.e. expression in the form of a fusion protein protect the peptide of interest from proteolytic degradation). Typically the peptide of interest is less than 300 amino acids in length, preferably less than 100 amino acids in length, more preferably less than 75 amino acids in length, even more preferably less than 50 amino acids in length, and most preferably less than 25 amino acids in length.

The function of the peptide of interest is not limited by the present method and may include, but is not limited to bioactive molecules such as curative agents for diseases (e.g., insulin, interferon, interleukins, peptide hormones, anti-angiogenic peptides, and peptides (with the proviso that the peptide is not an antibody or an $F_{ab}$ portion of an antibody) that bind to and affect defined cellular targets such as receptors, channels, lipids, cytosolic proteins, and membrane proteins; see U.S. Pat. No. 6,696,089,), peptides having an affinity for a particular material (e.g., biological tissues, biological molecules, hair-binding peptides (U.S. Patent Application Publication Nos. 2005-0226839, 2003-0152976, and 2002-0098524; International Patent Application Publication Nos. WO01/79479 and WO04/048399; and U.S. Pat. Nos. 7,736,633; 7,427,656; and 7,749,957), skin-binding peptides (U.S.

Pat. Nos. 7,309,482; 7,427,656; 7,749,957; and 7,341,604), nail-binding peptides (U.S. Patent Application Publication No. 2005-0226839; U.S. Pat. No. 7,749,957), cellulose-binding peptides, polymer-binding peptides (U.S. Pat. Nos. 7,632,919; 7,928,076; 7,700,716; and 7,906,617), and clay-binding peptides (U.S. Pat. No. 7,749,957), for targeted delivery of at least one benefit agent (U.S. Pat. Nos. 7,220,405 and 7,749,957; and U.S. Patent Application Publication No. 2005-0226839).

In a preferred aspect, the peptide of interest is an affinity peptide identified from a combinatorially generated peptide library. In a further aspect, the peptide is selected from a combinatorially generated library wherein said library was prepared using a technique selected from the group consisting of phage display, yeast display, bacterial display, ribosomal display and mRNA display.

In a preferred aspect, the peptide of interest is selected from the group of hair binding peptides, skin binding peptides, nail binding peptides, tooth binding peptides, antimicrobial peptides, pigment binding peptides, clay-binding peptides, mineral binding peptides (e.g., calcium carbonate), and various polymer binding peptides.

Affinity peptides are particularly useful to target benefit agents imparting a desired functionality to a target material (e.g., hair, skin, etc.) for a defined application (U.S. Pat. Nos. 7,220,405; 7,736,633; and 7,749,957; and U.S. Patent Application Publication No. 2005-0226839 for a list of typical benefit agents such as conditioners, pigments/colorants, fragrances, etc.). The benefit agent may be peptide of interest itself or may be one or more molecules bound to (covalently or non-covalently), or associated with, the peptide of interest wherein the binding affinity of the peptide of interest is used to selectively target the benefit agent to the targeted material. In another embodiment, the peptide of interest comprises at least one region having an affinity for at least one target material (e.g., biological molecules, polymers, hair, skin, nail, other peptides, etc.) and at least one region having an affinity for the benefit agent (e.g., pharmaceutical agents, antimicrobial agents, pigments, conditioners, dyes, fragrances, etc.). In another embodiment, the peptide of interest comprises a plurality of regions having an affinity for the target material and a plurality of regions having an affinity for one or more benefit agents. In yet another embodiment, the peptide of interest comprises at least one region having an affinity for a targeted material and a plurality of regions having an affinity for a variety of benefit agents wherein the benefit agents may be the same of different. Examples of benefits agents may include, but are not limited to conditioners for personal care products, pigments, dye, fragrances, pharmaceutical agents (e.g., targeted delivery of cancer treatment agents), diagnostic/labeling agents, ultraviolet light blocking agents (i.e., active agents in sunscreen protectants), and antimicrobial agents (e.g., antimicrobial peptides), to name a few.

Cleavable Peptide Linkers

Fusion peptides comprising inclusion body tags will typically include at least one cleavable sequence separating the inclusion body tag from the polypeptide of interest. The cleavable sequence facilitates separation of the inclusion body tag(s) from the peptide(s) of interest. In one embodiment, the cleavable sequence may be provided by a portion of the inclusion body tag and/or the peptide of interest (e.g., inclusion of an acid cleavable aspartic acid—proline moiety). In a preferred embodiment, the cleavable sequence is provided by including (in the fusion peptide) at least one cleavable peptide linker between the inclusion body tag and the peptide of interest.

Generally, means to cleave peptide linkers include chemical hydrolysis, enzymatic agents, and combinations thereof. In one embodiment, one or more chemically cleavable peptide linkers are included in the fusion construct to facilitate recovery of the peptide of interest from the inclusion body fusion protein. Examples of chemical cleavage reagents include cyanogen bromide (cleaves methionine residues), N-chloro succinimide, iodobenzoic acid or BNPS-skatole [2-(2-nitrophenylsulfenyl)-3-methylindole] (cleaves tryptophan residues), dilute acids (cleaves at aspartic acid-proline bonds), and hydroxylamine (cleaves at asparagine-glycine bonds at pH 9.0); see Gavit, P. and Better, M., *J. Biotechnol.*, 79:127-136 (2000); Szoka et al., *DNA*, 5(1):11-20 (1986); and Walker, J. M., *The Proteomics Protocols Handbook*, 2005, Humana Press, Totowa, N.J.)).

In a preferred embodiment, one or more aspartic acid—proline acid-cleavable recognition sites (i.e., a cleavable peptide linker comprising one or more D-P dipeptide moieties) are included in the fusion protein construct to facilitate separation of the inclusion body tag(s) from the peptide of interest.

In another embodiment, the fusion peptide may include multiple regions encoding peptides of interest separated by one or more cleavable peptide linkers.

In another embodiment, one or more enzymatic cleavage sequences are included in the fusion protein construct to facilitate recovery of the peptide of interest. Examples of enzymes useful for cleaving the peptide linker may include, but are not limited to Arg-C proteinase, Asp-N endopeptidase, chymotrypsin, clostripain, enterokinase, Factor Xa, glutamyl endopeptidase, Granzyme B, *Achromobacter* proteinase I, pepsin, proline endopeptidase, proteinase K, Staphylococcal peptidase I, thermolysin, thrombin, trypsin, and members of the Caspase family of proteolytic enzymes (e.g. Caspases 1-10) (Walker, J. M., supra). An example of a cleavage site sequence is the Caspase-3 cleavage site (Thornberry et al., *J. Biol. Chem.*, 272:17907-17911 (1997) and Tyas et al., *EMBO Reports*, 1(3):266-270 (2000)).

Typically, the cleavage step occurs after the insoluble inclusion bodies and/or insoluble fusion peptides are isolated from the cell lysate. The cells can be lysed using any number of means well known in the art (e.g. mechanical and/or chemical lysis). Methods to isolate the insoluble inclusion bodies/fusion peptides from the cell lysate are well known in the art (e.g., centrifugation, filtration, and combinations thereof). Once recovered from the cell lysate, the insoluble inclusion bodies and/or fusion peptides can be treated with a cleavage agent (chemical or enzymatic) to cleavage the inclusion body tag from the peptide of interest. In one embodiment, the fusion protein and/or inclusion body is diluted and/or dissolved in a suitable solvent prior to treatment with the cleavage agent. In a further embodiment, the cleavage step may be omitted if the inclusion body tag does not interfere with the activity of the peptide of interest.

After the cleavage step, and in a preferred embodiment, the peptide of interest can be separated and/or isolated from the fusion protein and the inclusion body tags based on a differential solubility of the components. Parameters such as pH, salt concentration, and temperature may be adjusted to facilitate separation of the inclusion body tag from the peptide of interest. In one embodiment, the peptide of interest is soluble while the inclusion body tag and/or fusion protein is insoluble in the defined process medium (typically an aqueous medium). In another embodiment, the peptide of interest is insoluble while the inclusion body tag is soluble in the defined process medium.

In a preferred embodiment, the inclusion body tag comprises an effective number of cross-linkable cysteine residues with the proviso that the peptide of interest is devoid of cysteine residues (U.S. Pat. No. 7,951,559). Upon cleavage, oxidative cross-linking is used to selectively cross-link the IBTs (typically insoluble). The conditions are controlled so that the cross-linked IBTs are insoluble while the peptide of interest remains soluble. The soluble peptide of interest is subsequently separated from the cross-linked IBTs using a conventional separation techniques such as centrifugation.

In an optional embodiment, the peptide of interest may be further purified using any number of purification techniques in the art such as ion exchange, gel purification techniques, and column chromatography (see U.S. Pat. No. 5,648,244), to name a few.

Fusion Peptides

Inclusion body tags are used to create chimeric polypeptides ("fusion peptides" or "fusion proteins") that are insoluble within the host cell, forming inclusion bodies. Methods of synthesis and expression of genetic constructs encoding the present fusion peptides is well known to one of skill in the art.

The present fusion peptides will include at least one inclusion body tag (IBT) functionally linked to at least one peptide of interest (POI) via an acid-cleavable linker of the present invention. Typically, the fusion peptides will also include at least one cleavable peptide linker having a cleavage site between the inclusion body tag and the peptide of interest. In one embodiment, the inclusion body tag may include a cleavage site whereby inclusion of a separate cleavable peptide linker may not be necessary. In a preferred embodiment, the cleavage method is chosen to ensure that the peptide of interest is not adversely affected by the cleavage agent(s) employed. In a further embodiment, the peptide of interest may be modified to eliminate possible cleavage sites with the peptide so long as the desired activity of the peptide is not adversely affected.

One of skill in the art will recognize that the elements of the fusion protein can be structured in a variety of ways. Typically, the fusion protein will include at least one IBT (i.e., PEP1), at least one peptide of interest (POI) (i.e., PEP2), and at least one cleavable peptide linker (L) located between the IBT and the POI. Thus, such a fusion peptide conforms to the general structure PEP1-L-PEP2. The inclusion body tag may be organized as a leader sequence or a terminator sequence relative to the position of the peptide of interest within the fusion peptide. In another embodiment, a plurality of IBTs, POIs, and Ls are used when engineering the fusion peptide.

In a further embodiment, the fusion peptide may include a plurality of IBTs (as defined herein), POIs, and Ls that are the same or different.

In another embodiment of the fusion peptide, neither of PEP1 or PEP2 comprises an IBT, but rather the fusion peptide remains soluble. As a nonlimiting illustrative, example, the POI (e.g., PEP1) may be fused through L to an antigenic peptide (e.g., PEP2) to which specific antibodies are known. Conventional methodology thereby allows the fusion peptide to be isolated by immunological means, e.g., affinity chromatography on a column comprising an immobilized antibody directed to the antigenic peptide, as a first isolation step. Then after subsequent acid hydrolysis of the purified fusion peptide, the antigenic peptide may be separated from the POI by again submitting the acid-treated mixture to another round of affinity chromatography or immunoadsorption on; e.g., an affinity column or other affinity-substrate. Thus, the fusion peptide PEP1-L-PEP2 is suitably versatile to aid in the purification of POIs from soluble fusion peptides as well as from insoluble inclusion bodies.

The fusion peptide should be insoluble in an aqueous medium at a temperature of about 10° C. to about 50° C., preferably about 10° C. to about 40° C. The aqueous medium typically comprises a pH range of about pH 5 to about pH 12, preferably about pH 6 to about pH 10, and most preferably about pH 6 to about pH 8. The temperature, pH, and/or ionic strength of the aqueous medium can be adjusted to obtain the desired solubility characteristics of the fusion peptide/inclusion body.

Method of Making a Peptides of Interest Using Insoluble Fusion Peptides

The inclusion body tags are used to make fusion peptides that form inclusion bodies within the production host. This method is particularly attractive for producing significant amounts of soluble peptide of interest that (1) are difficult to isolation from other soluble components of the cell lysate and/or (2) are difficult to product in significant amounts within the target production host.

In the present methods, a POI is fused to one end of an inventive acid-cleavable linker while an IBT is fused at the other end thereby forming an insoluble fusion protein. Expression of the genetic construct encoding the fusion protein produces an insoluble form of the peptide of interest that accumulates in the form of inclusion bodies within the host cell. The host cell is grown for a period of time sufficient for the insoluble fusion peptide to accumulate within the cell.

The host cell is subsequently lysed using any number of techniques well known in the art. The insoluble fusion peptide/inclusion bodies are then separated from the soluble components of the cell lysate using a simple and economical technique such as centrifugation and/or membrane filtration. The insoluble fusion peptide/inclusion body can then be further processed in order to isolate the peptide of interest. Typically, this will include resuspension of the fusion peptide/inclusion body in a liquid medium suitable for cleaving the fusion peptide, separating the inclusion body tag from the peptide of interest. The fusion protein is typically designed to include a cleavable peptide linker separating the inclusion body tag from the peptide of interest. The cleavage step can be conducted using any number of techniques well known in the art (chemical cleavage, enzymatic cleavage, and combinations thereof). The peptide of interest can then be separated from the inclusion body tag(s) and/or fusion peptides using any number of techniques well known in the art (centrifugation, filtration, precipitation, column chromatography, etc.). Preferably, the peptide of interest (once cleaved from fusion peptide) has a solubility that is significantly different than that of the inclusion body tag and/or remaining fusion peptide. In a further preferred embodiment, oxidative cross-linking is used to selectively precipitate the IBT (comprising an effective number of cross-linkable cysteine residues) from the peptide of interest (when devoid of cross-linkable cysteine residues). For example, IBT139.CCPGCC, IBT-139(5C), and IBT186, were designed to include an effective number of cross-linkable cysteine residues.

Transformation and Expression

Once the inclusion body tag has been identified and paired with the appropriate peptide of interest, construction of cassettes and vectors that may be transformed in to an appropriate expression host is common and well known in the art. Typically, the vector or cassette contains sequences directing transcription and translation of the relevant chimeric gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Transcription initiation control regions or promoters, which are useful to drive expression of the genetic constructs encoding the fusion peptides in the desired host cell, are numerous and familiar to those skilled in the art. Virtually any promoter capable of driving these constructs is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara (pBAD), tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary; however, it is most preferred if included.

Preferred host cells for expression of the present fusion peptides are microbial hosts that can be found broadly within the fungal or bacterial families and which grow over a wide range of temperature, pH values, and solvent tolerances. For example, it is contemplated that any of bacteria, yeast, and filamentous fungi will be suitable hosts for expression of the present nucleic acid molecules encoding the fusion peptides. Because of transcription, translation, and the protein biosynthetic apparatus is the same irrespective of the cellular feedstock, genes are expressed irrespective of the carbon feedstock used to generate the cellular biomass. Large-scale microbial growth and functional gene expression may utilize a wide range of simple or complex carbohydrates, organic acids and alcohols (i.e. methanol), saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include, but are not limited to fungal or yeast species such as *Aspergillus, Trichoderma, Saccharomyces, Pichia, Yarrowia, Candida, Hansenula*, or bacterial species such as Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, *Methanobacterium, Klebsiella*, and *Myxococcus*. Preferred bacterial host strains include *Escherichia, Pseudomonas*, and *Bacillus*. In a highly preferred aspect, the bacterial host strain is *Escherichia coli*.

Fermentation Media

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the expression of the present fusion peptides.

Culture Conditions

Suitable culture conditions can be selected dependent upon the chosen production host. Typically, cells are grown at a temperature in the range of about 25° C. to about 40° C. in an appropriate medium. Suitable growth media may include common, commercially-prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are typically between pH 5.0 to pH 9.0, where pH 6.0 to pH 8.0 is preferred.

Fermentations may be performed under aerobic or anaerobic conditions where aerobic conditions are generally preferred.

Industrial Batch and Continuous Fermentations

A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass. (hereinafter "Brock"), or Deshpande, Mukund V., *Appl. Biochem. Biotechnol.*, 36:227 (1992).

Although the present invention is typically performed in batch mode it is contemplated that the method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable.

EXAMPLES

The present invention is further defined in the following Examples. It should be understood that these Examples, while indicating preferred embodiments of the invention, are given by way of illustration only. From the above discussion and the guidance provided by the Examples, one skilled in the art can ascertain the essential characteristics of this invention, and without departing from the scope thereof, can make various changes and modifications of the invention to adapt it to various uses and conditions.

The meaning of abbreviations used is as follows: "min" means minute(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmol" means micromole(s), "pmol" means picomole(s), "g" means gram(s), "µg" means microgram(s), "mg" means milligram(s), "g" means the gravitation constant, "rpm" means revolutions per minute, "DTT" means dithiothreitol, and "cat#" means catalog number.

General Methods

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, 5$^{th}$ Ed. Current Protocols and John Wiley and Sons, Inc., N.Y., 2002.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or in Brock (supra). All reagents, restriction enzymes and materials used for the growth and maintenance of bacterial cells were obtained from BD Diagnostic Systems (Sparks, Md.), Invitrogen (Carlsbad, Calif.), Life Technologies (Rockville, Md.), QIAGEN (Valencia, Calif.) or Sigma-Aldrich Chemical Company (St. Louis, Mo.), unless otherwise specified.

Expression Vector pLD001

Plasmid pLD001 (SEQ ID NO: 254) has been previous reported as a suitable expression vector for *E. coli* (see U.S. Patent Application Publication No. 2010-0158823 A1 to Wang et al.; incorporated herein by reference).

The vector pLD001 was derived from the commercially available vector pDEST17 (Invitrogen, Carlsbad, Calif.). It includes sequences derived from the commercially available vector pET31b (Novagen, Madison, Wis.) that encode a fragment of the enzyme ketosteroid isomerase (KSI). The KSI fragment was included as a fusion partner to promote partition of the peptides into insoluble inclusion bodies in *E. coli*. The KSI-encoding sequence from pET31b was modified using standard mutagenesis procedures (QuickChange II, Stratagene, La Jolla, Calif.) to include three additional Cys codons, in addition to the one Cys codon found in the wild type KSI sequence. In addition, all Asp codons in the coding sequence were replaced by Glu codons. Plasmid pLD001, given by SEQ ID NO: 254, was constructed using standard recombinant DNA methods, which are well known to those skilled in the art.

Coding sequences bounded by BamHI and AscI sites may be ligated between BamHI and AscI sites in pLD001 using standard recombinant DNA methods. The resulting gene fusions resulted in a peptide of interest was fused downstream from a modified fragment of ketosteroid isomerase (KSI(C4) E) that served to drive the peptide into insoluble inclusion bodies in *E. coli* (See U.S. Patent Application Publication No. 2009-0029420A1; herein incorporated by reference)

Example 1

Preparation of Plasmid pLX121

A genetic construct was prepared for evaluating the performance of the inventive acid-cleavable linker by fusing the linker to an inclusion body tag on one end, and a soluble peptide of interest at the linker's opposite end. The peptide of interest used in the present examples was prepared from a previously reported peptide-based triblock dispersant (U.S. Patent Application Publication No. 2005-0054752).

Cloning of the TBP1 Gene

The TBP1 gene, encoding the TBP1 peptide, was selected for evaluation of the inventive acid-cleavable linkers. The synthetic TBP1 peptide is peptide-based triblock dispersant comprising a carbon-black binding domain, a hydrophilic peptide linker, and a cellulose binding domain (see Example 15 of U.S. patent application Ser. No. 10/935,254, herein incorporated by reference).

The TBP1 gene (SEQ ID NO: 17) encoding the 68 amino acid peptide TBP101 (SEQ ID NO: 19) was assembled from synthetic oligonucleotides (Sigma-Genosys, Woodlands, Tex.; Table 3).

TABLE 3

Oligonucleotides Used to Prepare the TBP1

| Oligonucleotide Name | Nucleotide Sequence (5'-3') | SEQ ID NO: |
|---|---|---|
| TBP1(+)1 | GGATCCATCGAAGGTCGTTTCCACGAA AACTGGCCGTCTGGTGGCGGTACCTC TACTTCCAAAGCTTCCACCACTACGAC TTCTAGCAAAACCACCACTACAT | 8 |
| TBP1(+)2 | CCTCTAAGACTACCACGACTACCTCCAA AACCTCTACTACCTCTAGCTCCTCTACG GGCGGTGGCACTCACAAGACCTCTACTC AGCGTCTGCTGGCTGCATAA | 9 |
| TBP1(-)1 | TTATGCAGCCAGCAGACGCTGAGTAGAG GTCTTGTGAGTGCCACCGCCCGTAGAG GAGCTAGAGGTAGT | 10 |
| TBP1(-)2 | AGAGGTTTTGGAGGTAGTCGTGGTAGTC TTAGAGGATGTAGTGGTGGTTTTGCTAG AAGTCGTAGTGGT | 11 |
| TBP1(-)3 | GGAAGCTTTGGAAGTAGAGGTACCGC CACCAGACGGCCAGTTTTCGTGGAAAC GACCTTCGATGGATCC | 12 |

Each oligonucleotide was phosphorylated with ATP using T4 polynucleotide kinase. The resulting oligonucleotides were mixed, boiled for 5 min, and then cooled to room temperature slowly. Finally, the annealed oligonucleotides were ligated with T4 DNA ligase to give synthetic DNA fragment TBP1, given as SEQ ID NO: 17, which encodes the TBP101 peptide (SEQ ID NO: 19).

Construction of pINK101 Expression Plasmid:

Lambda phage site-specific recombination was used for preparation and expression of the present fusion proteins (Gateway™ System; Invitrogen, Carlsbad, Calif.). TBP1 was integrated into the Gateway™ system for protein over-expression. In the first step, 2 µL of the TBP1 ligation mixture was used in a 50-µL PCR reaction. Reactions were catalyzed by Pfu DNA polymerase (Stratagene, La Jolla, Calif.), following the standard PCR protocol. Primer 5'TBP1 (5'-CAC-CGGATCCATCGAAGGTCGT-3'; SEQ ID NO: 21) and 3'TBP1 (5'-TCATTATGCAGCCAGCAGCGC-3'; SEQ ID NO: 20) were used for amplification of the TBP1 fragment. The design of these primers adds an additional sequence of CACC and another stop codon TGA were added to the 5' and 3' ends of the amplified fragments.

The amplified TBP1 was directly cloned into pENTR™/D-TOPO® vector (SEQ ID NO: 22) using Invitrogen's pENTR™ directional TOPO® cloning kit (Invitrogen; Catalog K2400-20), resulting in the Gateway™ entry plasmid pENTR-TBP1. This entry plasmid was propagated in One Shot® TOP10 E. coli cells (Invitrogen). The accuracy of the PCR amplification and cloning procedures were confirmed by DNA sequencing analysis. The entry plasmid was mixed with pDEST17 (Invitrogen, SEQ ID NO: 23). LR recombination reactions were catalyzed by LR CLONASE™ (Invitrogen). The destination plasmid, pINK101 was constructed and propagated in the DH5α E. coli strain. The accuracy of the recombination reaction was determined by DNA sequencing. All reagents for LR recombination reactions (i.e., lambda phage site-specific recombination) were provided in Invitrogen's E. coli expression system with the GATEWAY™ Technology kit. The site-specific recombination process followed the manufacturer's instructions (Invitrogen).

The resulting plasmid, named pINK101, contains the coding region for recombinant protein 6H-TBP1, named INK101 (SEQ ID NO 18), which is an 11.6 kDa protein. The protein sequence includes a 6×His tag and a 24 amino acid linker that includes Factor Xa protease recognition site before the sequence of the TBP101 peptide.

The amino acid coding region for the 6×His tag and the following linker comprising the Factor Xa protease recognition site were excised from pINK101 by digestion with the NdeI and BamHI restriction enzymes.

The TBP1 gene (SEQ ID NO:17) encodes a polypeptide (SEQ ID NO:19) having a ST linker flanked by Gly-Gly-Gly amino acids. The system was made more modular by further mutagenesis to change the upstream amino acid sequence from Gly-Gly-Gly to Ala-Gly-Gly (codon GGT changed to GCC) and the downstream Gly-Gly-Gly to Gly-Gly-Ala (codon GGT GGC changed to GGC GCC). These changes provided a NgoMI restriction site and a KasI restriction site flanking the ST linker, thus facilitating replacement of any element in TBP1.

Further modifications were made to TBP101 including the addition of an acid cleavable site to facilitate the removal of any tag sequence encoded by the region between the NdeI and BamHI sites of the expression plasmid. The resulting plasmid was called pLX121 (also referred to as "pINK101DP"; SEQ ID NO: 250). These modifications changed the amino acids E-G to D-P (acid cleavable aspartic acid—proline linkage) using the Stratagene QUIKCHANGE® II Site-Directed Mutagenesis Kit Cat#200523 (La Jolla, Calif.) as per the manufacturer's protocol using the primers INK101+(5'-CCCCTTCACCGGATCCATCGATC-CACGTTTCCACGAAAACTGGCC-3'; SEQ ID NO: 24) and INK101-(5'-GGCCAGTTTTCGTGGAAACGTG-GATCGATGGATCCGGTGAAGGGG-3'; SEQ ID NO: 25). The sequences were confirmed by DNA sequence analysis. The coding region (SEQ ID NO: 251) and the corresponding amino acid sequence of the modified protein (SEQ ID NO: 26), INK101DP, are provided.

INK101DP Peptide (SEQ ID NO: 26):
MSYYHHHHHHLESTSLYKKAGSAAAPFT<u>GSIDPRFHENWPSAGGTSTSKA</u>

<u>STTTTSSKTTTTSSKTTTTTSKTSTTSSSSTGGATHKTSTQRLLAA</u>

The aspartic acid—proline acid cleavable linker is in bold type. The DP pair replaces the EG pair found in the unmodified TBP101 peptide. The modified TBP101 peptide (i.e., a model peptide of interest) is underlined.

The INK101DP peptide conforms to the general structure PEP1-L-PEP2, wherein PEP1 containing the 6×His tag and Factor Xa cleavage site was found to function as an IBT, whereas PEP2 functions as a POI (i.e., a carbon black binding peptide). In this instance, the 6×His tag was found to be necessary for directing the accumulation of the newly synthesized fusion peptide in insoluble inclusion bodies within the recombinant bacterial cell cytoplasm.

Example 2

Acid Hydrolysis of Peptide Linkers Containing Multiple DP Residues

This example demonstrates the enhanced rate of acid hydrolysis of a fusion peptide having a linker comprising more than one consecutively arranged aspartic acid-proline (i.e., DP) pair. Specifically, the rate of acid hydrolysis of fusion peptides having peptide linkers comprising one, two, three or four consecutive DP pairs were measured and compared.

Strain and Media

*Escherichia coli* BL21-A1 was obtained from Invitrogen Corp. (Cat. #607003, Carlsbad, Calif.). Expression plasmid pINK101DP (Example 1) was previously described in U.S. Patent Application Publication No. 2005-0054752) Cells were grown at 37° C. in Miller's LB broth (Cat. #46-050-CM, Mediatech, Inc., Herndon, Va.) with 0.2% L-(+)-arabinose (Cat. #A3256, Sigma-Aldrich, Inc., St. Louis, Mo.) and 100 μg/mL ampicillin (Cat. #A1066, Sigma-Aldrich, Inc., St. Louis, Mo.). Cells were plated on LB agar plates with 100 μg/mL ampicillin (Cat. #L1004, Teknova, Inc., Hollister, Calif.).

Construction of pINK101DP Variants Containing Additional DPs

One to three additional DP residues were added to pINK101DP by site-directed mutagenesis using a QUIKCHANGE™ II Kit (Cat. #200524, Stratagene, La Jolla, Calif.). Primers pairs used to add additional DP residues are provided in Table 4. Reactions were thermocycled in a Gene Amp 9700 using the thermocycling parameters provided in Table 5 (Perkin Elmer Applied Biosystems, Norwalk, Conn.). *Escherichia coli* BL21-A1 was transformed with 1 μL of QUIKCHANGE™ reaction product according to manufacturer's directions and transformants were selected on LB agar plates with 100 μg/mL ampicillin. DNA sequences were obtained for six isolates from each transformation in order to identify those with the desired mutations.

TABLE 4

Mutagenesis Primers

| Primer ID | Nucleotide Sequence | SEQ ID NO: |
|---|---|---|
| for DP2 | CCCCTTCACCGGATCCATCGATCCAG ATCCACGTTTCCACGAAAACTGGCC | 13 |
| for DP3 | CCCCTTCACCGGATCCATCGATCCAG ATCCAGATCCACGTTTCCACGAAAACT GGCC | 14 |
| for DP4 | CCCCTTCACCGGATCCATCGATCCAG ATCCAGATCCAGATCCACGTTTCCAC GAAAACTGGCC | 15 |
| Remote Rev | GTAATACGGTTATCCACAGAATCAG | 16 |

Reaction Components—

| 10X QUIKCHANGE ™ reaction buffer | 5 μL |
| QUIKCHANGE ™ dNTP mix | 1 μL |
| Pfu polymerase | 1 μL |
| 10 μM forward primer | 1 μL |
| 10 μM reverse primer | 1 μL |
| Water | 40 mL |

TABLE 5

Thermocycling program

| Segment | Cycles | Temperature | Time |
|---|---|---|---|
| 1 | 1 | 95° C. | 2 minutes |
| 2 | 18 | 95° C. | 50 seconds |
|  |  | 55° C. | 1 minute |
|  |  | 68° C. | 10 minutes |
| 3 | 1 | 68° C. | 10 minutes |
| 4 | 1 | 4° C. | hold |

Preparation of Peptide-Containing Inclusion Bodies

Strains containing each mutant plasmid were grown for 18 hrs at 37° C. in LB with 0.2% arabinose and 100 μg/mL ampicillin. Cells were lysed by adding 75 mg/mL CELYTIC™ Express reagent (Cat. #C1990, Sigma Aldrich, St. Louis, Mo.) and incubating at 37° C. for 20 minutes. Inclusion body pellets were separated from lysed cell cultures by centrifugation at 9,000×g for 1 minute. Pellets were washed three times with $\frac{1}{3}^{rd}$ the original culture volume of 20 mM Tris-Cl, pH 8.0, and then resuspended in $\frac{1}{10}^{th}$ the original culture volume of 20 mM Tris-Cl, pH8.0.

Acid Hydrolysis of Peptide in Inclusion Body Pellets

Pellets were washed once and then resuspended in $\frac{1}{10}^{th}$ the original culture volume of sterile, filtered water. One mL of inclusion body suspension was pelleted by centrifugation at 9,000×g for 1 minute and then resuspended in 500 μL of 20 mM $H_2PO_4$, pH 2.2 (Cat. #0260-1, J. T. Baker, Phillipsburg, N.J.). A 100 μL time-zero sample was removed and neutralized by adding 50 μL of 100 mM MES, pH 8.9 (Cat. #475893, Calbiochem, La Jolla, Calif.). The remaining inclusion body sample was incubated at 65° C. Additional samples were taken at 2, 6 and 24 hours and neutralized in the same manner as the time-zero sample.

Separation of Hydrolyzed Peptide/Tag Fragments

25 μL of each neutralized sample was mixed with 75 μL 8 M guanidine-HCl (Cat. #5502UA, Life Technologies, Inc., Gaithersburg, Md.) and 25 μL of that mixture was injected onto a GraceVydacC18 HPLC column (Cat. #218TP54, Resolution Systems, Holland Mich.) run on an Agilent 1100 HPLC system (Agilent, Foster City, Calif.). Run conditions were 0.1% TFA in water and acetonitrile, gradient from 10-90% acetonitrile in 28 minutes, 0.35 mL/min, 40° C. Peak identities were confirmed by running fractions on denaturing acrylamide gels.

Analysis of HPLC Data

HPLC data was analyzed using ChemStation software (Hewlett Packard GmbH, Waldbrunn, Germany). Hydrolysis rates were determined by measuring the reduction in peak area for the unhydrolyzed peptide at each time point (FIG. 1).

Results and Conclusion

The rate of acid hydrolysis of the acid-labile linkers was based on the rate of disappearance of the corresponding parent fusion peptide (FIG. 1). Generally, each fusion peptide comprising more than one DP pair per linker was acid cleaved at a higher rate than the fusion peptide with one DP pair thereby indicating the relative rates of acid-cleavage demonstrated by the linkers of the present invention. In general, the rates of acid hydrolysis of the fusion peptides having the corresponding linkers follows the order DP4>DP3>DP2>DP.

Figure 2:
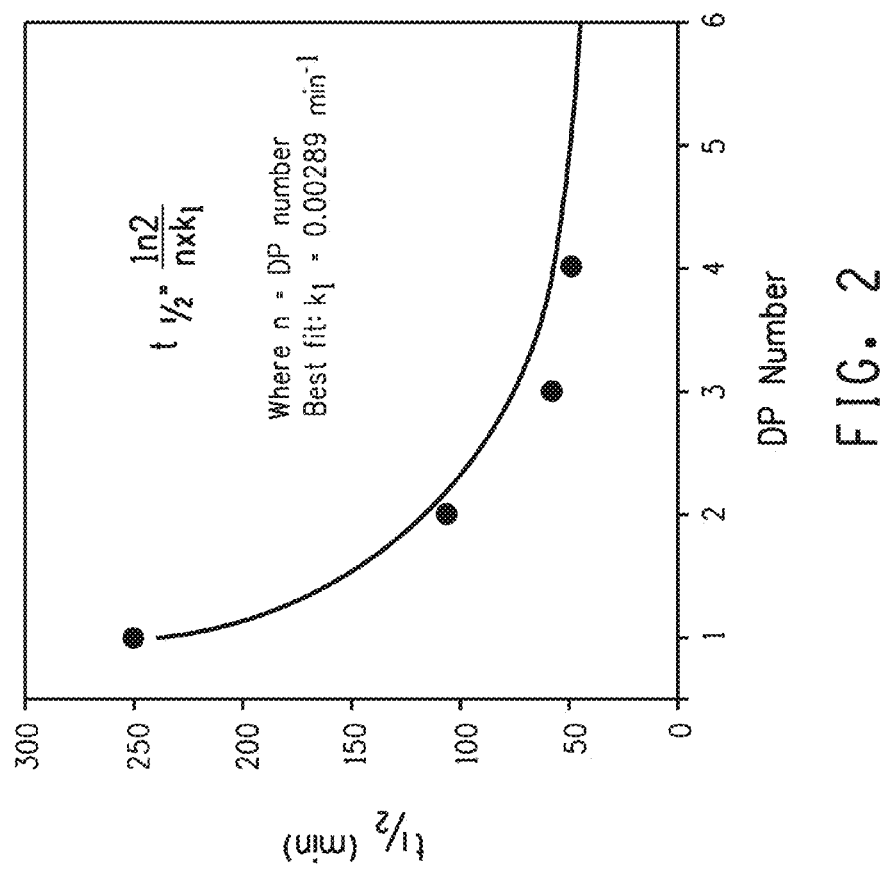
FIG. 2 shows a plot of the halftime, $t_{1/2}$, of acid hydrolysis performed at about 70° C. as a function of the number of DP pairs in the acid cleavable linker.

The rate of acid-cleavage of the fusion peptide can be modeled under this set of conditions as a simple linear combination of first order rate constants (FIG. 2). Decreasing the $t_{1/2}$ for hydrolysis can be accomplished by increasing the DP number.

In the experiments described in Example 4, linkers comprising three consecutive DP pairs, i.e. DP3, formed the core linker into which additional proline residues were introduced at various locations within the DP3 sequence. The introduction of one or more additional proline residues immediately after the proline of DP pair was predicated on the results of saturation mutagenesis experiments described in Example 3, and summarized in FIGS. 3 and 4. These experiments show that an additional proline added immediately after the proline of a single DP pair, provided enhanced fusion peptide hydrolysis rates.

Example 3

Effect of Saturation Mutagenesis at Amino Acid Positions Immediately Preceding or Following a Single DP Linker This Example demonstrates the effects of amino acid changes in the positions immediately upstream of the D residue in a single DP pair (i.e., the IBT side of the test fusion peptide) and downstream of the P residue in the single DP pair (i.e., the POI side of the test fusion peptide).

Construction of pINK101DP Variants Containing Amino Acid Changes on Either Side of DP Linker The strains and media follow those described in Example 2. Multiple changes were made to residues on either side of the DP linker in pINK101DP by site-directed mutagenesis using a QUIKCHANGE™ II Kit (Cat. #200524, Stratagene, La Jolla, Calif.). Reactions were thermocycled in a GeneAmp 9700 (Perkin Elmer Applied Biosystems, Norwalk, Conn.). The primers used to introduce changes are provided in Table 6 and the thermocycling program parameters are provided in Table 7. *Escherichia coli* BL21-A1 was transformed with 1 µL of QUIKCHANGE™ reaction product according to manufacturer's directions and transformants were selected on LB agar plates with 100 µg/mL ampicillin. In cases where no transformants were obtained (DP-Asp, DP-Glu, DP-Gly, DP-His, DP-Ile, DP-Leu, DP-Lys, DP-Met, DP-Pro, DP-Thr, DP-Trp), 2 µL of QUIKCHANGE™ reaction product was used to transform *E. coli* 10G Elite Electrocompetent Cells (Lucigen Corp., Middleton, Wis.) according to manufacturer's directions, for the purpose of generating super-coiled plasmid DNA. Transformants were selected on LB agar plates with 100 µg/mL ampicillin. DNA sequences were obtained for six isolates from each transformation in order to identify those with the desired mutations. Plasmid was prepared from the identified isolates using QIAprep Spin Miniprep Kit (QIAGEN Inc., Valencia, Calif.). *Escherichia coli* BL21-A1 was then transformed with 10 ng of plasmid DNA according to manufacturer's directions and transformants were selected on LB agar plates with 100 µg/mL ampicillin.

TABLE 6

Primers used to introduce modifications to residues flanking DP residues

| Primer ID | Nucleotide Sequence | SEQ ID NO: |
|---|---|---|
| DP1Alafor | CACCGGATCCATCGATCCAGCATT CCACGAAAACTGGCCGTC | 27 |
| DP1Alarev | GACGGCCAGTTTTCGTGGAATGCT GGATCGATGGATCCGGTG | 28 |
| DP1Asnfor | CACCGGATCCATCGATCCAAACTT CCACGAAAACTGGCCGTC | 29 |
| DP1Asnrev | GACGGCCAGTTTTCGTGGAAGTTT GGATCGATGGATCCGGTG | 30 |
| DP1Aspfor | CACCGGATCCATCGATCCAGATTT CCACGAAAACTGGCCGTC | 31 |
| DP1Asprev | GACGGCCAGTTTTCGTGGAAATCT GGATCGATGGATCCGGTG | 32 |
| DP1Cysfor | CACCGGATCCATCGATCCATTGTT CCACGAAAACTGGCCGTC | 33 |
| DP1Cysrev | GACGGCCAGTTTTCGTGGAACAAT GGATCGATGGATCCGGTG | 34 |
| DP1Glnfor | CACCGGATCCATCGATCCACAGTT CCACGAAAACTGGCCGTC | 35 |
| DP1Glnrev | GACGGCCAGTTTTCGTGGAACTGT GGATCGATGGATCCGGTG | 36 |
| DP1Glufor | CACCGGATCCATCGATCCAGAATT CCACGAAAACTGGCCGTC | 37 |
| DP1Glurev | GACGGCCAGTTTTCGTGGAATTCT GGATCGATGGATCCGGTG | 38 |
| DP1Glyfor | CACCGGATCCATCGATCCAGGATT CCACGAAAACTGGCCGTC | 39 |
| DP1Glyrev | GACGGCCAGTTTTCGTGGAATCCT GGATCGATGGATCCGGTG | 40 |
| DP1Hisfor | CACCGGATCCATCGATCCACACTT CCACGAAAACTGGCCGTC | 41 |
| DP1Hisrev | GACGGCCAGTTTTCGTGGAAGTGT GGATCGATGGATCCGGTG | 42 |
| DP1Ilefor | CACCGGATCCATCGATCCAATCTT CCACGAAAACTGGCCGTC | 43 |
| DP1Ilerev | GACGGCCAGTTTTCGTGGAAGATT GGATCGATGGATCCGGTG | 44 |
| DP1Leufor | CACCGGATCCATCGATCCACTCTT CCACGAAAACTGGCCGTC | 45 |
| DP1Leurev | GACGGCCAGTTTTCGTGGAAGAGT GGATCGATGGATCCGGTG | 46 |
| DP1Lysfor | CACCGGATCCATCGATCCAAAATT CCACGAAAACTGGCCGTC | 47 |
| DP1Lysrev | GACGGCCAGTTTTCGTGGAATTTT GGATCGATGGATCCGGTG | 48 |
| DP1Metfor | CACCGGATCCATCGATCCAATGTT CCACGAAAACTGGCCGTC | 49 |
| DP1Metrev | GACGGCCAGTTTTCGTGGAACATT GGATCGATGGATCCGGTG | 50 |
| DP1Phefor | CACCGGATCCATCGATCCATTCTT CCACGAAAACTGGCCGTC | 51 |

TABLE 6-continued

Primers used to introduce modifications to residues flanking DP residues

| Primer ID | Nucleotide Sequence | SEQ ID NO: |
|---|---|---|
| DP1Pherev | GACGGCCAGTTTTCGTGGAAGAATGGATCGATGGATCCGGTG | 52 |
| DP1Profor | CACCGGATCCATCGATCCACCATTCCACGAAAACTGGCCGTC | 53 |
| DP1Prorev | GACGGCCAGTTTTCGTGGAATGGTGGATCGATGGATCCGGTG | 54 |
| DP1Serfor | CACCGGATCCATCGATCCATCCTTCCACGAAAACTGGCCGTC | 55 |
| DP1Serrev | GACGGCCAGTTTTCGTGGAAGGATGGATCGATGGATCCGGTG | 56 |
| DP1Thrfor | CACCGGATCCATCGATCCAACCTTCCACGAAAACTGGCCGTC | 57 |
| DP1Thrrev | GACGGCCAGTTTTCGTGGAAGGTTGGATCGATGGATCCGGTG | 58 |
| DP1Trpfor | CACCGGATCCATCGATCCATGGTTCCACGAAAACTGGCCGTC | 59 |
| DP1Trprev | GACGGCCAGTTTTCGTGGAACCATGGATCGATGGATCCGGTG | 60 |
| DP1Tyrfor | CACCGGATCCATCGATCCATACTTCCACGAAAACTGGCCGTC | 61 |
| DP1Tyrrev | GACGGCCAGTTTTCGTGGAAGTATGGATCGATGGATCCGGTG | 62 |
| DP1Valfor | CACCGGATCCATCGATCCAGTTTTCCACGAAAACTGGCCGTC | 63 |
| DP1Valrev | GACGGCCAGTTTTCGTGGAAAACTGGATCGATGGATCCGGTG | 64 |
| AlaDP1for | CCCCTTCACCGGATCCGCGATCCACGTTTCCACGAAAAC | 65 |
| ArgDP1for | CCCCTTCACCGGATCCCGTGATCCACGTTTCCACGAAAAC | 66 |
| AsnDP1for | CCCCTTCACCGGATCCAACGATCCACGTTTCCACGAAAAC | 67 |
| AspDP1for | CCCCTTCACCGGATCCGATGATCCACGTTTCCACGAAAAC | 68 |
| CysDP1for | CCCCTTCACCGGATCCTTGGATCCACGTTTCCACGAAAAC | 69 |
| GlnDP1for | CCCCTTCACCGGATCCCAGGATCCACGTTTCCACGAAAAC | 70 |
| GluDP1for | CCCCTTCACCGGATCCGAGGATCCACGTTTCCACGAAAAC | 71 |
| GlyDP1for | CCCCTTCACCGGATCCGGAGATCCACGTTTCCACGAAAAC | 72 |
| HisDP1for | CCCCTTCACCGGATCCCACGATCCACGTTTCCACGAAAAC | 73 |
| LeuDP1for | CCCCTTCACCGGATCCCTCGATCCACGTTTCCACGAAAAC | 74 |
| LysDP1for | CCCCTTCACCGGATCCAAAGATCCACGTTTCCACGAAAAC | 75 |
| MetDP1for | CCCCTTCACCGGATCCATGGATCCACGTTTCCACGAAAAC | 76 |
| PheDP1for | CCCCTTCACCGGATCCTTCGATCCACGTTTCCACGAAAAC | 77 |
| ProDP1for | CCCCTTCACCGGATCCCCAGATCCACGTTTCCACGAAAAC | 78 |
| SerDP1for | CCCCTTCACCGGATCCTCCGATCCACGTTTCCACGAAAAC | 79 |
| ThrDP1for | CCCCTTCACCGGATCCACCGATCCACGTTTCCACGAAAAC | 80 |
| TrpDP1for | CCCCTTCACCGGATCCTGGGATCCACGTTTCCACGAAAAC | 81 |
| TyrDP1for | CCCCTTCACCGGATCCTACGATCCACGTTTCCACGAAAAC | 82 |
| ValDP1for | CCCCTTCACCGGATCCGTTGATCCACGTTTCCACGAAAAC | 83 |
| AlaDP1rev | GTTTTCGTGGAAACGTGGATCGGCGGATCCGGTGAAGGGG | 84 |
| ArgDP1rev | GTTTTCGTGGAAACGTGGATCACGGGATCCGGTGAAGGGG | 85 |
| AsnDP1rev | GTTTTCGTGGAAACGTGGATCGTTGGATCCGGTGAAGGGG | 86 |
| AspDP1rev | GTTTTCGTGGAAACGTGGATCATCGGATCCGGTGAAGGGG | 87 |
| CysDP1rev | GTTTTCGTGGAAACGTGGATCCAAGGATCCGGTGAAGGGG | 88 |
| GlnDP1rev | GTTTTCGTGGAAACGTGGATCCTGGGATCCGGTGAAGGGG | 89 |
| GluDP1rev | GTTTTCGTGGAAACGTGGATCTTCGGATCCGGTGAAGGGG | 90 |
| GlyDP1rev | GTTTTCGTGGAAACGTGGATCTCCGGATCCGGTGAAGGGG | 91 |
| HisDP1rev | GTTTTCGTGGAAACGTGGATCGTGGGATCCGGTGAAGGGG | 92 |
| LeuDP1rev | GTTTTCGTGGAAACGTGGATCGAGGGATCCGGTGAAGGGG | 93 |
| LysDP1rev | GTTTTCGTGGAAACGTGGATCTTTGGATCCGGTGAAGGGG | 94 |
| MetDP1rev | GTTTTCGTGGAAACGTGGATCCATGGATCCGGTGAAGGGG | 95 |
| PheDP1rev | GTTTTCGTGGAAACGTGGATCGAAGGATCCGGTGAAGGGG | 96 |
| ProDP1rev | GTTTTCGTGGAAACGTGGATCTGGGGATCCGGTGAAGGGG | 97 |
| SerDP1rev | GTTTTCGTGGAAACGTGGATCGGAGGATCCGGTGAAGGGG | 98 |
| ThrDP1rev | GTTTTCGTGGAAACGTGGATCGGTGGATCCGGTGAAGGGG | 99 |
| TrpDP1rev | GTTTTCGTGGAAACGTGGATCCCAGGATCCGGTGAAGGGG | 100 |
| TyrDP1rev | GTTTTCGTGGAAACGTGGATCGTAGGATCCGGTGAAGGGG | 101 |

TABLE 6-continued

Primers used to introduce modifications to
residues flanking DP residues

| Primer ID | Nucleotide Sequence | SEQ ID NO: |
|---|---|---|
| ValDP1rev | GTTTTCGTGGAAACGTGGATCAAC GGATCCGGTGAAGGGG | 102 |

PCR Reaction components

| 10X QUIKCHANGE ® reaction buffer | 5 μL |
|---|---|
| QUIKCHANGE ™ dNTP mix | 1 μL |
| Pfu polymerase | 1 μL |
| 10 μM forward primer | 1 μL |
| 10 μM reverse primer | 1 μL |
| Water | 40 μL |

TABLE 7

Thermocycling program parameters

| Segment | Cycles | Temperature | Time |
|---|---|---|---|
| 1 | 1 | 95° C. | 30 seconds |
| 2 | 25 | 95° C. | 30 seconds |
|  |  | 55° C. | 1 minute |
|  |  | 68° C. | 6 minutes |
| 3 | 1 | 68° C. | 8 minutes |
| 4 | 1 | 4° C. | hold |

Preparation of Peptide-Containing Inclusion Bodies

The preparation of peptide-containing inclusion bodies followed the procedures described in Example 2.

Acid Hydrolysis of Peptide in Inclusion Body Pellets

Pellets were washed once and then resuspended in $\frac{1}{10}^{th}$ the original culture volume of sterile, filtered water. 300 μL of inclusion body suspension was pelleted by centrifugation at 9,000×g for 1 minute and then resuspended in 130 μL of 20 mM $H_2PO_4$, pH 2.2 (Cat. #0260-1, J. T. Baker, Phillipsburg, N.J.). A 40-μL time-zero sample was removed and neutralized by adding 20 μL of 100 mM MES, pH 8.9 (Cat. #475893, Calbiochem, La Jolla, Calif.). The remaining inclusion body sample was incubated at 70° C. Additional samples were taken at 2 and 6 hours and neutralized in the same manner as the time-zero sample.

Separation of Hydrolyzed Peptide/Tag Fragments and HPLC Analysis

The hydrolyzed peptide/solubility tag fragments were separated using the process described in Example 2. HPLC analysis was conducted as described in Example 2.

Results and Conclusion

The rate of hydrolysis was minimally affected by the majority of amino acid changes immediately preceding the D residue of the DP pair in the linker although proline in this position marginally enhanced the hydrolysis rate (FIG. 3). Substitution of tryptophan or phenylalanine for isoleucine on the amino-terminal side of the DP linker significantly slows the rate of acid hydrolysis (FIG. 3). As such, substituting tryptophan or phenylalanine on the amino-terminal side of the DP linker may be useful to increase the stability of the DP linker in applications where acid cleavage of a DP pair is not desired (e.g., a DP linker is present in a protein or peptide of interest where acid cleavage is not desired).

An unexpected result was that only the substitution of proline for arginine at the position immediately following the proline residue of the DP linker substantially increases the rate of acid hydrolysis (FIG. 4). Therefore, the effect on acid hydrolysis rates of additional proline residues inserted upon a DP3 background was assessed.

Example 4

Effect of Introducing Additional Proline Residues to the DPDPDP Linker

Based on the conclusion from Example 3, that an additional proline on the C-terminal side of the single DP linker further accelerates the rate of hydrolysis, one or two prolines were added to an analogous position within the DP3 linker. Example 4 demonstrates the effect on acid hydrolysis rate of the test fusion peptide of adding proline residues to the DPD-PDP linker (SEQ ID NO:2). These derivatives of DP3 are referred to as PP1, PP2, PP3 and PP4 (see Table 2 for sequences).

The strain, growth media, and construction of expression plasmid pDP3 is described in Example 2.

Construction of pDP3 Variants Containing Additional Proline Residues in the DP3 Linker Additional proline residues were introduces at various positions in the DP3 linker by site-directed mutagenesis using a QUIKCHANGE™ II Kit (Cat. #200524, Stratagene, La Jolla, Calif.). The primers used to prepare the corresponding variants are shown in Table 8. Reactions were thermocycled in a Gene Amp 9700 (Perkin Elmer Cetus, Norwalk, Conn.). The PCR reaction components and the thermocycling program parameters follow those described in Example 3. *Escherichia coli* BL21-A1 was transformed with 1 μL of QUIKCHANGE™ reaction product according to manufacturer's directions and transformants were selected on LB agar plates with 100 μg/mL ampicillin. Transformants with the desired mutations were identified by DNA sequencing. In the case of PP4, no transformants were obtained and the transformation was repeated using *E. coli* 10G Elite Electrocompetent Cells as described in Example 3.

TABLE 8

Primers used in the construction of DP3 variants

| Primer ID | Nucleotide Sequence | SEQ ID NO: |
|---|---|---|
| DPDPDPPfor "PP1" | CATCGATCCAGATCCAGATCCACCACGTTT CCACGAAAACTGGCC | 104 |
| DPDPDPPrev "PP1" | GGCCAGTTTTCGTGGAAACGTGGTGGATC TGGATCTGGATCGATG | 105 |
| DPDPPDPPfor "PP2" | CATCGATCCAGATCCACCAGATCCACCAC GTTTCCACGAAAACTGGCC | 106 |
| DPDPPDPPrev "PP2" | GCCAGTTTTCGTGGAAACGTGGTGGATCT GGTGGATCTGGATCGATG | 107 |
| DPDPPDPfor "PP3" | GATCCATCGATCCAGATCCACCAGATCCAC GTTTCCACGAAAAC | 108 |
| DPDPPDPrev "PP3" | GTTTTCGTGGAAACGTGGATCTGGTGGAT CTGGATCGATGGATC | 109 |
| DPPDPPDPfor "PP4" | CACCGGATCCATCGATCCACCAGATCCAC CAGATCCACGTTTCCACGAAAAC | 110 |

TABLE 8-continued

Primers used in the construction of DP3 variants

| Primer ID | Nucleotide Sequence | SEQ ID NO: |
|---|---|---|
| DPPDPPDPrev "PP4" | GTTTTCGTGGAAACGTGGATCTGGTGGAT CTGGTGGATCGATGGATCCGGTG | 111 |

Preparation of Peptide-Containing Inclusion Bodies

The preparation of the peptide-containing inclusion bodies follows the procedures described in Example 2.

Acid Hydrolysis of Peptide in Inclusion Body Pellets

Pellets were washed once and then resuspended in $\frac{1}{10}^{th}$ the original culture volume of sterile, filtered water. For PP1, 250 µL of inclusion body suspension was pelleted by centrifugation at 9,000×g for 1 minute and then resuspended in 120 µL of 20 mM $H_2PO_4$. For PP2, PP3, and PP4, 500 µL of inclusion body suspension was pelleted by centrifugation at 9,000×g for 1 minute and then resuspended in 120 µL of 20 mM $H_2PO_4$, pH 2.2 (Cat. #0260-1, J. T. Baker, Phillipsburg, N.J.). A 20 µL time-zero sample was removed and neutralized by adding 10 µL of 100 mM MES, pH 8.9 (Cat. #475893, Calbiochem, La Jolla, Calif.). The remaining inclusion body sample was incubated at 70° C. Additional samples were taken at 0.5, 1, 2 4 hours and neutralized in the same manner as the time-zero sample.

Separation of Hydrolyzed Peptide/Tag Fragments and HPLC Analysis

The hydrolyzed peptide/solubility tag fragments were separated using the process described in Example 2. HPLC analysis was conducted as described in Example 2.

Results and Conclusion

Figure 5:
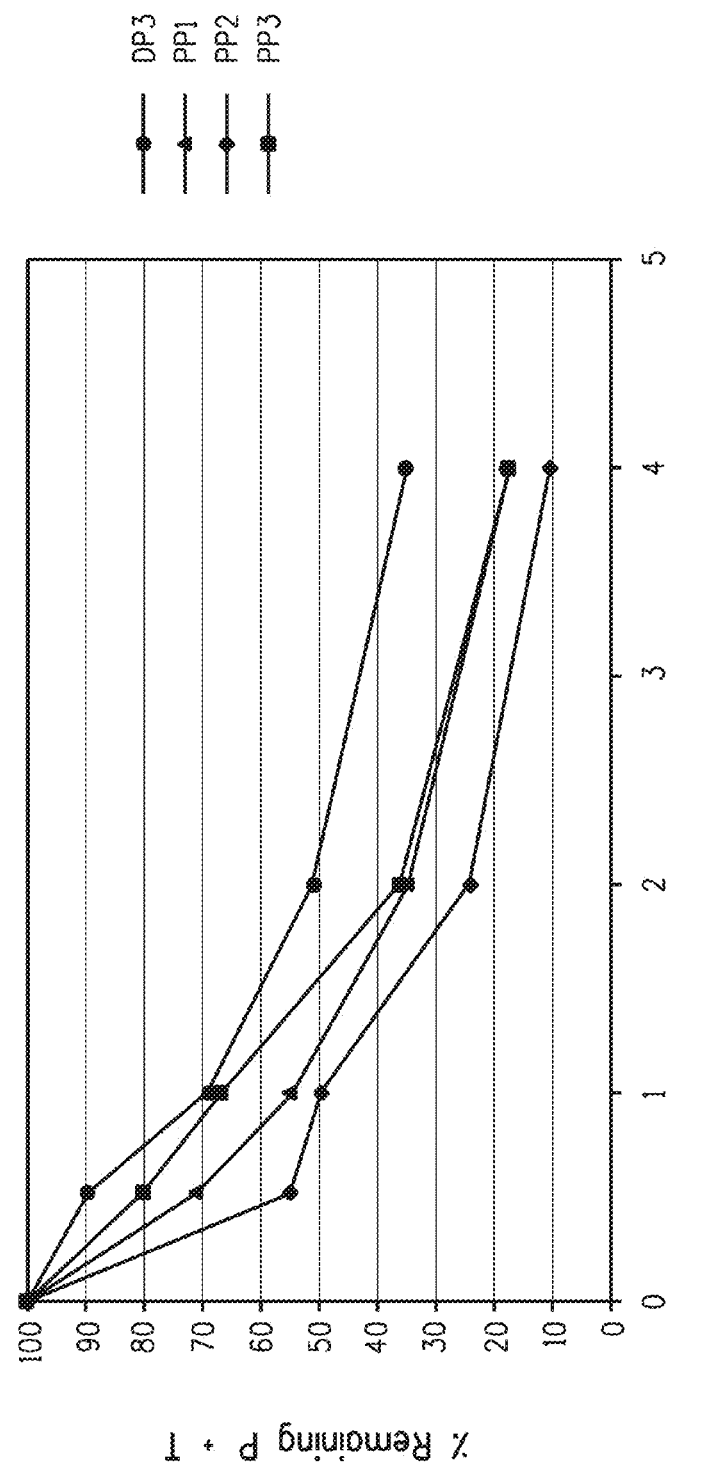
FIG. 5 demonstrates the effect on rates of acid hydrolysis of an intact fusion peptide of having additional proline residues included in the acid cleavable linker "DP3"; DP3 (SEQ ID NO: 2), PP1 (SEQ ID NO: 4), PP2 (SEQ ID NO: 5) and PP3 (SEQ ID NO: 6).
Figure 6:
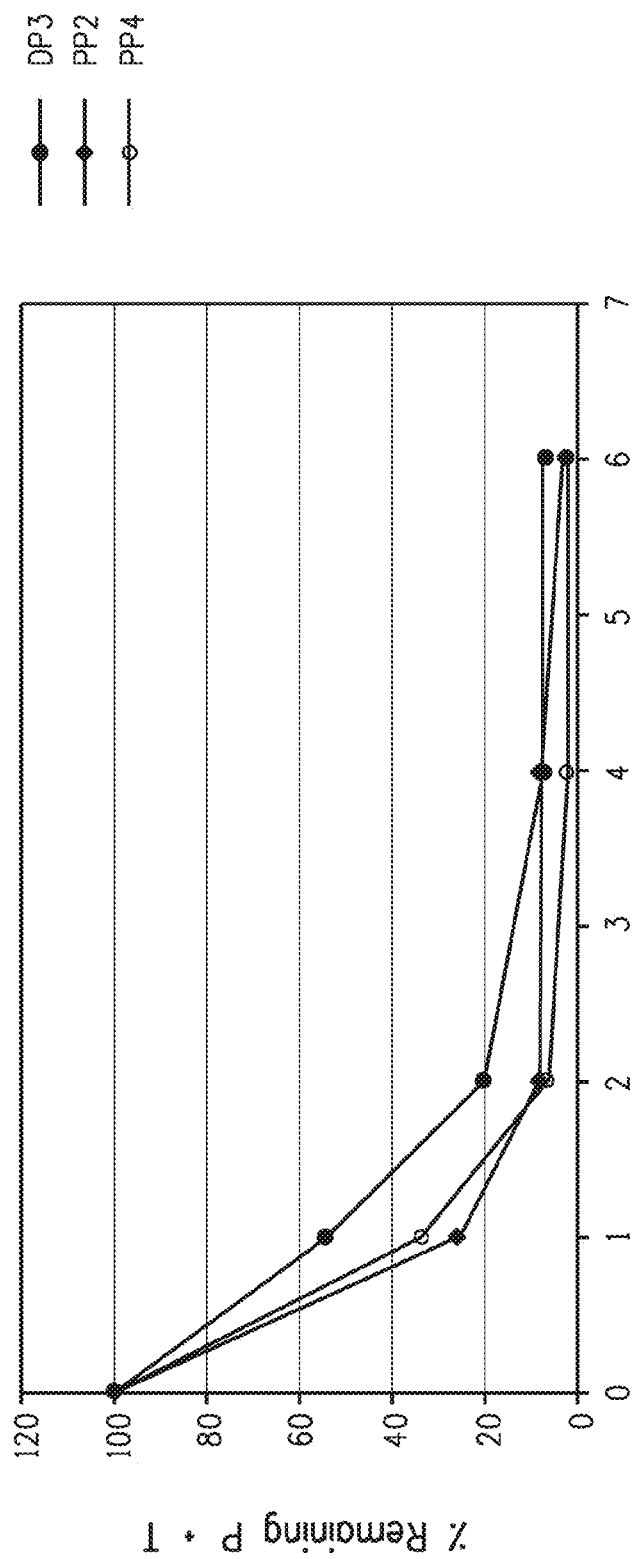
FIG. 6 demonstrates the effect on rates of acid hydrolysis of an intact fusion peptide of placing additional proline residues within the acid cleavable linker "DP3"; DP3 (SEQ ID NO: 2), PP2 (SEQ ID NO: 5) and PP4 (SEQ ID NO: 7). See Table 2 for each corresponding linker sequence.

The rate of hydrolysis is increased by the addition of proline residues to the DP3 linker, with PP2 and PP4 showing the highest rate of acid-cleavage (FIGS. 5 and 6).

Example 5

Effect of pH and Temperature on Acid Hydrolysis

The following example was conducted to demonstrate the effect of changes in pH and temperature on the rate of acid hydrolysis on various DP linkers.

Strains and Media

Strains are described in Examples 2 and 4, media and growth conditions in Example 2.

Preparation of Peptide-Containing Inclusion Bodies

The preparation of the peptide-containing inclusion bodies follows the procedures described in Example 2.

Acid Hydrolysis of Peptide in Inclusion Body Pellets (Varying pH)

Figure 7:
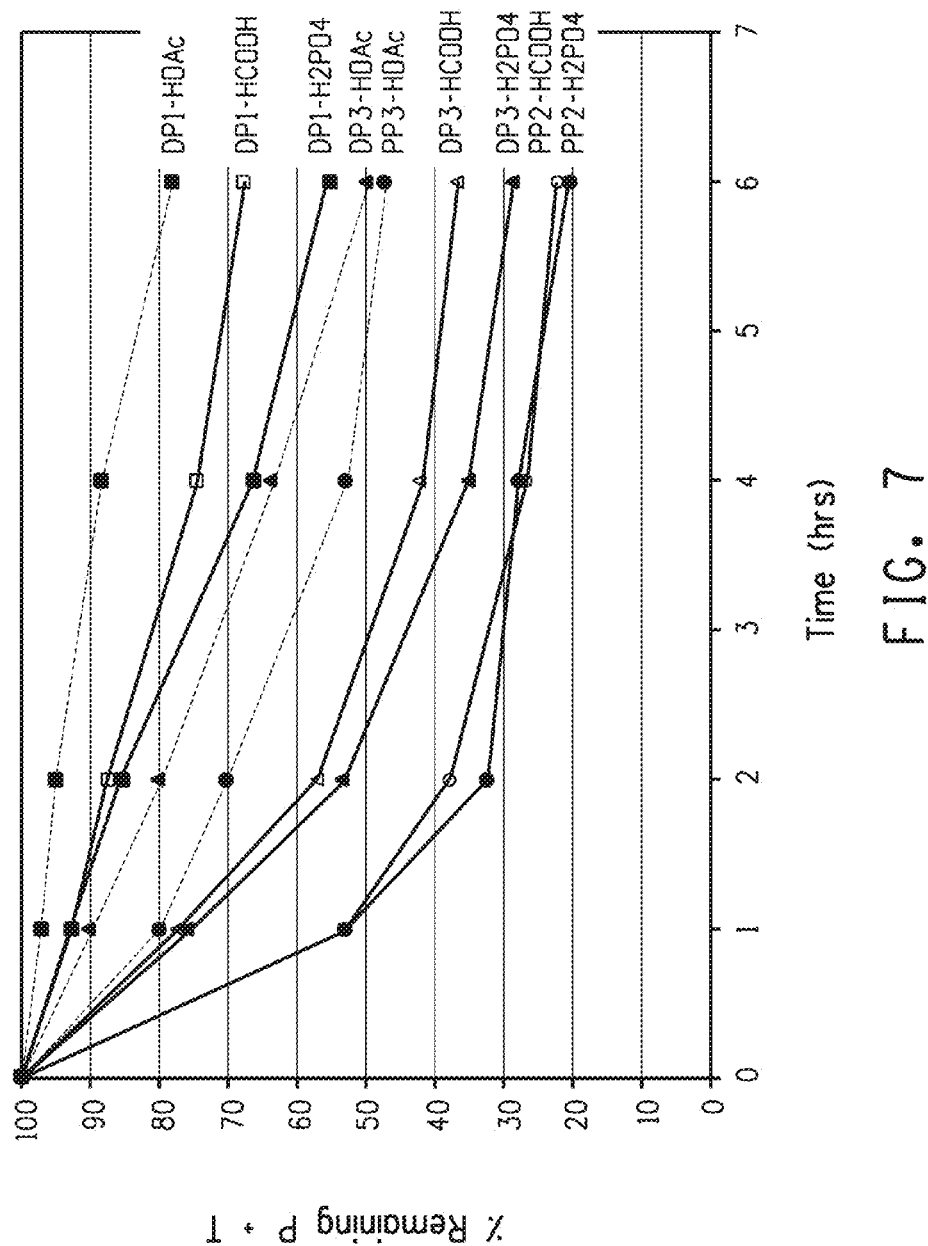
FIG. 7 demonstrates the effect of different acidic conditions on the rate of acid hydrolysis of an intact fusion peptide comprising the acid cleavable linker DP1, DP3, PP2 or PP3 (SEQ ID NO: 5) at approximately 70° C. See Table 2 for each corresponding linker sequence.

Pellets were washed once and then resuspended in $\frac{1}{10}^{th}$ the original culture volume of sterile, filtered water. For DP1, DP3, and PP2; 580 µL, 290 µL, and 720 µL of inclusion body suspension, respectively, was pelleted by centrifugation at 9,000×g for 1 minute and then resuspended in 360 µL of sterile, filtered water. Each sample was divided into three 120 µL aliquots and then re-pelleted by centrifugation at 9,000×g for 1 minute. For each sample, one of the three aliquots was resuspended in 0.25% phosphoric acid, pH 2.10 (Cat. #0260-1, J. T. Baker, Phillipsburg, N.J.), 0.25% formic acid, pH 2.44 (Cat. #FX0440-7, E. M. Science, Gibbstown, N.J.) or 0.25% acetic acid, pH 2.88 (Cat. #AX0073-6, EMD Chemicals, Gibbstown, N.J.). A 20 µL time-zero sample was removed from each and neutralized by adding 10 µL of 100 mM MES, pH 8.9 (Cat. #475893, Calbiochem, La Jolla, Calif.). The remaining inclusion body sample was incubated at 70° C. Additional samples were taken at 1, 2, 4 and 6 hours and neutralized in the same manner as the time-zero sample. The results are provided in FIG. 7.

Acid Hydrolysis of Peptide in Inclusion Body Pellets (Reduced Temperature)

Pellets were washed once and then resuspended in $\frac{1}{10}^{th}$ the original culture volume of sterile, filtered water. For DP3 and PP2, 240 µL and 450 µL of inclusion body suspension, respectively, was pelleted by centrifugation at 9,000×g for 1 minute and then resuspended in 240 µL of sterile, filtered water. Each sample was divided into two 120 µL aliquots and then re-pelleted by centrifugation at 9,000×g for 1 minute. For each sample, one of the two aliquots was resuspended in 0.25% phosphoric acid, pH 2.10 (Cat. #0260-1, J. T. Baker, Phillipsburg, N.J.) or 0.25% formic acid, pH 2.44 (Cat. #FX0440-7, E. M. Science, Gibbstown, N.J.). A 20 µL time-zero sample was removed from each and neutralized by adding 10 µL of 100 mM MES, pH 8.9 (Cat. #475893, Calbiochem, La Jolla, Calif.). The remaining inclusion body sample was incubated at 50° C. Additional samples were taken at 1, 2, 6 and 24 hours and neutralized in the same manner as the time-zero sample. The results are provided in FIG. 8.

Separation of Hydrolyzed Peptide/Tag Fragments and HPLC Analysis

The hydrolyzed peptide/solubility tag fragments were separated using the process described in Example 2. HPLC analysis was conducted as described in Example 2.

Results and Conclusion

Figure 8:
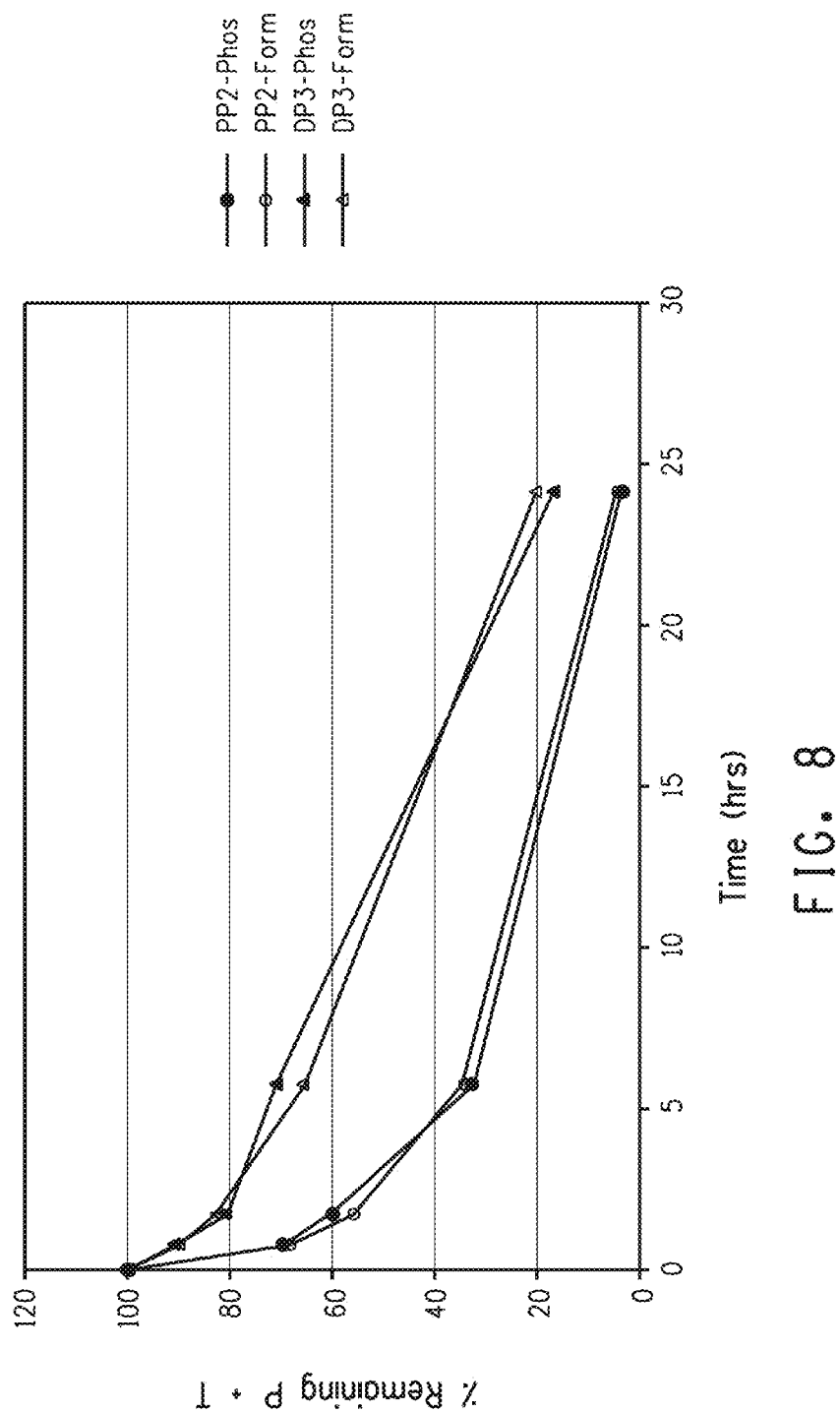
FIG. 8 demonstrates the effect of different acidic conditions on the rate of acid hydrolysis of an intact fusion peptide having either the acid cleavable linker DP3 (SEQ ID NO: 2) or PP2 (SEQ ID NO: 5) at reduced temperature of 50° C. See Table 2 for each corresponding linker sequence.
Figure 9:
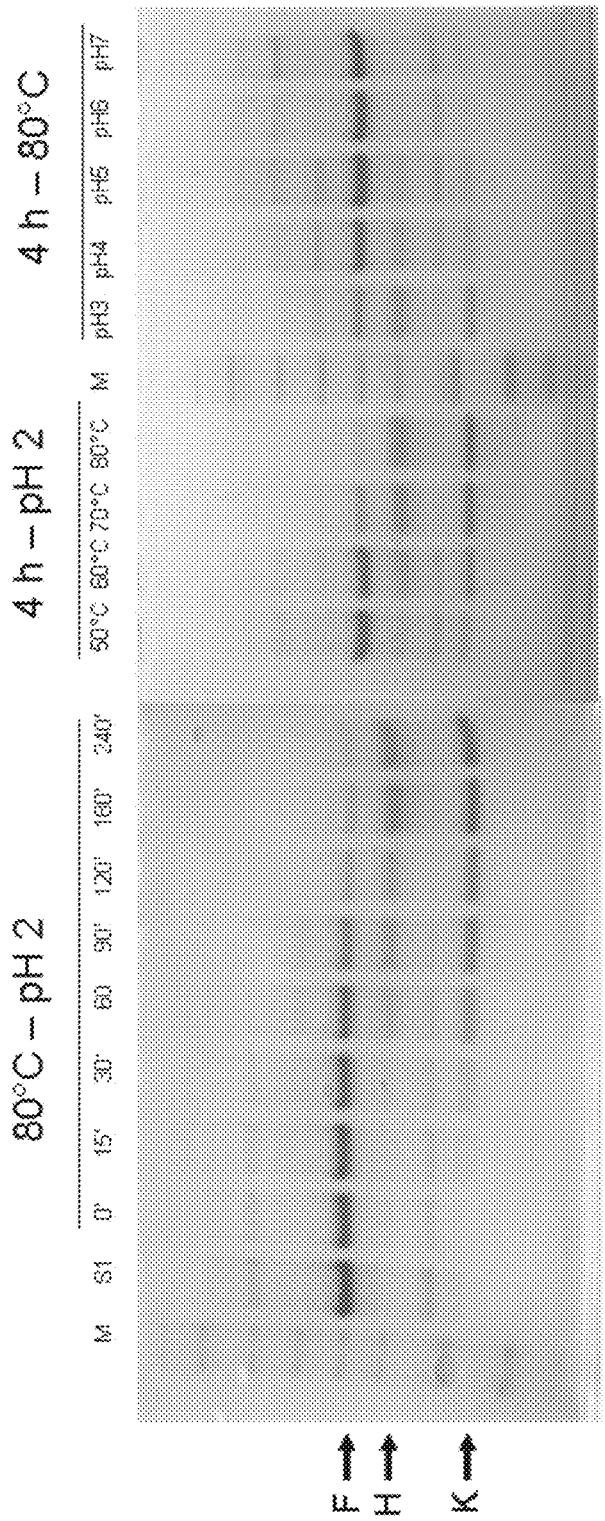
FIG. 9 demonstrates the effect of different acidic conditions on the extent of acid hydrolysis of an intact fusion peptide KSI(C4E).DP.HC353 having the acid cleavable linker DP. Maximum cleavage is obtained after 4 h at pH 2 and 80° C. Arrows indicate the full length fusion (F), HC353 (H) and KSI(C4E) (K).
Figure 10:
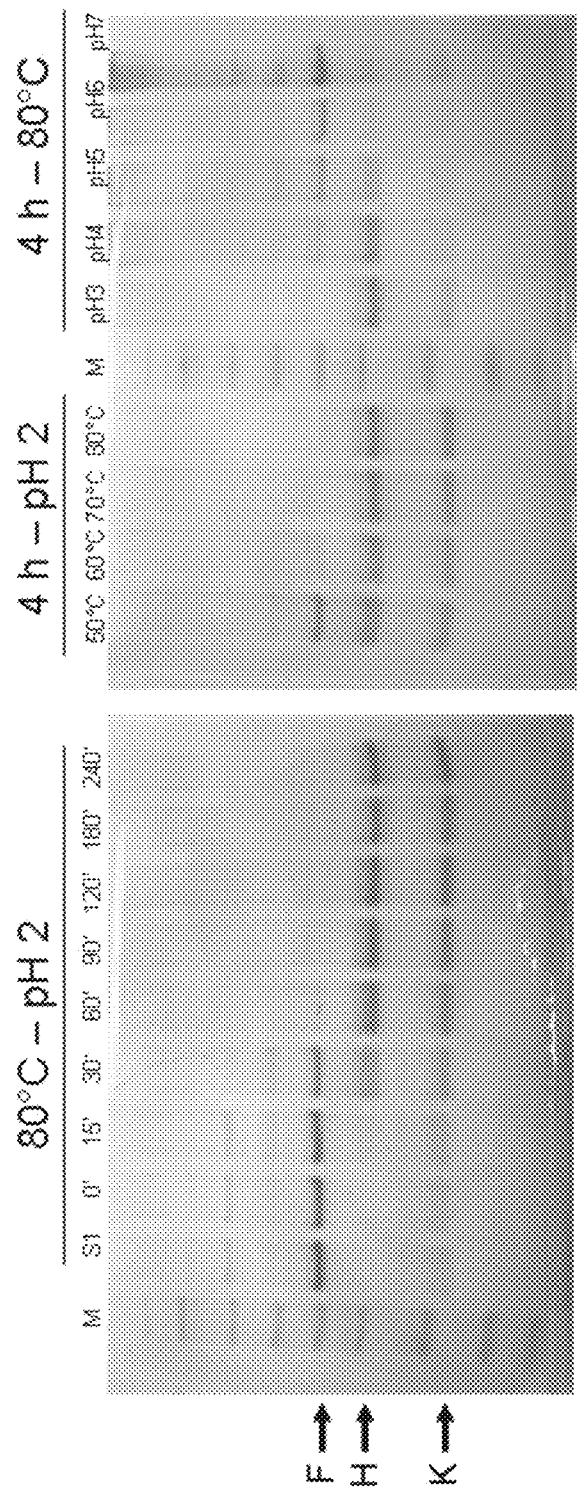
FIG. 10 demonstrates the effect of different acidic conditions on the extent of acid hydrolysis of an intact fusion peptide KSI(C4E).DPDPPDPP.HC353 having the acid cleavable linker DPDPPDPP. Maximum cleavage is obtained after only 1 h at pH 2 and 80° C., at 60° C. for 4 h at pH 2 or at pH 4 for 4 hr and at 80° C. Arrows indicate the full length fusion (F), HC353 (H) and KSI(C4E) (K).
Figure 11:
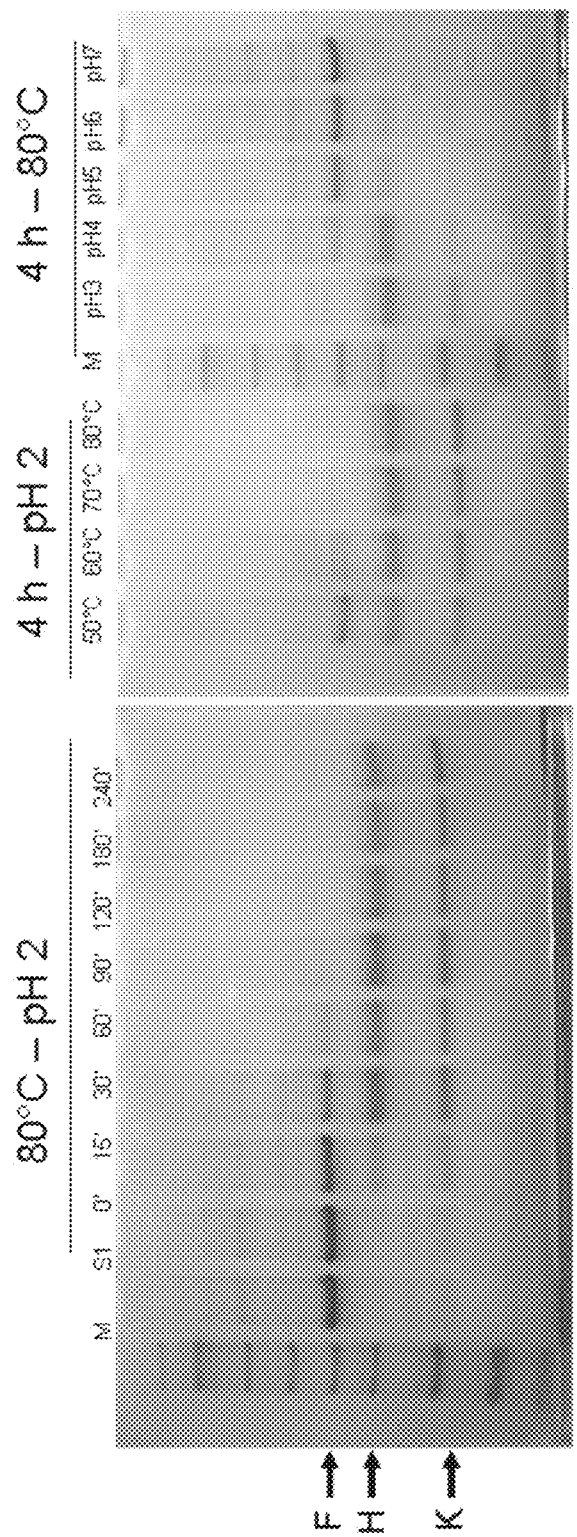
FIG. 11 demonstrates the effect of different acidic conditions on the extent of acid hydrolysis of an intact fusion peptide KSI(C4E).DPPDPPDP.HC353 having the acid cleavable linker DPPDPPDP. Maximum cleavage is obtained after only 90 min 4 h at pH 2 and 80° C., at 70° C. for 4 h at pH 2 or at pH 3 for 4 h and at 80° C. Arrows indicate the full length fusion (F), HC353 (H) and KSI(C4E) (K).
Figure 12:
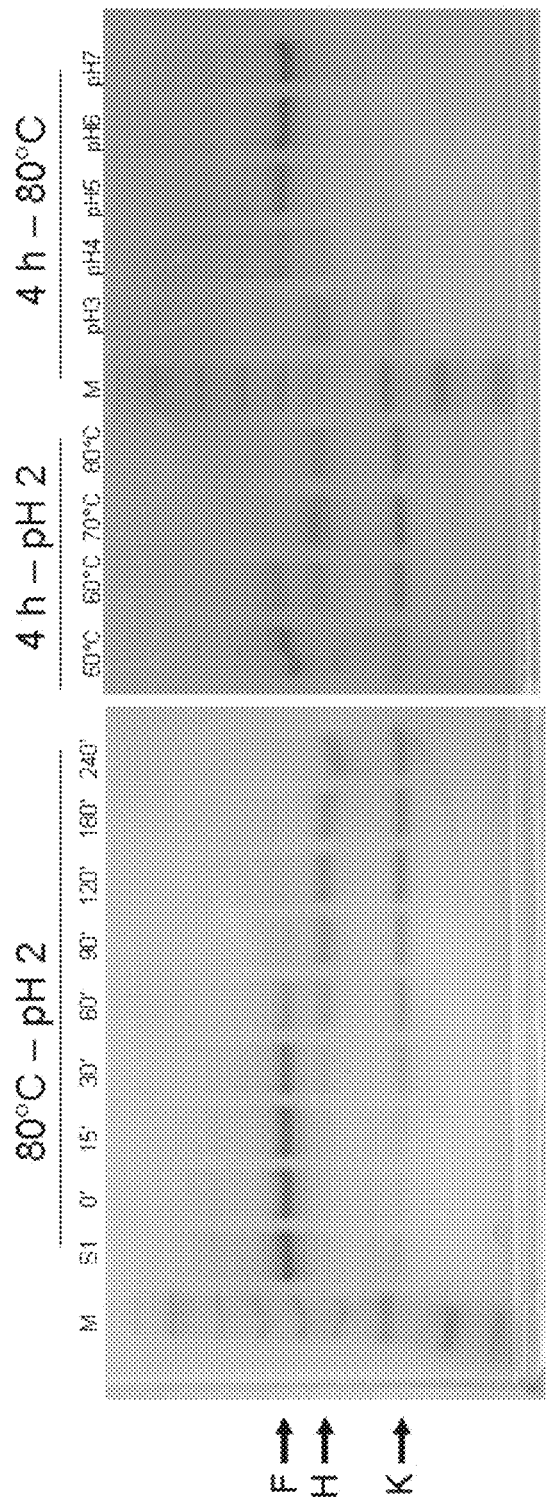
FIG. 12 demonstrates the effect of different acidic conditions on the extent of acid hydrolysis of an intact fusion peptide KSI(C4E).DPDPDP.HC353 having the acid cleavable linker DPDPDP. Maximum cleavage is obtained after only 120 min 4 h at pH 2 and 80° C., at 70° C. for 4 h at pH 2 or at pH 3 for 4 h and at 80° C. Arrows indicate the full length fusion (F), HC353 (H) and KSI(C4E) (K).

The results of hydrolysis in 0.25% w/v acid solutions at 70° C. (FIG. 7) and 50° C. are illustrated (FIG. 8).

The relative hydrolysis rate in formic acid, pH 2.44, was not substantially different from phosphoric acid, pH 2.10 for either DP3 or PP2 at either 70° C. (FIG. 7) or 50° C. However, the hydrolysis rate at 50° C. was reduced approximately 2-fold for PP2 and 3-fold for DP3 as compared to the rate at 70° C.

Example 6

Preparation of Constructs Incorporating Different Acid Labile Sequences

This example describes the assembly of four constructs that contain different acid-labile sequences that separate the two domains of the protein. The fusion peptides were designed to have an inclusion body tag (KSI(C4E); SEQ ID NO: 252) linked to a peptide of interest (HC353; SEQ ID NO: 253) where the two components are separated by an acid-cleavable peptide linker. The following four acid-cleavable linkers were engineered between KSI(C4E) and HC353:

```
DP
DPDPDP          (SEQ ID NO: 2)
DPDPPDPP        (SEQ ID NO: 5)
DPPDPPDP        (SEQ ID NO: 7)
```

Construction of KSI(C4E).DP.HC353:

The gene for HC353 was synthesized by DNA2.0 (Menlo Park, Calif.) with BamHI and AscI flanking the 5' and 3' ends of the gene, respectively. The gene incorporated nucleotides that code for the amino acid sequence DP just downstream of the BamHI site. The HC353 gene was cloned into the BamHI-AscI sites of the plasmid pLD001 (SEQ ID NO: 254), yielding plasmid pJZ353.

The resulting DNA construct (SEQ ID NO: 255) encoded the fusion peptide KSI(C4E).DP.HC353 (SEQ ID NO: 256).

Construction of KSI(C4E).DPDPDP.HC353:

In order to modify the acid-cleavable linker between KSI (C4E) and HC353, two additional DP sequences were incorporated into the sequence encoding KSI(C4E).DP.HC353. This was accomplished by the QuikChange Site-Directed Mutagenesis kit by Stratagene (La Jolla, Calif.). The following two primers were used to introduce the additional sequences:

353.DP3 UP:
(SEQ ID NO: 257)
gcttgtcagggatccgatcctgaccctgatccatctgctcaatctcaa
ctgcc 353.DP3 DOWN:
(SEQ ID NO: 258)
ggcagttgagattgagcagatggatcagggtcaggatcggatccctga
caagc The resulting plasmid pLR688 expressed a DNA construct (SEQ ID NO: 259) encoding fusion peptide KSI(C4E).DPD-PDP.HC353 (SEQ ID NO: 260).

Construction of KSI(C4E).DPDPPDPP.HC353:

In order to modify the acid-cleavable linker between KSI (C4E) and HC353, two additional P residues were incorporated into the sequence encoding KSI(C4E).DPDPD-P.HC353 (pLR688). This was accomplished by the QuikChange Site-Directed Mutagenesis kit by Stratagene (La Jolla, Calif.). The following two primers were used to introduce the additional sequences:

PP2 HC353 UP:
(SEQ ID NO: 261)
gatccgatcctgaccctccagatccaccgtctgctcaatctcaactgc

PP2 HC353 DOWN:
(SEQ ID NO: 262)
gcagttgagattgagcagacggtggatctggagggtcaggatcggatc The resulting plasmid pLR726 expressed a DNA construct (SEQ ID NO: 263) encoding fusion peptide KSI(C4E).DPD-PPDPP.HC353 (SEQ ID NO: 264).

Construction of KSI(C4E).DPPDPPDP.HC353:

In order to modify the acid-cleavable linker between KSI (C4E) and HC353, two additional P residues were incorporated into the sequence encoding KSI(C4E).DPDPD-P.HC353 (pLR688). This was accomplished by the QuikChange Site-Directed Mutagenesis kit by Stratagene (La Jolla, Calif.). The following two primers were used to introduce the additional sequences:

353 PP4 UP:
(SEQ ID NO: 265)
gtcagggatccgatcctccagaccctccagatccatctgctcaatc

353 PP4 DOWN:
(SEQ ID NO: 266)
gattgagcagatggatctggagggtctggaggatcggatccctgac

The resulting plasmid pLR816 expressed a DNA construct (SEQ ID NO: 267) encoding fusion peptide KSI(C4E).DPP-DPPDP.HC353 (SEQ ID NO: 268).

Example 7

Production of IBT Fusions to Peptides HC353

Strains expressing the fusions of KSI(C4E) to peptide HC353 with variants of the DP acid cleavage described in Example 6 were grown in one liter of autoinduction medium (10 g/L Tryptone, 5 g/L Yeast Extract, 5 g/L NaCl, 50 mM $Na_2HPO_4$, 50 mM $KH_2PO_4$, 25 mM $(NH_4)_2SO_4$, 3 mM $MgSO_4$, 0.75% glycerol, 0.075% glucose and 0.05% arabinose, 50 mg/mL Spectinomycin) at 37° C., and 200 rpm incubator shaker for 20 hours. The cells were harvested by centrifugation, resuspended in 200 mL of lysis buffer (50 mM Tris pH 7.5, 5 mM EDTA, 100 mM NaCl) using a tissue homogenizer (Brinkman Homogenizer model PCU11 at setting 3-4) and collected again by centrifugation at 8000 rpm for 5 min. The washed cells were resuspended with a homogenizer in 200 mL of lysis buffer to the pellet containing 50 mg of lysozyme and allowed to sit on ice for three hours before being frozen at −20° C. The cell suspension was thawed at 37° C., homogenized and subject to sonication using a Branson Sonifier model 450 sonicator equipped with a 5 mm probe (Branson Ultrasonics Corporation, Danbury, Conn.) at 20% maximum output, 2 pulses per second for 1 min, repeat once.

The disrupted cells were transferred to 50-mL conical tubes and the insoluble fraction containing the inclusion bodies was harvested by centrifugation for 10 min at 10,000 rpm. The inclusion bodies were resuspended in 200 mL of BEN-ZONASE® buffer (20 mM Tris-HCl pH 7.5 5 mM $MgCl_2$, 100 mM NaCl) containing 1250 U of BENZONASE® endonuclease (Sigma Aldrich, St. Louis Mo.). The slurry was stirred for 1 hr at 37° C. and centrifuged. The inclusion bodies were washed by resuspension in deionized water with a homogenizer and harvested by centrifugation for 10 min at 10,000 rpm.

Example 8

Improved Acid Cleavage for the Production of Peptide HC353

The purpose of this experiment is to show that the new acid cleavage sequences identified in Example 4 with peptide TBP1 allow for improved acid cleavage when another peptide is fused to the insolubility tag and therefore are of general use. Improved acid cleavage means faster at equal pH and temperature, at a lower temperature for equal pH and incubation time or at a higher pH for equal temperature and incubation time.

Each inclusion body paste was resuspended to 10% w/v in water containing 50 mM NaCl. Each slurry (70 mL) was acidified by addition of HCl to pH 6, pH 5, pH 4, pH 3, or pH 2. The acidified slurries were incubated at 60° C., 70° C. or 80° C. with periodic manual agitation. Aliquots of the acidified slurries were collected at 15, 30, 60, 90, 120, 180 and 240 min and placed on ice. Once all the aliquots were collected, the samples were neutralized by addition of 1 M NaOH.

The efficiency of the acid cleavage was assessed by SDS polyacrylamide gel electrophoresis and the gels were stained with Coomassie blue. The bands corresponding to HC353 and KSI which have similar MW, could be resolved easily because of the abnormally slow gel mobility of HC353. The summary data is provided in Table 9 and is shown in FIGS. 9, 10, 11, and 12 where in each of the figures arrows are used to indicate the full length fusion construct ("F"), the peptide of interest HC353 ("H") and the inclusion body tag KSI(C4E) ("K"). The data confirms the results obtained with another peptide fusion in Example 4 and indicates that the improved acid cleavage sites can be used broadly for the production of different peptides.

TABLE 9

Data summary of the variant acid cleavage sites showing fusion proteins more labile to acid pH (faster kinetics, less acidic pH or lower temperature).

| Strain ID | Cleavage Sequence (SEQ ID NO:) | Fastest time for complete digest @ pH 2, 80° C. (min) | Lowest temp. for complete digest @ pH 2, 4 hrs (° C.) | Highest pH for complete digest @ 80° C., 4 hrs (pH) |
|---|---|---|---|---|
| LD1474 | DP | 240 | 80 | 2 |
| LR2050 | DPDPPDPP (SEQ ID NO: 5) | 60 | 60 | 4 |
| LR2321 | DPPDPPDP (SEQ ID NO: 7) | 90 | 70 | 3 |
| LR1755 | DPDPDP (SEQ ID NO: 2) | 120 | 70 | 3 |

---

What is claimed is:

1. A fusion peptide comprising two peptides separated by an acid-cleavable linker according to the following general formula:

PEP1-L-PEP2 wherein,
a) PEP1 and PEP2 are independently functional peptides wherein at least one is a peptide of interest ("POI"); and
b) L is an acid-cleavable linker comprising a peptide DPP-DPPDP (SEQ ID N0:7), wherein D is aspartic acid and P is proline.

2. The fusion peptide of claim 1 wherein PEP1 and PEP2 are nonidentical.

3. The fusion peptide of claim 2, wherein the fusion peptide is soluble in a recombinant cell.

4. The fusion peptide of claim 3 wherein the recombinant cell is a recombinant microbial cell.

5. The fusion peptide of claim 4 wherein the recombinant microbial cell is a recombinant bacterial cell.

6. The fusion peptide of claim 4 wherein the recombinant microbial cell is a recombinant yeast cell.

7. The fusion peptide of claim 2, wherein the fusion peptide is insoluble in a recombinant cell.

8. The fusion peptide of claim 7 wherein the recombinant cell is a recombinant microbial cell.

9. The fusion peptide of claim 8 wherein the recombinant microbial cell is a recombinant yeast cell.

10. The fusion peptide of claim 9 wherein the recombinant microbial cell is a recombinant bacterial cell.

11. The fusion peptide of claim 2 wherein either of PEP1 or PEP2 comprises an inclusion body tag ("IBT").

12. The fusion peptide of claim 11 wherein the fusion peptide is present in inclusion bodies.

13. The fusion peptide of claim 2 wherein the acid-cleavable linker is cleaved by incubation at a pH in the range from about pH 1 to about pH 4.

14. The fusion peptide of claim 2 wherein the acid-cleavable linker is cleaved by incubating at a temperature of about 40° C. to about 90° C.

15. The fusion peptide of claim 14 wherein the acid-cleavable linker is cleaved by incubating at a temperature of about 50° C. to about 80° C.

16. The fusion peptide of claim 15 wherein the acid-cleavable linker is cleaved by incubating at a temperature of about 60° C. to about 70° C.

17. The fusion peptide of claim 2 wherein the acid-cleavable linker is cleaved by incubating at a pH of about pH 2 to about pH 4 and at a temperature of about 50° C. to about 80° C.

18. A recombinant cell expressing a fusion protein having the structure

PEP1-L-PEP2 wherein,
i) PEP1 and PEP2 are independently functional peptides, one of which is a POI; and
ii) L is an acid-cleavable linker comprising a peptide DPP-DPPDP (SEQ ID N0:7),
wherein D is aspartic acid and P is proline; and
wherein the expressed fusion peptide is present in the recombinant cell.

19. The recombinant cell of claim 18 wherein the recombinant cell is a recombinant microbial cell.

20. The recombinant cell of claim 19 wherein the recombinant cell is a recombinant bacterial cell.

21. The recombinant cell of claim 19 wherein the recombinant cell is a recombinant microbial cell is a recombinant yeast cell.

22. An acid-cleavable peptide linker comprising a peptide DPPDPPDP (SEQ ID NO:7), wherein D is aspartic acid and P is proline.

23. A method of preparing at least one peptide of interest ("POI") from a fusion peptide comprising at least one POI, comprising:
a) providing a recombinant cell synthesizing the fusion peptide of claim 1;
b) contacting the fusion peptide with a solution of sufficiently acidic pH so that linker L is cleaved, and
c) isolating the at least one POI.

24. The method of claim 23 wherein the recombinant cell is a recombinant microbial cell.

25. The method of claim 24 wherein the recombinant microbial cell is a recombinant yeast cell.

26. The method of claim 24 wherein the recombinant microbial cell is a recombinant bacterial cell.

27. The method of claim 23 wherein the acid-cleavable linker is cleaved by incubating the fusion peptides at a pH in the range from about pH 1 to about pH 4.

28. The method of claim 23 wherein the acid-cleavable linker is cleaved by incubating the fusion peptides at a pH in the range from about pH 2 to about pH 4.

29. The method of claim 23 wherein the acid-cleavable linker is cleaved by incubating the fusion peptides at a pH in the range from about pH 3 to about pH 4.

30. The method of claim 23 wherein the acid-cleavable linker is cleaved by incubating the fusion peptides at a pH of about 4.

31. The method of claim 23 wherein the acid-cleavable linker is cleaved by incubating the fusion peptides at a temperature of about 40° C. to about 90° C.

32. The method of claim 23 wherein the acid-cleavable linker is cleaved by incubating the fusion peptides at a temperature of about 50° C. to about 80° C.

33. The method of claim 23 wherein the acid-cleavable linker is cleaved by incubating the fusion peptides at a temperature of about 60° C. to about 70° C.

34. The method of claim 23 wherein the acid-cleavable linker is cleaved by incubating the fusion peptides at a temperature of about 60° C.

35. The method of claim 23 wherein the acid-cleavable linker is cleaved by incubating the fusion peptides at a pH of about pH 2 to about pH 4 using a temperature of about 50° C. to about 80° C.

36. The method of claim 23, wherein PEP1 and PEP2 are both POIs.

37. The method of claim 36, wherein the fusion peptide is soluble in the recombinant cell.

38. The method of claim 36, wherein the fusion peptide is insoluble in the recombinant cell.

39. The method of claim 38, wherein cleaving the fusion peptide under acidic conditions renders the at least one POI soluble.

40. The method of claim 23, wherein either PEP1 or PEP2 of the fusion peptide comprises an inclusion body tag, thereby comprising a non-POI portion of the fusion peptide.

41. The method of claim 40, wherein the non-POI portion remains insoluble after cleaving the fusion peptide.

\* \* \* \* \*

SEQUENCE LISTING

<160> NUMBER OF SEQ ID NOS: 268

<210> SEQ ID NO 1
<211> LENGTH: 4
<212> TYPE: PRT
<213> ORGANISM: Artificial Sequence
<220> FEATURE:
<223> OTHER INFORMATION: synthetic construct

<400> SEQUENCE: 1

Asp Pro Asp Pro
1

<210> SEQ ID NO 2
<211> LENGTH: 6
<212> TYPE: PRT
<213> ORGANISM: Artificial Sequence
<220> FEATURE:
<223> OTHER INFORMATION: synthetic construct

<400> SEQUENCE: 2

Asp Pro Asp Pro Asp Pro
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic construct

<400> SEQUENCE: 3

Asp Pro Asp Pro Asp Pro Asp Pro
1               5

<210> SEQ ID NO 4
<211> LENGTH: 7
<212> TYPE: PRT
<213> ORGANISM: Artificial Sequence
<220> FEATURE:
<223> OTHER INFORMATION: synthetic construct

<400> SEQUENCE: 4

Asp Pro Asp Pro Asp Pro Pro

<210> SEQ ID NO 5
<211> LENGTH: 8
<212> TYPE: PRT
<213> ORGANISM: Artificial Sequence
<220> FEATURE:
<223> OTHER INFORMATION: synthetic construct

<400> SEQUENCE: 5

Asp Pro Asp Pro Pro Asp Pro Pro
1               5

<210> SEQ ID NO 6
<211> LENGTH: 7
<212> TYPE: PRT
<213> ORGANISM: Artificial Sequence
<220> FEATURE:
<223> OTHER INFORMATION: synthetic construct

<400> SEQUENCE: 6

Asp Pro Asp Pro Pro Asp Pro
1               5

<210> SEQ ID NO 7
<211> LENGTH: 8
<212> TYPE: PRT
<213> ORGANISM: Artificial Sequence
<220> FEATURE:
<223> OTHER INFORMATION: synthetic construct

<400> SEQUENCE: 7

Asp Pro Pro Asp Pro Pro Asp Pro
1               5

<210> SEQ ID NO 8
<211> LENGTH: 103
<212> TYPE: DNA
<213> ORGANISM: Artificial Sequence
<220> FEATURE:
<223> OTHER INFORMATION: synthetic construct

<400> SEQUENCE: 8
ggatccatcg aaggtcgttt ccacgaaaac tggccgtctg gtggcggtac ctctacttcc    60
aaagcttcca ccactacgac ttctagcaaa accaccacta cat                    103

<210> SEQ ID NO 9
<211> LENGTH: 104
<212> TYPE: DNA
<213> ORGANISM: Artificial Sequence
<220> FEATURE:
<223> OTHER INFORMATION: synthetic construct

<400> SEQUENCE: 9
cctctaagac taccacgact acctccaaaa cctctactac ctctagctcc tctacgggcg    60
gtggcactca caagacctct actcagcgtc tgctggctgc ataa                   104

<210> SEQ ID NO 10
<211> LENGTH: 69
<212> TYPE: DNA
<213> ORGANISM: Artificial Sequence
<220> FEATURE:
<223> OTHER INFORMATION: synthetic construct

<400> SEQUENCE: 10
ttatgcagcc agcagacgct gagtagaggt cttgtgagtg ccaccgcccg tagaggagct    60

```
agaggtagt                                                              69

<210> SEQ ID NO 11
<211> LENGTH: 69
<212> TYPE: DNA
<213> ORGANISM: Artificial Sequence
<220> FEATURE:
<223> OTHER INFORMATION: synthetic construct

<400> SEQUENCE: 11
agaggttttg gaggtagtcg tggtagtctt agaggatgta gtggtggttt tgctagaagt      60
cgtagtggt                                                              69

<210> SEQ ID NO 12
<211> LENGTH: 69
<212> TYPE: DNA
<213> ORGANISM: Artificial Sequence
<220> FEATURE:
<223> OTHER INFORMATION: synthetic construct

<400> SEQUENCE: 12
ggaagctttg gaagtagagg taccgccacc agacggccag ttttcgtgga aacgaccttc      60
gatggatcc                                                              69

<210> SEQ ID NO 13
<211> LENGTH: 51
<212> TYPE: DNA
<213> ORGANISM: Artificial Sequence
<220> FEATURE:
<223> OTHER INFORMATION: primer

<400> SEQUENCE: 13 cccttcacc ggatccatcg atccagatcc acgtttccac gaaaactggc c                51

<210> SEQ ID NO 14
<211> LENGTH: 57
<212> TYPE: DNA
<213> ORGANISM: Artificial Sequence
<220> FEATURE:
<223> OTHER INFORMATION: primer

<400> SEQUENCE: 14 cccttcacc ggatccatcg atccagatcc agatccacgt ttccacgaaa actggcc         57

<210> SEQ ID NO 15
<211> LENGTH: 63
<212> TYPE: DNA
<213> ORGANISM: Artificial Sequence
<220> FEATURE:
<223> OTHER INFORMATION: primer

<400> SEQUENCE: 15 cccttcacc ggatccatcg atccagatcc agatccagat ccacgtttcc acgaaaactg      60
gcc                                                                    63

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
gtaatacggt tatccacaga atcag                                            25
```

<210> SEQ ID NO 17
<211> LENGTH: 207
<212> TYPE: DNA
<213> ORGANISM: Artificial Sequence
<220> FEATURE:
<223> OTHER INFORMATION: synthetic construct

<400> SEQUENCE: 17

```
ggatccatcg aaggtcgttt ccacgaaaac tggccgtctg gtggcggtac ctctacttcc      60
aaagcttcca ccactacgac ttctagcaaa accaccacta catcctctaa gactaccacg     120
actacctcca aacctctac tacctctagc tcctctacgg gcggtggcac tcacaagacc     180
tctactcagc gtctgctggc tgcataa                                         207
```

<210> SEQ ID NO 18
<211> LENGTH: 96
<212> TYPE: PRT
<213> ORGANISM: Artificial Sequence
<220> FEATURE:
<223> OTHER INFORMATION: synthetic construct

<400> SEQUENCE: 18

```
Met Ser Tyr Tyr His His His His His His Leu Glu Ser Thr Ser Leu
1               5                   10                  15

Tyr Lys Lys Ala Gly Ser Ala Ala Ala Pro Phe Thr Gly Ser Ile Glu
            20                  25                  30

Gly Arg Phe His Glu Asn Trp Pro Ser Gly Gly Gly Thr Ser Thr Ser
        35                  40                  45

Lys Ala Ser Thr Thr Thr Thr Ser Ser Lys Thr Thr Thr Thr Ser Ser
    50                  55                  60

Lys Thr Thr Thr Thr Thr Ser Lys Thr Ser Thr Thr Ser Ser Ser Ser
65                  70                  75                  80

Thr Gly Gly Gly Thr His Lys Thr Ser Thr Gln Arg Leu Leu Ala Ala
                85                  90                  95
```

<210> SEQ ID NO 19
<211> LENGTH: 68
<212> TYPE: PRT
<213> ORGANISM: Artificial Sequence
<220> FEATURE:
<223> OTHER INFORMATION: synthetic construct

<400> SEQUENCE: 19

```
Gly Ser Ile Glu Gly Arg Phe His Glu Asn Trp Pro Ser Gly Gly Gly
1               5                   10                  15

Thr Ser Thr Ser Lys Ala Ser Thr Thr Thr Thr Ser Ser Lys Thr Thr
            20                  25                  30

Thr Thr Ser Ser Lys Thr Thr Thr Thr Thr Ser Lys Thr Ser Thr Thr
        35                  40                  45

Ser Ser Ser Ser Thr Gly Gly Gly Thr His Lys Thr Ser Thr Gln Arg
    50                  55                  60

Leu Leu Ala Ala
65
```

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20

```
tcattatgca gccagcagcg c                                              21
```

<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21

```
caccggatcc atcgaaggtc gt                                             22
```

<210> SEQ ID NO 22
<211> LENGTH: 2580
<212> TYPE: DNA
<213> ORGANISM: Artificial Sequence
<220> FEATURE:
<223> OTHER INFORMATION: pENTR/D-TOPO plasmid

<400> SEQUENCE: 22

```
ctttcctgcg ttatccctg attctgtgga taaccgtatt accgcctttg agtgagctga      60
taccgctcgc cgcagccgaa cgaccgagcg cagcgagtca gtgagcgagg aagcggaaga    120
gcgcccaata cgcaaaccgc ctctccccgc gcgttggccg attcattaat gcagctggca    180
cgacaggttt cccgactgga aagcgggcag tgagcgcaac gcaattaata cgcgtaccgc    240
tagccaggaa gagtttgtag aaacgcaaaa aggccatccg tcaggatggc cttctgctta    300
gtttgatgcc tggcagttta tggcgggcgt cctgcccgcc accctccggg ccgttgcttc    360
acaacgttca atccgctcc cggcggattt gtcctactca ggagagcgtt caccgacaaa    420
caacagataa aacgaaaggc ccagtcttcc gactgagcct ttcgttttat ttgatgcctg    480
gcagttccct actctcgcgt taacgctagc atggatgttt tcccagtcac gacgttgtaa    540
aacgacggcc agtcttaagc tcgggcccca ataatgatt ttattttgac tgatagtgac    600
ctgttcgttg caacaaattg atgagcaatg cttttttata tgccaactt tgtacaaaaa    660
agcaggctcc gcggccgccc ccttcaccaa gggtgggcgc gccgacccag cttcttgta    720
caaagttggc attataagaa agcattgctt atcaatttgt tgcaacgaac aggtcactat    780
cagtcaaaat aaaatcatta tttgccatcc agctgatatc ccctatagtg agtcgtatta    840
catggtcata gctgtttcct ggcagctctg gcccgtgtct caaaatctct gatgttacat    900
tgcacaagat aaaaatatat catcatgaac aataaaactg tctgcttaca taaacagtaa    960
tacaagggt gttatgagcc atattcaacg ggaaacgtcg aggccgcgat taaattccaa   1020
catggatgct gatttatatg ggtataaatg ggctcgcgat aatgtcgggc aatcaggtgc   1080
gacaatctat cgcttgtatg ggaagcccga tcgccagag ttgtttctga acatggcaa    1140
aggtagcgtt gccaatgatg ttacagatga atggtcaga ctaaactggc tgacggaatt    1200
tatgcctctt ccgaccatca agcattttat ccgtactcct gatgatgcat ggttactcac   1260
cactgcgatc cccggaaaaa cagcattcca ggtattagaa gaatatcctg attcaggtga   1320
aaatattgtt gatgcgctgg cagtgttcct gcgccggttg cattcgattc ctgtttgtaa   1380
ttgtcctttt aacagcgatc gcgtatttcg tctcgctcag gcgcaatcac gaatgaataa   1440
cggtttggtt gatgcgagtg attttgatga cgagcgtaat ggctggcctg ttgaacaagt   1500
ctggaaagaa atgcataaac ttttgccatt ctcaccggat tcagtcgtca ctcatggtga   1560
tttctcactt gataacctta ttttgacga ggggaaatta taggttgta ttgatgttgg   1620
```

-continued

| | |
|---|---|
| acgagtcgga atcgcagacc gataccagga tcttgccatc ctatggaact gcctcggtga | 1680 |
| gttttctcct tcattacaga aacggctttt tcaaaaatat ggtattgata atcctgatat | 1740 |
| gaataaattg cagtttcatt tgatgctcga tgagttttc taatcagaat tggttaattg | 1800 |
| gttgtaacac tggcagagca ttacgctgac ttgacgggac ggcgcaagct catgaccaaa | 1860 |
| atcccttaac gtgagttacg cgtcgttcca ctgagcgtca gaccccgtag aaaagatcaa | 1920 |
| aggatcttct tgagatcctt ttttttctgcg cgtaatctgc tgcttgcaaa caaaaaaacc | 1980 |
| accgctacca gcggtggttt gtttgccgga tcaagagcta ccaactcttt tccgaaggt | 2040 |
| aactggcttc agcagagcgc agataccaaa tactgtcctt ctagtgtagc cgtagttagg | 2100 |
| ccaccacttc aagaactctg tagcaccgcc tacatacctc gctctgctaa tcctgttacc | 2160 |
| agtggctgct gccagtggcg ataagtcgtg tcttaccggg ttggactcaa gacgatagtt | 2220 |
| accggataag gcgcagcggt cgggctgaac ggggggttcg tgcacacagc ccagcttgga | 2280 |
| gcgaacgacc tacaccgaac tgagatacct acagcgtgag cattgagaaa gcgccacgct | 2340 |
| tcccgaaggg agaaaggcgg acaggtatcc ggtaagcggc agggtcggaa caggagagcg | 2400 |
| cacgagggag cttccagggg gaaacgcctg gtatctttat agtcctgtcg ggtttcgcca | 2460 |
| cctctgactt gagcgtcgat ttttgtgatg ctcgtcaggg gggcggagcc tatggaaaaa | 2520 |
| cgccagcaac gcggccttt tacggttcct ggccttttgc tggccttttg ctcacatgtt | 2580 |

<210> SEQ ID NO 23
<211> LENGTH: 6354
<212> TYPE: DNA
<213> ORGANISM: Artificial Sequence
<220> FEATURE:
<223> OTHER INFORMATION: Plasmid pDEST17

<400> SEQUENCE: 23

| | |
|---|---|
| agatctcgat cccgcgaaat taatacgact cactataggg agaccacaac ggtttccctc | 60 |
| tagaaataat tttgtttaac tttaagaagg agatatacat atgtcgtact accatcacca | 120 |
| tcaccatcac ctcgaatcaa caagtttgta caaaaaagct gaacgagaaa cgtaaaatga | 180 |
| tataaatatc aatatattaa attagatttt gcataaaaaa cagactacat aatactgtaa | 240 |
| aacacaacat atccagtcac tatggcggcc gcattaggca ccccaggctt tacactttat | 300 |
| gcttccggct cgtataatgt gtggattttg agttaggatc cgtcgagatt ttcaggagct | 360 |
| aaggaagcta aaatggagaa aaaaatcact ggatatacca ccgttgatat atcccaatgg | 420 |
| catcgtaaag aacattttga ggcatttcag tcagttgctc aatgtaccta taaccagacc | 480 |
| gttcagctgg atattacggc cttttaaag accgtaaaga aaataagca caagttttat | 540 |
| ccggccttta ttcacattct tgcccgcctg atgaatgctc atccggaatt ccgtatggca | 600 |
| atgaaagacg gtgagctggt gatatgggat agtgttcacc cttgttacac cgttttccat | 660 |
| gagcaaactg aaacgttttc atcgctctgg agtgaatacc acgacgattt ccggcagttt | 720 |
| ctacacatat attcgcaaga tgtggcgtgt tacggtgaaa acctggccta tttccctaaa | 780 |
| gggtttattg agaatatgtt ttcgtctca gccaatccct gggtgagttt caccagtttt | 840 |
| gatttaaacg tggccaatat ggacaacttc ttcgccccg ttttcaccat gggcaaatat | 900 |
| tatacgcaag cgacaaggt gctgatgccg ctggcgattc aggttcatca tgccgtctgt | 960 |
| gatggcttcc atgtcggcag aatgcttaat gaattacaac agtactgcga tgagtggcag | 1020 |
| ggcggggcgt aaagatctgg atccggctta ctaaaagcca gataacagta tgcgtatttg | 1080 |
| cgcgctgatt tttgcggtat aagaatatat actgatatgt atacccgaag tatgtcaaaa | 1140 |

```
agaggtgtgc tatgaagcag cgtattacag tgacagttga cagcgacagc tatcagttgc   1200
tcaaggcata tatgatgtca atatctccgg tctggtaagc acaaccatgc agaatgaagc   1260
ccgtcgtctg cgtgccgaac gctggaaagc ggaaaatcag gaagggatgg ctgaggtcgc   1320
ccggtttatt gaaatgaacg gctcttttgc tgacgagaac agggactggt gaaatgcagt   1380
ttaaggttta cacctataaa agagagagcc gttatcgtct gtttgtggat gtacagagtg   1440
atattattga cacgcccggg cgacggatgg tgatccccct ggccagtgca cgtctgctgt   1500
cagataaagt ctcccgtgaa ctttacccgg tggtgcatat cggggatgaa agctggcgca   1560
tgatgaccac cgatatggcc agtgtgccgg tctccgttat cggggaagaa gtggctgatc   1620
tcagccaccg cgaaaatgac atcaaaaacg ccattaacct gatgttctgg ggaatataaa   1680
tgtcaggctc ccttatacac agccagtctg caggtcgacc atagtgactg gatatgttgt   1740
gttttacagt attatgtagt ctgttttta tgcaaaatct aatttaatat attgatattt      1800
atatcatttt acgtttctcg ttcagctttc ttgtacaaag tggttgattc gaggctgcta   1860
acaaagcccg aaaggaagct gagttggctg ctgccaccgc tgagcaataa ctagcataac   1920
cccttggggc ctctaaacgg gtcttgaggg gttttttgct gaaaggagga actatatccg   1980
gatatccaca ggacgggtgt ggtcgccatg atcgcgtagt cgatagtggc tccaagtagc   2040
gaagcgagca ggactgggcg gcggccaaag cggtcggaca gtgctccgag aacgggtgcg   2100
catagaaatt gcatcaacgc atatagcgct agcagcacgc catagtgact ggcgatgctg   2160
tcggaatgga cgtatcccg caagaggccc ggcagtaccg gcataaccaa gcctatgcct    2220
acagcatcca gggtgacggt gccgaggatg acgatgagcg cattgttaga tttcatacac   2280
ggtgcctgac tgcgttagca atttaactgt gataaactac cgcattaaag cttatcgatg   2340
ataagctgtc aaacatgaga attcttgaag acgaaagggc ctcgtgatac gcctatttt    2400 ataggttaat gtcatgataa taatggtttc ttagacgtca ggtggcactt ttcggggaaa   2460
tgtgcgcgga acccctattt gtttattttt ctaaatacat tcaaatatgt atccgctcat   2520
gagacaataa ccctgataaa tgcttcaata atattgaaaa aggaagagta tgagtattca   2580
acatttccgt gtcgccctta ttcccttttt tgcggcattt tgccttcctg tttttgctca   2640
cccagaaacg ctggtgaaag taaaagatgc tgaagatcag ttgggtgcac gagtgggtta   2700
catcgaactg gatctcaaca gcggtaagat ccttgagagt tttcgccccg aagaacgttt   2760
tccaatgatg agcactttta aagttctgct atgtggcgcg gtattatccc gtgttgacgc   2820
cgggcaagag caactcggtc gccgcataca ctattctcag aatgacttgg ttgagtactc   2880
accagtcaca gaaaagcatc ttacggatgg catgacagta agagaattat gcagtgctgc   2940
cataaccatg agtgataaca ctgcggccaa cttacttctg acaacgatcg gaggaccgaa   3000
ggagctaacc gcttttttgc acaacatggg ggatcatgta actcgccttg atcgttggga   3060
accggagctg aatgaagcca taccaaacga cgagcgtgac accacgatgc ctgcagcaat   3120
ggcaacaacg ttgcgcaaac tattaactgg cgaactactt actctagctt cccggcaaca   3180
attaatagac tggatggagg cggataaagt tgcaggacca cttctgcgct cggcccttcc   3240
ggctggctgg tttattgctg ataaatctgg agccggtgag cgtgggtctc gcggtatcat   3300
tgcagcactg gggccagatg gtaagccctc ccgtatcgta gttatctaca cgacggggag   3360
tcaggcaact atggatgaac gaaatagaca gatcgctgag ataggtgcct cactgattaa   3420
gcattggtaa ctgtcagacc aagtttactc atatatactt tagattgatt taaaacttca   3480 ttttttaattt aaaaggatct aggtgaagat ccttttttgat aatctcatga ccaaaatccc   3540
```

```
ttaacgtgag ttttcgttcc actgagcgtc agaccccgta gaaaagatca aggatcttc    3600
ttgagatcct ttttttctgc gcgtaatctg ctgcttgcaa acaaaaaaac caccgctacc   3660
agcggtggtt tgtttgccgg atcaagagct accaactctt tttccgaagg taactggctt   3720
cagcagagcg cagataccaa atactgtcct tctagtgtag ccgtagttag gccaccactt   3780
caagaactct gtagcaccgc ctacatacct cgctctgcta atcctgttac cagtggctgc   3840
tgccagtggc gataagtcgt gtcttaccgg gttggactca agacgatagt taccggataa   3900
ggcgcagcgg tcgggctgaa cggggggttc gtgcacacag cccagcttgg agcgaacgac   3960
ctacaccgaa ctgagatacc tacagcgtga gctatgagaa agcgccacgc ttcccgaagg   4020
gagaaaggcg gacaggtatc cggtaagcgg cagggtcgga acaggagagc gcacgaggga   4080
gcttccaggg ggaaacgcct ggtatcttta tagtcctgtc gggtttcgcc acctctgact   4140
tgagcgtcga ttttgtgat gctcgtcagg ggggcggagc ctatggaaaa acgccagcaa    4200
cgcggccttt ttacggttcc tggccttttg ctggccttttt gctcacatgt tctttcctgc   4260
gttatcccct gattctgtgg ataaccgtat taccgccttt gagtgagctg ataccgctcg   4320
ccgcagccga acgaccgagc gcagcgagtc agtgagcgag gaagcggaag agcgcctgat   4380
gcggtatttt ctccttacgc atctgtgcgg tatttcacac cgcatatatg gtgcactctc   4440
agtacaatct gctctgatgc cgcatagtta agccagtata cactccgcta tcgctacgtg   4500
actgggtcat ggctgcgccc cgacacccgc caacacccgc tgacgcgccc tgacgggctt   4560
gtctgctccc ggcatccgct tacagacaag ctgtgaccgt ctccgggagc tgcatgtgtc   4620
agaggttttc accgtcatca ccgaaacgcg cgaggcagct gcggtaaagc tcatcagcgt   4680
ggtcgtgaag cgattcacag atgtctgcct gttcatccgc gtccagctcg ttgagttct    4740
ccagaagcgt taatgtctgg cttctgataa agcgggccat gttaagggcg ttttttcct    4800
gtttggtcac tgatgcctcc gtgtaagggg gatttctgtt catggggta atgataccga    4860
tgaaacgaga gaggatgctc acgatacggg ttactgatga tgaacatgcc cggttactgg   4920
aacgttgtga gggtaaacaa ctggcggtat ggatgcggcg ggaccagaga aaaatcactc   4980
agggtcaatg ccagcgcttc gttaatacag atgtaggtgt tccacagggt agccagcagc   5040
atcctgcgat gcagatccgg aacataatgg tgcagggcgc tgacttccgc gtttccagac   5100
tttacgaaac acggaaaccg aagaccattc atgttgttgc tcaggtcgca gacgttttgc   5160
agcagcagtc gcttcacgtt cgctcgcgta tcggtgattc attctgctaa ccagtaaggc   5220
aacccccgcca gcctagccgg gtcctcaacg acaggagcac gatcatgcgc acccgtggcc   5280
aggacccaac gctgcccgag atgcgccgcg tgcggctgct ggagatggcg gacgcgatgg   5340
atatgttctg ccaagggttg gtttgcgcat tcacagttct ccgcaagaat tgattggctc   5400
caattcttgg agtggtgaat ccgttagcga ggtgccgccg gcttccattc aggtcgaggt   5460
ggcccggctc catgcaccgc gacgcaacgc ggggaggcag acaaggtata gggcggcgcc   5520
tacaatccat gccaacccgt tccatgtgct cgccgaggcg gcataaatcg ccgtgacgat   5580
cagcggtcca gtgatcgaag ttaggctggt aagagccgcg agcgatcctt gaagctgtcc   5640
ctgatggtcg tcatctacct gcctggacag catggcctgc aacgcgggca tcccgatgcc   5700
gccggaagcg agaagaatca taatgggaa ggccatccag cctcgcgtcg cgaacgccag    5760
caagacgtag cccagcgcgt cggccgccat gccggcgata atggcctgct tctcgccgaa   5820
acgtttggtg gcgggaccag tgacgaaggc ttgagcgagg gcgtgcaaga ttccgaatac   5880
cgcaagcgac aggccgatca tcgtcgcgct ccagcgaaag cggtcctcgc cgaaaatgac   5940
```

```
ccagagcgct gccggcacct gtcctacgag ttgcatgata aagaagacag tcataagtgc    6000
ggcgacgata gtcatgcccc gcgcccaccg gaaggagctg actgggttga aggctctcaa    6060
gggcatcggt cgatcgacgc tctcccttat gcgactcctg cattaggaag cagcccagta    6120
gtaggttgag gccgttgagc accgccgccg caaggaatgg tgcatgcaag agatggcgc     6180 ccaacagtcc cccggccacg gggcctgcca ccatacccac gccgaaacaa gcgctcatga    6240
gcccgaagtg gcgagcccga tcttccccat cggtgatgtc ggcgatatag gcgccagcaa    6300
ccgcacctgt ggcgccggtg atgccggcca cgatgcgtcc ggcgtagagg atcg          6354

<210> SEQ ID NO 24
<211> LENGTH: 45
<212> TYPE: DNA
<213> ORGANISM: Artificial Sequence
<220> FEATURE:
<223> OTHER INFORMATION: primer

<400> SEQUENCE: 24 cccccttcacc ggatccatcg atccacgttt ccacgaaaac tggcc                   45

<210> SEQ ID NO 25
<211> LENGTH: 45
<212> TYPE: DNA
<213> ORGANISM: Artificial Sequence
<220> FEATURE:
<223> OTHER INFORMATION: primer

<400> SEQUENCE: 25
ggccagtttt cgtggaaacg tggatcgatg gatccggtga agggg                    45

<210> SEQ ID NO 26
<211> LENGTH: 96
<212> TYPE: PRT
<213> ORGANISM: Artificial Sequence
<220> FEATURE:
<223> OTHER INFORMATION: synthetic construct

<400> SEQUENCE: 26

Met Ser Tyr Tyr His His His His His His Leu Glu Ser Thr Ser Leu
1               5                   10                  15

Tyr Lys Lys Ala Gly Ser Ala Ala Ala Pro Phe Thr Gly Ser Ile Asp
            20                  25                  30

Pro Arg Phe His Glu Asn Trp Pro Ser Ala Gly Gly Thr Ser Thr Ser
        35                  40                  45

Lys Ala Ser Thr Thr Thr Thr Ser Ser Lys Thr Thr Thr Thr Ser Ser
    50                  55                  60

Lys Thr Thr Thr Thr Thr Ser Lys Thr Ser Thr Ser Ser Ser Ser
65                  70                  75                  80

Thr Gly Gly Ala Thr His Lys Thr Ser Thr Gln Arg Leu Leu Ala Ala
                85                  90                  95

<210> SEQ ID NO 27
<211> LENGTH: 42
<212> TYPE: DNA
<213> ORGANISM: Artificial sequence
<220> FEATURE:
<223> OTHER INFORMATION: primer

<400> SEQUENCE: 27
caccggatcc atcgatccag cattccacga aaactggccg tc                       42

<210> SEQ ID NO 28
```

-continued

```
<211> LENGTH: 42
<212> TYPE: DNA
<213> ORGANISM: Artificial sequence
<220> FEATURE:
<223> OTHER INFORMATION: primer

<400> SEQUENCE: 28
gacggccagt ttcgtggaa tgctggatcg atggatccgg tg                42

<210> SEQ ID NO 29
<211> LENGTH: 42
<212> TYPE: DNA
<213> ORGANISM: Artificial sequence
<220> FEATURE:
<223> OTHER INFORMATION: primer

<400> SEQUENCE: 29
caccggatcc atcgatccaa acttccacga aaactggccg tc                42

<210> SEQ ID NO 30
<211> LENGTH: 42
<212> TYPE: DNA
<213> ORGANISM: Artificial sequence
<220> FEATURE:
<223> OTHER INFORMATION: primer

<400> SEQUENCE: 30
gacggccagt ttcgtggaa gtttggatcg atggatccgg tg                42

<210> SEQ ID NO 31
<211> LENGTH: 42
<212> TYPE: DNA
<213> ORGANISM: Artificial sequence
<220> FEATURE:
<223> OTHER INFORMATION: primer

<400> SEQUENCE: 31
caccggatcc atcgatccag atttccacga aaactggccg tc                42

<210> SEQ ID NO 32
<211> LENGTH: 42
<212> TYPE: DNA
<213> ORGANISM: Artificial sequence
<220> FEATURE:
<223> OTHER INFORMATION: primer

<400> SEQUENCE: 32
gacggccagt ttcgtggaa atctggatcg atggatccgg tg                42

<210> SEQ ID NO 33
<211> LENGTH: 42
<212> TYPE: DNA
<213> ORGANISM: Artificial sequence
<220> FEATURE:
<223> OTHER INFORMATION: primer

<400> SEQUENCE: 33
caccggatcc atcgatccat tgttccacga aaactggccg tc                42

<210> SEQ ID NO 34
<211> LENGTH: 42
<212> TYPE: DNA
<213> ORGANISM: Artificial sequence
<220> FEATURE:
<223> OTHER INFORMATION: primer

<400> SEQUENCE: 34
```

```
gacggccagt tttcgtggaa caatggatcg atggatccgg tg          42

<210> SEQ ID NO 35
<211> LENGTH: 42
<212> TYPE: DNA
<213> ORGANISM: Artificial sequence
<220> FEATURE:
<223> OTHER INFORMATION: primer

<400> SEQUENCE: 35
caccggatcc atcgatccac agttccacga aaactggccg tc          42

<210> SEQ ID NO 36
<211> LENGTH: 42
<212> TYPE: DNA
<213> ORGANISM: Artificial sequence
<220> FEATURE:
<223> OTHER INFORMATION: primer

<400> SEQUENCE: 36
gacggccagt tttcgtggaa ctgtggatcg atggatccgg tg          42

<210> SEQ ID NO 37
<211> LENGTH: 42
<212> TYPE: DNA
<213> ORGANISM: Artificial sequence
<220> FEATURE:
<223> OTHER INFORMATION: primer

<400> SEQUENCE: 37
caccggatcc atcgatccag aattccacga aaactggccg tc          42

<210> SEQ ID NO 38
<211> LENGTH: 42
<212> TYPE: DNA
<213> ORGANISM: Artificial sequence
<220> FEATURE:
<223> OTHER INFORMATION: primer

<400> SEQUENCE: 38
gacggccagt tttcgtggaa ttctggatcg atggatccgg tg          42

<210> SEQ ID NO 39
<211> LENGTH: 42
<212> TYPE: DNA
<213> ORGANISM: Artificial sequence
<220> FEATURE:
<223> OTHER INFORMATION: primer

<400> SEQUENCE: 39
caccggatcc atcgatccag gattccacga aaactggccg tc          42

<210> SEQ ID NO 40
<211> LENGTH: 42
<212> TYPE: DNA
<213> ORGANISM: Artificial sequence
<220> FEATURE:
<223> OTHER INFORMATION: primer

<400> SEQUENCE: 40
gacggccagt tttcgtggaa tcctggatcg atggatccgg tg          42

<210> SEQ ID NO 41
<211> LENGTH: 42
<212> TYPE: DNA
<213> ORGANISM: Artificial sequence
<220> FEATURE:
```

<223> OTHER INFORMATION: primer

<400> SEQUENCE: 41
caccggatcc atcgatccac acttccacga aaactggccg tc                42

<210> SEQ ID NO 42
<211> LENGTH: 42
<212> TYPE: DNA
<213> ORGANISM: Artificial sequence
<220> FEATURE:
<223> OTHER INFORMATION: primer

<400> SEQUENCE: 42
gacggccagt ttcgtggaa gtgtggatcg atggatccgg tg                 42

<210> SEQ ID NO 43
<211> LENGTH: 42
<212> TYPE: DNA
<213> ORGANISM: Artificial sequence
<220> FEATURE:
<223> OTHER INFORMATION: primer

<400> SEQUENCE: 43
caccggatcc atcgatccaa tcttccacga aaactggccg tc                42

<210> SEQ ID NO 44
<211> LENGTH: 42
<212> TYPE: DNA
<213> ORGANISM: Artificial sequence
<220> FEATURE:
<223> OTHER INFORMATION: primer

<400> SEQUENCE: 44
gacggccagt ttcgtggaa gattggatcg atggatccgg tg                 42

<210> SEQ ID NO 45
<211> LENGTH: 42
<212> TYPE: DNA
<213> ORGANISM: Artificial sequence
<220> FEATURE:
<223> OTHER INFORMATION: primer

<400> SEQUENCE: 45
caccggatcc atcgatccac tcttccacga aaactggccg tc                42

<210> SEQ ID NO 46
<211> LENGTH: 42
<212> TYPE: DNA
<213> ORGANISM: Artificial sequence
<220> FEATURE:
<223> OTHER INFORMATION: primer

<400> SEQUENCE: 46
gacggccagt ttcgtggaa gagtggatcg atggatccgg tg                 42

<210> SEQ ID NO 47
<211> LENGTH: 42
<212> TYPE: DNA
<213> ORGANISM: Artificial sequence
<220> FEATURE:
<223> OTHER INFORMATION: primer

<400> SEQUENCE: 47
caccggatcc atcgatccaa aattccacga aaactggccg tc                42

<210> SEQ ID NO 48

```
<211> LENGTH: 42
<212> TYPE: DNA
<213> ORGANISM: Artificial sequence
<220> FEATURE:
<223> OTHER INFORMATION: primer

<400> SEQUENCE: 48
gacggccagt ttcgtggaa ttttggatcg atggatccgg tg                              42

<210> SEQ ID NO 49
<211> LENGTH: 42
<212> TYPE: DNA
<213> ORGANISM: Artificial sequence
<220> FEATURE:
<223> OTHER INFORMATION: primer

<400> SEQUENCE: 49
caccggatcc atcgatccaa tgttccacga aaactggccg tc                              42

<210> SEQ ID NO 50
<211> LENGTH: 42
<212> TYPE: DNA
<213> ORGANISM: Artificial sequence
<220> FEATURE:
<223> OTHER INFORMATION: primer

<400> SEQUENCE: 50
gacggccagt ttcgtggaa cattggatcg atggatccgg tg                              42

<210> SEQ ID NO 51
<211> LENGTH: 42
<212> TYPE: DNA
<213> ORGANISM: Artificial sequence
<220> FEATURE:
<223> OTHER INFORMATION: primer

<400> SEQUENCE: 51
caccggatcc atcgatccat tcttccacga aaactggccg tc                              42

<210> SEQ ID NO 52
<211> LENGTH: 42
<212> TYPE: DNA
<213> ORGANISM: Artificial sequence
<220> FEATURE:
<223> OTHER INFORMATION: primer

<400> SEQUENCE: 52
gacggccagt ttcgtggaa gaatggatcg atggatccgg tg                              42

<210> SEQ ID NO 53
<211> LENGTH: 42
<212> TYPE: DNA
<213> ORGANISM: Artificial sequence
<220> FEATURE:
<223> OTHER INFORMATION: primer

<400> SEQUENCE: 53
caccggatcc atcgatccac cattccacga aaactggccg tc                              42

<210> SEQ ID NO 54
<211> LENGTH: 42
<212> TYPE: DNA
<213> ORGANISM: Artificial sequence
<220> FEATURE:
<223> OTHER INFORMATION: primer

<400> SEQUENCE: 54
```
gacggccagt tttcgtggaa tggtggatcg atggatccgg tg   42

<210> SEQ ID NO 55
<211> LENGTH: 42
<212> TYPE: DNA
<213> ORGANISM: Artificial sequence
<220> FEATURE:
<223> OTHER INFORMATION: primer

<400> SEQUENCE: 55
caccggatcc atcgatccat ccttccacga aaactggccg tc   42

<210> SEQ ID NO 56
<211> LENGTH: 42
<212> TYPE: DNA
<213> ORGANISM: Artificial sequence
<220> FEATURE:
<223> OTHER INFORMATION: primer

<400> SEQUENCE: 56
gacggccagt tttcgtggaa ggatggatcg atggatccgg tg   42

<210> SEQ ID NO 57
<211> LENGTH: 42
<212> TYPE: DNA
<213> ORGANISM: Artificial sequence
<220> FEATURE:
<223> OTHER INFORMATION: primer

<400> SEQUENCE: 57
caccggatcc atcgatccaa ccttccacga aaactggccg tc   42

<210> SEQ ID NO 58
<211> LENGTH: 42
<212> TYPE: DNA
<213> ORGANISM: Artificial sequence
<220> FEATURE:
<223> OTHER INFORMATION: primer

<400> SEQUENCE: 58
gacggccagt tttcgtggaa ggttggatcg atggatccgg tg   42

<210> SEQ ID NO 59
<211> LENGTH: 42
<212> TYPE: DNA
<213> ORGANISM: Artificial sequence
<220> FEATURE:
<223> OTHER INFORMATION: primer

<400> SEQUENCE: 59
caccggatcc atcgatccat ggttccacga aaactggccg tc   42

<210> SEQ ID NO 60
<211> LENGTH: 42
<212> TYPE: DNA
<213> ORGANISM: Artificial sequence
<220> FEATURE:
<223> OTHER INFORMATION: primer

<400> SEQUENCE: 60
gacggccagt tttcgtggaa ccatggatcg atggatccgg tg   42

<210> SEQ ID NO 61
<211> LENGTH: 42
<212> TYPE: DNA
<213> ORGANISM: Artificial sequence
<220> FEATURE:

<210> SEQ ID NO 61
<211> LENGTH: 42
<212> TYPE: DNA
<213> ORGANISM: Artificial sequence
<220> FEATURE:
<223> OTHER INFORMATION: primer

<400> SEQUENCE: 61
caccggatcc atcgatccat acttccacga aaactggccg tc                42

<210> SEQ ID NO 62
<211> LENGTH: 42
<212> TYPE: DNA
<213> ORGANISM: Artificial sequence
<220> FEATURE:
<223> OTHER INFORMATION: primer

<400> SEQUENCE: 62
gacggccagt tttcgtggaa gtatggatcg atggatccgg tg                42

<210> SEQ ID NO 63
<211> LENGTH: 42
<212> TYPE: DNA
<213> ORGANISM: Artificial sequence
<220> FEATURE:
<223> OTHER INFORMATION: primer

<400> SEQUENCE: 63
caccggatcc atcgatccag ttttccacga aaactggccg tc                42

<210> SEQ ID NO 64
<211> LENGTH: 42
<212> TYPE: DNA
<213> ORGANISM: Artificial sequence
<220> FEATURE:
<223> OTHER INFORMATION: primer

<400> SEQUENCE: 64
gacggccagt tttcgtggaa aactggatcg atggatccgg tg                42

<210> SEQ ID NO 65
<211> LENGTH: 40
<212> TYPE: DNA
<213> ORGANISM: Artificial sequence
<220> FEATURE:
<223> OTHER INFORMATION: primer

<400> SEQUENCE: 65
ccccttcacc ggatccgccg atccacgttt ccacgaaaac                40

<210> SEQ ID NO 66
<211> LENGTH: 40
<212> TYPE: DNA
<213> ORGANISM: Artificial sequence
<220> FEATURE:
<223> OTHER INFORMATION: primer

<400> SEQUENCE: 66
ccccttcacc ggatcccgtg atccacgttt ccacgaaaac                40

<210> SEQ ID NO 67
<211> LENGTH: 40
<212> TYPE: DNA
<213> ORGANISM: Artificial sequence
<220> FEATURE:
<223> OTHER INFORMATION: primer

<400> SEQUENCE: 67
ccccttcacc ggatccaacg atccacgttt ccacgaaaac                40

<210> SEQ ID NO 68

-continued

<211> LENGTH: 40
<212> TYPE: DNA
<213> ORGANISM: Artificial sequence
<220> FEATURE:
<223> OTHER INFORMATION: primer

<400> SEQUENCE: 68
ccccttcacc ggatccgatg atccacgttt ccacgaaaac         40

<210> SEQ ID NO 69
<211> LENGTH: 40
<212> TYPE: DNA
<213> ORGANISM: Artificial sequence
<220> FEATURE:
<223> OTHER INFORMATION: primer

<400> SEQUENCE: 69
ccccttcacc ggatccttgg atccacgttt ccacgaaaac         40

<210> SEQ ID NO 70
<211> LENGTH: 40
<212> TYPE: DNA
<213> ORGANISM: Artificial sequence
<220> FEATURE:
<223> OTHER INFORMATION: primer

<400> SEQUENCE: 70
ccccttcacc ggatcccagg atccacgttt ccacgaaaac         40

<210> SEQ ID NO 71
<211> LENGTH: 40
<212> TYPE: DNA
<213> ORGANISM: Artificial sequence
<220> FEATURE:
<223> OTHER INFORMATION: primer

<400> SEQUENCE: 71
ccccttcacc ggatccgaag atccacgttt ccacgaaaac         40

<210> SEQ ID NO 72
<211> LENGTH: 40
<212> TYPE: DNA
<213> ORGANISM: Artificial sequence
<220> FEATURE:
<223> OTHER INFORMATION: primer

<400> SEQUENCE: 72
ccccttcacc ggatccggag atccacgttt ccacgaaaac         40

<210> SEQ ID NO 73
<211> LENGTH: 40
<212> TYPE: DNA
<213> ORGANISM: Artificial sequence
<220> FEATURE:
<223> OTHER INFORMATION: primer

<400> SEQUENCE: 73
ccccttcacc ggatcccacg atccacgttt ccacgaaaac         40

<210> SEQ ID NO 74
<211> LENGTH: 40
<212> TYPE: DNA
<213> ORGANISM: Artificial sequence
<220> FEATURE:
<223> OTHER INFORMATION: primer

<400> SEQUENCE: 74

```
ccccttcacc ggatccctcg atccacgttt ccacgaaaac                           40
```

<210> SEQ ID NO 75
<211> LENGTH: 40
<212> TYPE: DNA
<213> ORGANISM: Artificial sequence
<220> FEATURE:
<223> OTHER INFORMATION: primer

<400> SEQUENCE: 75

```
ccccttcacc ggatccaaag atccacgttt ccacgaaaac                           40
```

<210> SEQ ID NO 76
<211> LENGTH: 40
<212> TYPE: DNA
<213> ORGANISM: Artificial sequence
<220> FEATURE:
<223> OTHER INFORMATION: primer

<400> SEQUENCE: 76

```
ccccttcacc ggatccatgg atccacgttt ccacgaaaac                           40
```

<210> SEQ ID NO 77
<211> LENGTH: 40
<212> TYPE: DNA
<213> ORGANISM: Artificial sequence
<220> FEATURE:
<223> OTHER INFORMATION: primer

<400> SEQUENCE: 77

```
ccccttcacc ggatccttcg atccacgttt ccacgaaaac                           40
```

<210> SEQ ID NO 78
<211> LENGTH: 40
<212> TYPE: DNA
<213> ORGANISM: Artificial sequence
<220> FEATURE:
<223> OTHER INFORMATION: primer

<400> SEQUENCE: 78

```
ccccttcacc ggatccccag atccacgttt ccacgaaaac                           40
```

<210> SEQ ID NO 79
<211> LENGTH: 40
<212> TYPE: DNA
<213> ORGANISM: Artificial sequence
<220> FEATURE:
<223> OTHER INFORMATION: primer

<400> SEQUENCE: 79

```
ccccttcacc ggatcctccg atccacgttt ccacgaaaac                           40
```

<210> SEQ ID NO 80
<211> LENGTH: 40
<212> TYPE: DNA
<213> ORGANISM: Artificial sequence
<220> FEATURE:
<223> OTHER INFORMATION: primer

<400> SEQUENCE: 80

```
ccccttcacc ggatccaccg atccacgttt ccacgaaaac                           40
```

<210> SEQ ID NO 81
<211> LENGTH: 40
<212> TYPE: DNA
<213> ORGANISM: Artificial sequence
<220> FEATURE:

<223> OTHER INFORMATION: primer

<400> SEQUENCE: 81
ccccttcacc ggatcctggg atccacgttt ccacgaaaac        40

<210> SEQ ID NO 82
<211> LENGTH: 39
<212> TYPE: DNA
<213> ORGANISM: Artificial sequence
<220> FEATURE:
<223> OTHER INFORMATION: primer

<400> SEQUENCE: 82
ccccttcacc ggatcctacg atccacgttt ccacgaaac         39

<210> SEQ ID NO 83
<211> LENGTH: 40
<212> TYPE: DNA
<213> ORGANISM: Artificial sequence
<220> FEATURE:
<223> OTHER INFORMATION: primer

<400> SEQUENCE: 83
ccccttcacc ggatccgttg atccacgttt ccacgaaaac        40

<210> SEQ ID NO 84
<211> LENGTH: 40
<212> TYPE: DNA
<213> ORGANISM: Artificial sequence
<220> FEATURE:
<223> OTHER INFORMATION: primer

<400> SEQUENCE: 84
gttttcgtgg aaacgtggat cggcggatcc ggtgaagggg        40

<210> SEQ ID NO 85
<211> LENGTH: 40
<212> TYPE: DNA
<213> ORGANISM: Artificial sequence
<220> FEATURE:
<223> OTHER INFORMATION: primer

<400> SEQUENCE: 85
gttttcgtgg aaacgtggat cacgggatcc ggtgaagggg        40

<210> SEQ ID NO 86
<211> LENGTH: 40
<212> TYPE: DNA
<213> ORGANISM: Artificial sequence
<220> FEATURE:
<223> OTHER INFORMATION: primer

<400> SEQUENCE: 86
gttttcgtgg aaacgtggat cgttggatcc ggtgaagggg        40

<210> SEQ ID NO 87
<211> LENGTH: 40
<212> TYPE: DNA
<213> ORGANISM: Artificial sequence
<220> FEATURE:
<223> OTHER INFORMATION: primer

<400> SEQUENCE: 87
gttttcgtgg aaacgtggat catcggatcc ggtgaagggg        40

<210> SEQ ID NO 88

```
<211> LENGTH: 40
<212> TYPE: DNA
<213> ORGANISM: Artificial sequence
<220> FEATURE:
<223> OTHER INFORMATION: primer

<400> SEQUENCE: 88
gttttcgtgg aaacgtggat ccaaggatcc ggtgaagggg                           40

<210> SEQ ID NO 89
<211> LENGTH: 40
<212> TYPE: DNA
<213> ORGANISM: Artificial sequence
<220> FEATURE:
<223> OTHER INFORMATION: primer

<400> SEQUENCE: 89
gttttcgtgg aaacgtggat cctgggatcc ggtgaagggg                           40

<210> SEQ ID NO 90
<211> LENGTH: 40
<212> TYPE: DNA
<213> ORGANISM: Artificial sequence
<220> FEATURE:
<223> OTHER INFORMATION: Primer for modification of DP

<400> SEQUENCE: 90
gttttcgtgg aaacgtggat cttcggatcc ggtgaagggg                           40

<210> SEQ ID NO 91
<211> LENGTH: 40
<212> TYPE: DNA
<213> ORGANISM: Artificial sequence
<220> FEATURE:
<223> OTHER INFORMATION: primer

<400> SEQUENCE: 91
gttttcgtgg aaacgtggat ctccggatcc ggtgaagggg                           40

<210> SEQ ID NO 92
<211> LENGTH: 40
<212> TYPE: DNA
<213> ORGANISM: Artificial sequence
<220> FEATURE:
<223> OTHER INFORMATION: primer

<400> SEQUENCE: 92
gttttcgtgg aaacgtggat cgtgggatcc ggtgaagggg                           40

<210> SEQ ID NO 93
<211> LENGTH: 40
<212> TYPE: DNA
<213> ORGANISM: Artificial sequence
<220> FEATURE:
<223> OTHER INFORMATION: primer

<400> SEQUENCE: 93
gttttcgtgg aaacgtggat cgagggatcc ggtgaagggg                           40

<210> SEQ ID NO 94
<211> LENGTH: 40
<212> TYPE: DNA
<213> ORGANISM: Artificial sequence
<220> FEATURE:
<223> OTHER INFORMATION: primer

<400> SEQUENCE: 94
```
gttttcgtgg aaacgtggat ctttggatcc ggtgaagggg                40

<210> SEQ ID NO 95
<211> LENGTH: 40
<212> TYPE: DNA
<213> ORGANISM: Artificial sequence
<220> FEATURE:
<223> OTHER INFORMATION: primer

<400> SEQUENCE: 95
gttttcgtgg aaacgtggat ccatggatcc ggtgaagggg                40

<210> SEQ ID NO 96
<211> LENGTH: 40
<212> TYPE: DNA
<213> ORGANISM: Artificial sequence
<220> FEATURE:
<223> OTHER INFORMATION: primer

<400> SEQUENCE: 96
gttttcgtgg aaacgtggat cgaaggatcc ggtgaagggg                40

<210> SEQ ID NO 97
<211> LENGTH: 40
<212> TYPE: DNA
<213> ORGANISM: Artificial sequence
<220> FEATURE:
<223> OTHER INFORMATION: primer

<400> SEQUENCE: 97
gttttcgtgg aaacgtggat ctggggatcc ggtgaagggg                40

<210> SEQ ID NO 98
<211> LENGTH: 40
<212> TYPE: DNA
<213> ORGANISM: Artificial sequence
<220> FEATURE:
<223> OTHER INFORMATION: primer

<400> SEQUENCE: 98
gttttcgtgg aaacgtggat cggaggatcc ggtgaagggg                40

<210> SEQ ID NO 99
<211> LENGTH: 40
<212> TYPE: DNA
<213> ORGANISM: Artificial sequence
<220> FEATURE:
<223> OTHER INFORMATION: primer

<400> SEQUENCE: 99
gttttcgtgg aaacgtggat cggtggatcc ggtgaagggg                40

<210> SEQ ID NO 100
<211> LENGTH: 40
<212> TYPE: DNA
<213> ORGANISM: Artificial sequence
<220> FEATURE:
<223> OTHER INFORMATION: primer

<400> SEQUENCE: 100
gttttcgtgg aaacgtggat cccaggatcc ggtgaagggg                40

<210> SEQ ID NO 101
<211> LENGTH: 40
<212> TYPE: DNA
<213> ORGANISM: Artificial sequence
<220> FEATURE:

<223> OTHER INFORMATION: primer

<400> SEQUENCE: 101
gttttcgtgg aaacgtggat cgtaggatcc ggtgaagggg                    40

<210> SEQ ID NO 102
<211> LENGTH: 40
<212> TYPE: DNA
<213> ORGANISM: Artificial sequence
<220> FEATURE:
<223> OTHER INFORMATION: primer

<400> SEQUENCE: 102
gttttcgtgg aaacgtggat caacggatcc ggtgaagggg                    40

<210> SEQ ID NO 103
<211> LENGTH: 45
<212> TYPE: DNA
<213> ORGANISM: Artificial sequence
<220> FEATURE:
<223> OTHER INFORMATION: primer

<400> SEQUENCE: 103
catcgatcca gatccagatc caccacgttt ccacgaaaac tggcc             45

<210> SEQ ID NO 104
<211> LENGTH: 45
<212> TYPE: DNA
<213> ORGANISM: Artificial sequence
<220> FEATURE:
<223> OTHER INFORMATION: primer

<400> SEQUENCE: 104
ggccagtttt cgtggaaacg tggtggatct ggatctggat cgatg             45

<210> SEQ ID NO 105
<211> LENGTH: 47
<212> TYPE: DNA
<213> ORGANISM: Artificial sequence
<220> FEATURE:
<223> OTHER INFORMATION: primer

<400> SEQUENCE: 105
catcgatcca gatccaccag atccaccacg tttccacgaa aactggc           47

<210> SEQ ID NO 106
<211> LENGTH: 47
<212> TYPE: DNA
<213> ORGANISM: Artificial sequence
<220> FEATURE:
<223> OTHER INFORMATION: primer

<400> SEQUENCE: 106
gccagttttc gtggaaacgt ggtggatctg gtggatctgg atcgatg           47

<210> SEQ ID NO 107
<211> LENGTH: 44
<212> TYPE: DNA
<213> ORGANISM: Artificial sequence
<220> FEATURE:
<223> OTHER INFORMATION: primer

<400> SEQUENCE: 107
gatccatcga tccagatcca ccagatccac gtttccacga aaac              44

<210> SEQ ID NO 108

```
<211> LENGTH: 44
<212> TYPE: DNA
<213> ORGANISM: Artificial sequence
<220> FEATURE:
<223> OTHER INFORMATION: primer

<400> SEQUENCE: 108
gttttcgtgg aaacgtggat ctggtggatc tggatcgatg gatc                    44

<210> SEQ ID NO 109
<211> LENGTH: 52
<212> TYPE: DNA
<213> ORGANISM: Artificial sequence
<220> FEATURE:
<223> OTHER INFORMATION: primer

<400> SEQUENCE: 109
caccggatcc atcgatccac cagatccacc agatccacgt ttccacgaaa ac           52

<210> SEQ ID NO 110
<211> LENGTH: 52
<212> TYPE: DNA
<213> ORGANISM: Artificial sequence
<220> FEATURE:
<223> OTHER INFORMATION: primer

<400> SEQUENCE: 110
gttttcgtgg aaacgtggat ctggtggatc tggtggatcg atggatccgg tg           52

<210> SEQ ID NO 111
<211> LENGTH: 12
<212> TYPE: PRT
<213> ORGANISM: artificial sequence
<220> FEATURE:
<223> OTHER INFORMATION: Hair-binding peptide

<400> SEQUENCE: 111

Arg Val Pro Asn Lys Thr Val Thr Val Asp Gly Ala
1               5                   10

<210> SEQ ID NO 112
<211> LENGTH: 12
<212> TYPE: PRT
<213> ORGANISM: artificial sequence
<220> FEATURE:
<223> OTHER INFORMATION: Hair-binding peptide

<400> SEQUENCE: 112

Asp Arg His Lys Ser Lys Tyr Ser Ser Thr Lys Ser
1               5                   10

<210> SEQ ID NO 113
<211> LENGTH: 12
<212> TYPE: PRT
<213> ORGANISM: artificial sequence
<220> FEATURE:
<223> OTHER INFORMATION: Hair-binding peptide

<400> SEQUENCE: 113

Lys Asn Phe Pro Gln Gln Lys Glu Phe Pro Leu Ser
1               5                   10

<210> SEQ ID NO 114
<211> LENGTH: 12
<212> TYPE: PRT
<213> ORGANISM: artificial sequence
<220> FEATURE:
<223> OTHER INFORMATION: Hair-binding peptide
```

```
<400> SEQUENCE: 114

Gln Arg Asn Ser Pro Pro Ala Met Ser Arg Arg Asp
1               5                   10

<210> SEQ ID NO 115
<211> LENGTH: 12
<212> TYPE: PRT
<213> ORGANISM: artificial sequence
<220> FEATURE:
<223> OTHER INFORMATION: Hair-binding peptide

<400> SEQUENCE: 115

Thr Arg Lys Pro Asn Met Pro His Gly Gln Tyr Leu
1               5                   10

<210> SEQ ID NO 116
<211> LENGTH: 12
<212> TYPE: PRT
<213> ORGANISM: artificial sequence
<220> FEATURE:
<223> OTHER INFORMATION: Hair-binding peptide

<400> SEQUENCE: 116

Lys Pro Pro His Leu Ala Lys Leu Pro Phe Thr Thr
1               5                   10

<210> SEQ ID NO 117
<211> LENGTH: 12
<212> TYPE: PRT
<213> ORGANISM: artificial sequence
<220> FEATURE:
<223> OTHER INFORMATION: Hair-binding peptide

<400> SEQUENCE: 117

Asn Lys Arg Pro Pro Thr Ser His Arg Ile His Ala
1               5                   10

<210> SEQ ID NO 118
<211> LENGTH: 12
<212> TYPE: PRT
<213> ORGANISM: artificial sequence
<220> FEATURE:
<223> OTHER INFORMATION: Hair-binding peptide

<400> SEQUENCE: 118

Asn Leu Pro Arg Tyr Gln Pro Pro Cys Lys Pro Leu
1               5                   10

<210> SEQ ID NO 119
<211> LENGTH: 12
<212> TYPE: PRT
<213> ORGANISM: artificial sequence
<220> FEATURE:
<223> OTHER INFORMATION: Hair-binding peptide

<400> SEQUENCE: 119

Arg Pro Pro Trp Lys Lys Pro Ile Pro Pro Ser Glu
1               5                   10

<210> SEQ ID NO 120
<211> LENGTH: 12
<212> TYPE: PRT
<213> ORGANISM: artificial sequence
<220> FEATURE:
<223> OTHER INFORMATION: Hair-binding peptide

<400> SEQUENCE: 120
```

Arg Gln Arg Pro Lys Asp His Phe Phe Ser Arg Pro
1               5                   10

<210> SEQ ID NO 121
<211> LENGTH: 12
<212> TYPE: PRT
<213> ORGANISM: artificial sequence
<220> FEATURE:
<223> OTHER INFORMATION: Hair-binding peptide
<220> FEATURE:
<221> NAME/KEY: MISC_FEATURE
<222> LOCATION: (6)..(6)
<223> OTHER INFORMATION: Xaa = Thr or Pro
<220> FEATURE:
<221> NAME/KEY: MISC_FEATURE
<222> LOCATION: (12)..(12)
<223> OTHER INFORMATION: Xaa = Thr or Pro

<400> SEQUENCE: 121

Ser Val Pro Asn Lys Xaa Val Thr Val Asp Gly Xaa
1               5                   10

<210> SEQ ID NO 122
<211> LENGTH: 13
<212> TYPE: PRT
<213> ORGANISM: artificial sequence
<220> FEATURE:
<223> OTHER INFORMATION: Skin-binding peptide

<400> SEQUENCE: 122

Thr Pro Phe His Ser Pro Glu Asn Ala Pro Gly Ser Lys
1               5                   10

<210> SEQ ID NO 123
<211> LENGTH: 16
<212> TYPE: PRT
<213> ORGANISM: artificial sequence
<220> FEATURE:
<223> OTHER INFORMATION: Skin-binding peptide

<400> SEQUENCE: 123

Thr Pro Phe His Ser Pro Glu Asn Ala Pro Gly Ser Gly Gly Gly Ser
1               5                   10                  15

<210> SEQ ID NO 124
<211> LENGTH: 17
<212> TYPE: PRT
<213> ORGANISM: artificial sequence
<220> FEATURE:
<223> OTHER INFORMATION: Skin-binding peptide

<400> SEQUENCE: 124

Thr Pro Phe His Ser Pro Glu Asn Ala Pro Gly Ser Gly Gly Gly Ser
1               5                   10                  15

Ser

<210> SEQ ID NO 125
<211> LENGTH: 15
<212> TYPE: PRT
<213> ORGANISM: artificial sequence
<220> FEATURE:
<223> OTHER INFORMATION: Skin-binding peptide

<400> SEQUENCE: 125

Thr Pro Phe His Ser Pro Glu Asn Ala Pro Gly Ser Gly Gly Gly
1               5                   10                  15

```
<210> SEQ ID NO 126
<211> LENGTH: 7
<212> TYPE: PRT
<213> ORGANISM: artificial sequence
<220> FEATURE:
<223> OTHER INFORMATION: Skin-binding peptide

<400> SEQUENCE: 126

Phe Thr Gln Ser Leu Pro Arg
1               5

<210> SEQ ID NO 127
<211> LENGTH: 12
<212> TYPE: PRT
<213> ORGANISM: artificial sequence
<220> FEATURE:
<223> OTHER INFORMATION: Skin-binding peptide

<400> SEQUENCE: 127

Lys Gln Ala Thr Phe Pro Pro Asn Pro Thr Ala Tyr
1               5                   10

<210> SEQ ID NO 128
<211> LENGTH: 12
<212> TYPE: PRT
<213> ORGANISM: artificial sequence
<220> FEATURE:
<223> OTHER INFORMATION: Skin-binding peptide

<400> SEQUENCE: 128

His Gly His Met Val Ser Thr Ser Gln Leu Ser Ile
1               5                   10

<210> SEQ ID NO 129
<211> LENGTH: 7
<212> TYPE: PRT
<213> ORGANISM: artificial sequence
<220> FEATURE:
<223> OTHER INFORMATION: Skin-binding peptide

<400> SEQUENCE: 129

Leu Ser Pro Ser Arg Met Lys
1               5

<210> SEQ ID NO 130
<211> LENGTH: 7
<212> TYPE: PRT
<213> ORGANISM: artificial sequence
<220> FEATURE:
<223> OTHER INFORMATION: Skin-binding peptide

<400> SEQUENCE: 130

Leu Pro Ile Pro Arg Met Lys
1               5

<210> SEQ ID NO 131
<211> LENGTH: 7
<212> TYPE: PRT
<213> ORGANISM: artificial sequence
<220> FEATURE:
<223> OTHER INFORMATION: Skin-binding peptide

<400> SEQUENCE: 131

His Gln Arg Pro Tyr Leu Thr
1               5

<210> SEQ ID NO 132
<211> LENGTH: 7
```

```
<212> TYPE: PRT
<213> ORGANISM: artificial sequence
<220> FEATURE:
<223> OTHER INFORMATION: Skin-binding peptide

<400> SEQUENCE: 132

Phe Pro Pro Leu Leu Arg Leu
1               5

<210> SEQ ID NO 133
<211> LENGTH: 12
<212> TYPE: PRT
<213> ORGANISM: artificial sequence
<220> FEATURE:
<223> OTHER INFORMATION: Nail binding peptide

<400> SEQUENCE: 133

Ala Leu Pro Arg Ile Ala Asn Thr Trp Ser Pro Ser
1               5                   10

<210> SEQ ID NO 134
<211> LENGTH: 12
<212> TYPE: PRT
<213> ORGANISM: artificial sequence
<220> FEATURE:
<223> OTHER INFORMATION: Nail binding peptide

<400> SEQUENCE: 134

Tyr Pro Ser Phe Ser Pro Thr Tyr Arg Pro Ala Phe
1               5                   10

<210> SEQ ID NO 135
<211> LENGTH: 14
<212> TYPE: PRT
<213> ORGANISM: artificial sequence
<220> FEATURE:
<223> OTHER INFORMATION: Tooth pellicle-binding peptide

<400> SEQUENCE: 135

Asp Glu Cys Met Glu Pro Leu Asn Ala Ala His Cys Trp Arg
1               5                   10

<210> SEQ ID NO 136
<211> LENGTH: 14
<212> TYPE: PRT
<213> ORGANISM: artificial sequence
<220> FEATURE:
<223> OTHER INFORMATION: Tooth pellicle-binding peptide

<400> SEQUENCE: 136

Asp Glu Cys Met His Gly Ser Asp Val Glu Phe Cys Thr Ser
1               5                   10

<210> SEQ ID NO 137
<211> LENGTH: 14
<212> TYPE: PRT
<213> ORGANISM: artificial sequence
<220> FEATURE:
<223> OTHER INFORMATION: Tooth pellicle-binding peptide

<400> SEQUENCE: 137

Asp Leu Cys Ser Met Gln Met Met Asn Thr Gly Cys His Tyr
1               5                   10

<210> SEQ ID NO 138
<211> LENGTH: 14
<212> TYPE: PRT
<213> ORGANISM: artificial sequence
```

```
<220> FEATURE:
<223> OTHER INFORMATION: Tooth pellicle-binding peptide

<400> SEQUENCE: 138

Asp Leu Cys Ser Ser Pro Ser Thr Trp Gly Ser Cys Ile Arg
1               5                   10

<210> SEQ ID NO 139
<211> LENGTH: 20
<212> TYPE: PRT
<213> ORGANISM: artificial sequence
<220> FEATURE:
<223> OTHER INFORMATION: Tooth pellicle-binding peptide

<400> SEQUENCE: 139

Asp Pro Asn Glu Ser Asn Tyr Glu Asn Ala Thr Thr Val Ser Gln Pro
1               5                   10                  15

Thr Arg His Leu
            20

<210> SEQ ID NO 140
<211> LENGTH: 20
<212> TYPE: PRT
<213> ORGANISM: artificial sequence
<220> FEATURE:
<223> OTHER INFORMATION: Tooth pellicle-binding peptide

<400> SEQUENCE: 140

Glu Pro Thr His Pro Thr Met Arg Ala Gln Met His Gln Ser Leu Arg
1               5                   10                  15

Ser Ser Ser Pro
            20

<210> SEQ ID NO 141
<211> LENGTH: 20
<212> TYPE: PRT
<213> ORGANISM: artificial sequence
<220> FEATURE:
<223> OTHER INFORMATION: Tooth pellicle-binding peptide

<400> SEQUENCE: 141

Gly Asn Thr Asp Thr Thr Pro Pro Asn Ala Val Met Glu Pro Thr Val
1               5                   10                  15

Gln His Lys Trp
            20

<210> SEQ ID NO 142
<211> LENGTH: 15
<212> TYPE: PRT
<213> ORGANISM: artificial sequence
<220> FEATURE:
<223> OTHER INFORMATION: Tooth pellicle-binding peptide

<400> SEQUENCE: 142

Asn Gly Pro Asp Met Val Gln Ser Val Gly Lys His Lys Asn Ser
1               5                   10                  15

<210> SEQ ID NO 143
<211> LENGTH: 15
<212> TYPE: PRT
<213> ORGANISM: artificial sequence
<220> FEATURE:
<223> OTHER INFORMATION: Tooth pellicle-binding peptide

<400> SEQUENCE: 143

Asn Gly Pro Glu Val Arg Gln Ile Pro Ala Asn Phe Glu Lys Leu
```

-continued

<210> SEQ ID NO 144
<211> LENGTH: 20
<212> TYPE: PRT
<213> ORGANISM: artificial sequence
<220> FEATURE:
<223> OTHER INFORMATION: Tooth enamel-binding peptide

<400> SEQUENCE: 144

Trp Cys Thr Asp Phe Cys Thr Arg Ser Thr Pro Thr Ser Thr Ser Arg
1               5                   10                  15

Ser Thr Thr Ser
            20

<210> SEQ ID NO 145
<211> LENGTH: 20
<212> TYPE: PRT
<213> ORGANISM: artificial sequence
<220> FEATURE:
<223> OTHER INFORMATION: Tooth enamel-binding peptide

<400> SEQUENCE: 145

Ala Pro Pro Leu Lys Thr Tyr Met Gln Glu Arg Glu Leu Thr Met Ser
1               5                   10                  15

Gln Asn Lys Asp
            20

<210> SEQ ID NO 146
<211> LENGTH: 20
<212> TYPE: PRT
<213> ORGANISM: artificial sequence
<220> FEATURE:
<223> OTHER INFORMATION: Tooth enamel-binding peptide

<400> SEQUENCE: 146

Glu Pro Pro Thr Arg Thr Arg Val Asn Asn His Thr Val Thr Val Gln
1               5                   10                  15

Ala Gln Gln His
            20

<210> SEQ ID NO 147
<211> LENGTH: 14
<212> TYPE: PRT
<213> ORGANISM: artificial sequence
<220> FEATURE:
<223> OTHER INFORMATION: Tooth enamel-binding peptide

<400> SEQUENCE: 147

Gly Tyr Cys Leu Arg Gly Asp Glu Pro Ala Val Cys Ser Gly
1               5                   10

<210> SEQ ID NO 148
<211> LENGTH: 20
<212> TYPE: PRT
<213> ORGANISM: artificial sequence
<220> FEATURE:
<223> OTHER INFORMATION: Tooth enamel-binding peptide

<400> SEQUENCE: 148

Leu Ser Ser Lys Asp Phe Gly Val Thr Asn Thr Asp Gln Arg Thr Tyr
1               5                   10                  15

Asp Tyr Thr Thr
            20

```
<210> SEQ ID NO 149
<211> LENGTH: 14
<212> TYPE: PRT
<213> ORGANISM: artificial sequence
<220> FEATURE:
<223> OTHER INFORMATION: Tooth enamel-binding peptide

<400> SEQUENCE: 149

Asn Phe Cys Glu Thr Gln Leu Asp Leu Ser Val Cys Thr Val
1               5                   10

<210> SEQ ID NO 150
<211> LENGTH: 14
<212> TYPE: PRT
<213> ORGANISM: artificial sequence
<220> FEATURE:
<223> OTHER INFORMATION: Tooth enamel-binding peptide

<400> SEQUENCE: 150

Asn Thr Cys Gln Pro Thr Lys Asn Ala Thr Pro Cys Ser Ala
1               5                   10

<210> SEQ ID NO 151
<211> LENGTH: 20
<212> TYPE: PRT
<213> ORGANISM: artificial sequence
<220> FEATURE:
<223> OTHER INFORMATION: Tooth enamel-binding peptide

<400> SEQUENCE: 151

Pro Ser Glu Pro Glu Arg Arg Asp Arg Asn Ile Ala Ala Asn Ala Gly
1               5                   10                  15

Arg Phe Asn Thr
            20

<210> SEQ ID NO 152
<211> LENGTH: 18
<212> TYPE: PRT
<213> ORGANISM: artificial sequence
<220> FEATURE:
<223> OTHER INFORMATION: Tooth enamel-binding peptide

<400> SEQUENCE: 152

Thr His Asn Met Ser His Phe Pro Pro Ser Gly His Pro Lys Arg Thr
1               5                   10                  15

Ala Thr

<210> SEQ ID NO 153
<211> LENGTH: 14
<212> TYPE: PRT
<213> ORGANISM: artificial sequence
<220> FEATURE:
<223> OTHER INFORMATION: Tooth enamel-binding peptide

<400> SEQUENCE: 153

Thr Thr Cys Pro Thr Met Gly Thr Tyr His Val Cys Trp Leu
1               5                   10

<210> SEQ ID NO 154
<211> LENGTH: 20
<212> TYPE: PRT
<213> ORGANISM: artificial sequence
<220> FEATURE:
<223> OTHER INFORMATION: Tooth enamel-binding peptide

<400> SEQUENCE: 154

Tyr Cys Ala Asp His Thr Pro Asp Pro Ala Asn Pro Asn Lys Ile Cys
```

```
                1               5                  10                  15

Gly Tyr Ser His
            20

<210> SEQ ID NO 155
<211> LENGTH: 10
<212> TYPE: PRT
<213> ORGANISM: artificial sequence
<220> FEATURE:
<223> OTHER INFORMATION: Antimicrobial peptide

<400> SEQUENCE: 155

Phe Ala Lys Lys Leu Ala Lys Lys Leu Leu
1               5                  10

<210> SEQ ID NO 156
<211> LENGTH: 13
<212> TYPE: PRT
<213> ORGANISM: artificial sequence
<220> FEATURE:
<223> OTHER INFORMATION: Antimicrobial peptide

<400> SEQUENCE: 156

Phe Ala Lys Leu Leu Ala Lys Leu Ala Lys Lys Val Leu
1               5                  10

<210> SEQ ID NO 157
<211> LENGTH: 13
<212> TYPE: PRT
<213> ORGANISM: artificial sequence
<220> FEATURE:
<223> OTHER INFORMATION: Antimicrobial peptide

<400> SEQUENCE: 157

Lys Tyr Lys Lys Ala Leu Lys Lys Leu Ala Lys Leu Leu
1               5                  10

<210> SEQ ID NO 158
<211> LENGTH: 12
<212> TYPE: PRT
<213> ORGANISM: artificial sequence
<220> FEATURE:
<223> OTHER INFORMATION: Antimicrobial peptide

<400> SEQUENCE: 158

Phe Ala Leu Leu Lys Ala Leu Leu Lys Lys Ala Leu
1               5                  10

<210> SEQ ID NO 159
<211> LENGTH: 14
<212> TYPE: PRT
<213> ORGANISM: artificial sequence
<220> FEATURE:
<223> OTHER INFORMATION: Antimicrobial peptide

<400> SEQUENCE: 159

Lys Arg Leu Phe Lys Lys Leu Lys Phe Ser Leu Arg Lys Tyr
1               5                  10

<210> SEQ ID NO 160
<211> LENGTH: 14
<212> TYPE: PRT
<213> ORGANISM: artificial sequence
<220> FEATURE:
<223> OTHER INFORMATION: Antimicrobial peptide

<400> SEQUENCE: 160
```

Lys Arg Leu Phe Lys Lys Leu Leu Phe Ser Leu Arg Lys Tyr
1               5                   10

<210> SEQ ID NO 161
<211> LENGTH: 14
<212> TYPE: PRT
<213> ORGANISM: artificial sequence
<220> FEATURE:
<223> OTHER INFORMATION: Antimicrobial peptide

<400> SEQUENCE: 161

Leu Leu Leu Phe Leu Leu Lys Lys Arg Lys Lys Arg Lys Tyr
1               5                   10

<210> SEQ ID NO 162
<211> LENGTH: 27
<212> TYPE: PRT
<213> ORGANISM: artificial sequence
<220> FEATURE:
<223> OTHER INFORMATION: Clay-binding peptide

<400> SEQUENCE: 162

Gly His Gly Ser Pro Ser Asn Ser His His Gly Ser Lys Lys Cys Asp
1               5                   10                  15

Met Gly Asn Ser Arg Ala Lys Cys Lys Arg Leu
            20                  25

<210> SEQ ID NO 163
<211> LENGTH: 27
<212> TYPE: PRT
<213> ORGANISM: artificial sequence
<220> FEATURE:
<223> OTHER INFORMATION: Clay-binding peptide

<400> SEQUENCE: 163

Ser Asp Arg His Asn Leu Arg Asn Ser Trp Ser Ile Ser Arg His Cys
1               5                   10                  15

Arg Arg Lys Gln Gly Arg Cys Leu Pro Ala His
            20                  25

<210> SEQ ID NO 164
<211> LENGTH: 27
<212> TYPE: PRT
<213> ORGANISM: artificial sequence
<220> FEATURE:
<223> OTHER INFORMATION: Clay-binding peptide

<400> SEQUENCE: 164

Lys Lys Ser Asn Lys Gly His His Pro Ser Ser Lys Gly Lys Gly Pro
1               5                   10                  15

Pro Trp Ser Glu Trp Asp Lys Lys Asn Gly Pro
            20                  25

<210> SEQ ID NO 165
<211> LENGTH: 27
<212> TYPE: PRT
<213> ORGANISM: artificial sequence
<220> FEATURE:
<223> OTHER INFORMATION: Clay-binding peptide

<400> SEQUENCE: 165

Lys Lys Ser Asn Lys Gly Pro His Pro Ser Ser Lys Gly Lys Gly Pro
1               5                   10                  15

Pro Trp Ser Glu Trp Asp Lys Lys Asn Gly Pro
            20                  25

```
<210> SEQ ID NO 166
<211> LENGTH: 22
<212> TYPE: PRT
<213> ORGANISM: artificial sequence
<220> FEATURE:
<223> OTHER INFORMATION: Clay-binding peptide

<400> SEQUENCE: 166

Val Gly Arg His His Ser Lys Ala Lys Gln Lys Arg Pro His Gly Gly
1               5                   10                  15

Lys Gly Gln Asn Lys Asn
            20

<210> SEQ ID NO 167
<211> LENGTH: 22
<212> TYPE: PRT
<213> ORGANISM: artificial sequence
<220> FEATURE:
<223> OTHER INFORMATION: Clay-binding peptide

<400> SEQUENCE: 167

Val Gly Arg His His Pro Lys Ala Lys Gln Lys Arg Pro His Gly Gly
1               5                   10                  15

Lys Gly Gln Asn Lys Asn
            20

<210> SEQ ID NO 168
<211> LENGTH: 17
<212> TYPE: PRT
<213> ORGANISM: artificial sequence
<220> FEATURE:
<223> OTHER INFORMATION: Clay-binding peptide

<400> SEQUENCE: 168

Gly Arg Arg Pro Arg Ala Arg Gly Arg Ser Arg Arg Gly Ser Thr Lys
1               5                   10                  15

Thr

<210> SEQ ID NO 169
<211> LENGTH: 19
<212> TYPE: PRT
<213> ORGANISM: artificial sequence
<220> FEATURE:
<223> OTHER INFORMATION: Clay-binding peptide

<400> SEQUENCE: 169

Leu Gly Val Ile Arg Asn His Val Val Arg Gly Arg Arg His His Gln
1               5                   10                  15

His Val Arg

<210> SEQ ID NO 170
<211> LENGTH: 27
<212> TYPE: PRT
<213> ORGANISM: artificial sequence
<220> FEATURE:
<223> OTHER INFORMATION: Clay-binding peptide

<400> SEQUENCE: 170

Gln Pro Gly Arg Pro Thr Glu Val His Pro Glu Leu Val Arg Lys Ser
1               5                   10                  15

Ala Tyr Leu Val Asn Pro Ser Glu Asp Ile Arg
            20                  25

<210> SEQ ID NO 171
```

```
<211> LENGTH: 27
<212> TYPE: PRT
<213> ORGANISM: artificial sequence
<220> FEATURE:
<223> OTHER INFORMATION: Clay-binding peptide

<400> SEQUENCE: 171

His Arg Ser Glu Lys Pro Lys Asn Val Lys Tyr Lys Arg Gly Tyr Trp
1               5                   10                  15

Glu Arg Gly Asn Gln Lys Lys His Gly Pro Gly
            20                  25

<210> SEQ ID NO 172
<211> LENGTH: 27
<212> TYPE: PRT
<213> ORGANISM: artificial sequence
<220> FEATURE:
<223> OTHER INFORMATION: Clay-binding peptide

<400> SEQUENCE: 172

Gly Ser His Lys Arg Arg Gly Ser Tyr Ala Leu Leu Arg Thr Arg Gly
1               5                   10                  15

Val Gly Arg Gln Ala Glu Leu Glu His Leu Leu
            20                  25

<210> SEQ ID NO 173
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 173

Arg Asn Asn Lys Gly Ser Lys Lys Val Asp Asp Lys Arg Arg Lys Thr
1               5                   10                  15

Val His Asn Thr Lys Ser Arg Ala Lys Tyr Ser
            20                  25

<210> SEQ ID NO 174
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 174

Arg Asn Asn Lys Gly Ser Lys Lys Val Asp Asp Lys Arg Arg Lys Thr
1               5                   10                  15

Val His Asn Thr Lys Ser Arg Ala Lys His Ser
            20                  25

<210> SEQ ID NO 175
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 175

Arg Asp Asn Lys Gly Ser Lys Lys Val Asp Asp Lys Arg Arg Lys Thr
1               5                   10                  15

Val His Asn Thr Lys Ser Arg Ala Lys Tyr Ser
            20                  25

<210> SEQ ID NO 176
```

```
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 176

Arg Asn Asn Lys Gly Ser Lys Lys Val Asp Asp Lys Arg Arg Lys Thr
1               5                   10                  15

Val His Ser Thr Lys Ser Arg Ala Lys Tyr Ser
            20                  25

<210> SEQ ID NO 177
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 177

Arg Asn Asn Lys Gly Ser Arg Lys Val Asp Asp Lys Arg Arg Lys Thr
1               5                   10                  15

Val His Asn Thr Lys Ser Arg Ala Lys Tyr Ser
            20                  25

<210> SEQ ID NO 178
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 178

Arg Asn Asn Lys Gly Ser Lys Lys Ala Asp Asp Lys Arg Arg Lys Thr
1               5                   10                  15

Val His Ser Thr Lys Ser Arg Ala Lys Tyr Ser
            20                  25

<210> SEQ ID NO 179
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 179

Arg Asn Asn Lys Gly Ser Lys Lys Val Asp Asp Lys Arg Arg Lys Ala
1               5                   10                  15

Val His Asn Lys Lys Ser Arg Ala Lys Tyr Ser
            20                  25

<210> SEQ ID NO 180
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 180

Arg Asn Asn Lys Gly Ser Lys Lys Val Asp Asp Lys Arg Arg Lys Thr
1               5                   10                  15

Val His Asn Thr Arg Ser Arg Ala Lys Tyr Ser
            20                  25

<210> SEQ ID NO 181
```

```
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 181

Arg Asn Asn Lys Gly Ser Lys Lys Val Asp Asp Lys Arg Arg Lys Thr
1               5                   10                  15

Val His Asn Thr Lys Ser Arg Ala Lys Phe Ser
            20                  25

<210> SEQ ID NO 182
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 182

Gln Arg Arg Lys Leu Arg His Pro Lys Glu Lys Trp Phe Gly Trp Ser
1               5                   10                  15

Glu Lys Lys Val Ile Lys Lys Trp Ser Arg Lys
            20                  25

<210> SEQ ID NO 183
<211> LENGTH: 27
<212> TYPE: PRT
<213> ORGANISM: artificial sequence
<220> FEATURE:
<223> OTHER INFORMATION: Calcium carbonate binding peptide
<220> FEATURE:
<221> NAME/KEY: MISC_FEATURE
<222> LOCATION: (23)..(23)
<223> OTHER INFORMATION: Xaa = any naturally occurring amino acid

<400> SEQUENCE: 183

Gln Arg Arg Lys Phe Arg His Pro Lys Glu Lys Trp Phe Gly Trp Ser
1               5                   10                  15

Glu Lys Lys Val Ile Lys Xaa Asn Gly Arg Pro
            20                  25

<210> SEQ ID NO 184
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 184

His Lys Arg Leu Val Gln Asn Lys Pro His Arg Thr Arg Lys Ile Glu
1               5                   10                  15

Gly Trp Ile Lys His Met Val Lys Arg Gln His
            20                  25

<210> SEQ ID NO 185
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 185

Thr Arg Gly His Ile Met Arg Pro Cys Trp Ile Gly Ala Met Lys Gln
1               5                   10                  15

Gly Val Lys Lys Lys Arg Thr Pro Gly Trp Arg
```

20          25

<210> SEQ ID NO 186
<211> LENGTH: 12
<212> TYPE: PRT
<213> ORGANISM: Artificial sequence
<220> FEATURE:
<223> OTHER INFORMATION: Polypropylene-binding peptides

<400> SEQUENCE: 186

Thr Ser Asp Ile Lys Ser Arg Ser Pro His His Arg
1               5                   10

<210> SEQ ID NO 187
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 187

His Thr Gln Asn Met Arg Met Tyr Glu Pro Trp Phe
1               5                   10

<210> SEQ ID NO 188
<211> LENGTH: 7
<212> TYPE: PRT
<213> ORGANISM: Artificial Sequence
<220> FEATURE:
<223> OTHER INFORMATION: Polypropylene-binding peptide

<400> SEQUENCE: 188

Leu Pro Pro Gly Ser Leu Ala
1               5

<210> SEQ ID NO 189
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 189

Met Pro Ala Val Met Ser Ser Ala Gln Val Pro Arg
1               5                   10

<210> SEQ ID NO 190
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 190

Asn Gln Ser Phe Leu Pro Leu Asp Phe Pro Phe Arg
1               5                   10

<210> SEQ ID NO 191
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 191

Ser Ile Leu Ser Thr Met Ser Pro His Gly Ala Thr
1               5                   10

```
<210> SEQ ID NO 192
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 192

Ser Met Lys Tyr Ser His Ser Thr Ala Pro Ala Leu
1               5                   10

<210> SEQ ID NO 193
<211> LENGTH: 12
<212> TYPE: PRT
<213> ORGANISM: Artificial sequence
<220> FEATURE:
<223> OTHER INFORMATION: Polytetrafluoroethylene-binding peptides

<400> SEQUENCE: 193

Glu Ser Ser Tyr Ser Trp Ser Pro Ala Arg Leu Ser
1               5                   10

<210> SEQ ID NO 194
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 194

Gly Pro Leu Lys Leu Leu His Ala Trp Trp Gln Pro
1               5                   10

<210> SEQ ID NO 195
<211> LENGTH: 7
<212> TYPE: PRT
<213> ORGANISM: Artificial Sequence
<220> FEATURE:
<223> OTHER INFORMATION: Polytetrafluoroethylene-binding peptide

<400> SEQUENCE: 195

Asn Ala Leu Thr Arg Pro Val
1               5

<210> SEQ ID NO 196
<211> LENGTH: 7
<212> TYPE: PRT
<213> ORGANISM: Artificial Sequence
<220> FEATURE:
<223> OTHER INFORMATION: Polytetrafluoroethylene-binding peptide

<400> SEQUENCE: 196

Ser Ala Pro Ser Ser Lys Asn
1               5

<210> SEQ ID NO 197
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 197

Ser Val Ser Val Gly Met Lys Pro Ser Pro Arg Pro
1               5                   10

<210> SEQ ID NO 198
```

```
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 198

Ser Tyr Tyr Ser Leu Pro Pro Ile Phe His Ile Pro
1               5                   10

<210> SEQ ID NO 199
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 199

Thr Phe Thr Pro Tyr Ser Ile Thr His Ala Leu Leu
1               5                   10

<210> SEQ ID NO 200
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 200

Thr Met Gly Phe Thr Ala Pro Arg Phe Pro His Tyr
1               5                   10

<210> SEQ ID NO 201
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 201

Thr Asn Pro Phe Pro Pro Pro Ser Ser Pro Ala
1               5                   10

<210> SEQ ID NO 202
<211> LENGTH: 12
<212> TYPE: PRT
<213> ORGANISM: Artificial sequence
<220> FEATURE:
<223> OTHER INFORMATION: Polyethylene-binding peptides

<400> SEQUENCE: 202

His Asn Lys Ser Ser Pro Leu Thr Ala Ala Leu Pro
1               5                   10

<210> SEQ ID NO 203
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 203

Leu Pro Pro Trp Lys His Lys Thr Ser Gly Val Ala
1               5                   10

<210> SEQ ID NO 204
<211> LENGTH: 12
<212> TYPE: PRT
```

```
<213> ORGANISM: Artificial Sequence
<220> FEATURE:
<223> OTHER INFORMATION: Polyethylene-binding peptide

<400> SEQUENCE: 204

Leu Pro Trp Trp Leu Arg Asp Ser Tyr Leu Leu Pro
1               5                   10

<210> SEQ ID NO 205
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 205

Val Pro Trp Trp Lys His Pro Pro Leu Pro Val Pro
1               5                   10

<210> SEQ ID NO 206
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 206

His His Lys Gln Trp His Asn His Pro His His Ala
1               5                   10

<210> SEQ ID NO 207
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 207

His Ile Phe Ser Ser Trp His Gln Met Trp His Arg
1               5                   10

<210> SEQ ID NO 208
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 208

Trp Pro Ala Trp Lys Thr His Pro Ile Leu Arg Met
1               5                   10

<210> SEQ ID NO 209
<211> LENGTH: 7
<212> TYPE: PRT
<213> ORGANISM: Artificial sequence
<220> FEATURE:
<223> OTHER INFORMATION: Nylon-binding peptides

<400> SEQUENCE: 209

Lys Thr Pro Pro Thr Arg Pro
1               5

<210> SEQ ID NO 210
<211> LENGTH: 7
<212> TYPE: PRT
<213> ORGANISM: Artificial Sequence
<220> FEATURE:
```

```
<223> OTHER INFORMATION: Nylon-binding peptide

<400> SEQUENCE: 210

Val Ile Asn Pro Asn Leu Asp
1               5

<210> SEQ ID NO 211
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 211

Lys Val Trp Ile Val Ser Thr
1               5

<210> SEQ ID NO 212
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 212

Ala Glu Pro Val Ala Met Leu
1               5

<210> SEQ ID NO 213
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 213

Ala Glu Leu Val Ala Met Leu
1               5

<210> SEQ ID NO 214
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 214

His Ser Leu Arg Leu Asp Trp
1               5

<210> SEQ ID NO 215
<211> LENGTH: 13
<212> TYPE: PRT
<213> ORGANISM: Artificial sequence
<220> FEATURE:
<223> OTHER INFORMATION: Polystyrene-binding peptide

<400> SEQUENCE: 215

Thr Ser Thr Ala Ser Pro Thr Met Gln Ser Lys Ile Arg
1               5                   10

<210> SEQ ID NO 216
<211> LENGTH: 12
<212> TYPE: PRT
<213> ORGANISM: Artificial Sequence
<220> FEATURE:
<223> OTHER INFORMATION: Polystyrene-binding peptide
```

```
<400> SEQUENCE: 216

Lys Arg Asn His Trp Gln Arg Met His Leu Ser Ala
1               5                   10

<210> SEQ ID NO 217
<211> LENGTH: 12
<212> TYPE: PRT
<213> ORGANISM: Artificial Sequence
<220> FEATURE:
<223> OTHER INFORMATION: Polystyrene-binding peptide

<400> SEQUENCE: 217

Ser His Ala Thr Pro Pro Gln Gly Leu Gly Pro Gln
1               5                   10

<210> SEQ ID NO 218
<211> LENGTH: 20
<212> TYPE: PRT
<213> ORGANISM: artificial sequence
<220> FEATURE:
<223> OTHER INFORMATION: cellulose acetate-binding peptide

<400> SEQUENCE: 218

Ala Thr Thr Pro Pro Ser Gly Lys Ala Ala Ala His Ser Ala Ala Arg
1               5                   10                  15

Gln Lys Gly Asn
            20

<210> SEQ ID NO 219
<211> LENGTH: 15
<212> TYPE: PRT
<213> ORGANISM: artificial sequence
<220> FEATURE:
<223> OTHER INFORMATION: cellulose acetate-binding peptide

<400> SEQUENCE: 219

Asp Thr Ile His Pro Asn Lys Met Lys Ser Pro Ser Ser Pro Leu
1               5                   10                  15

<210> SEQ ID NO 220
<211> LENGTH: 20
<212> TYPE: PRT
<213> ORGANISM: artificial sequence
<220> FEATURE:
<223> OTHER INFORMATION: cellulose aceteate-binding peptide

<400> SEQUENCE: 220

Asn Gly Asn Asn His Thr Asp Ile Pro Asn Arg Ser Ser Tyr Thr Gly
1               5                   10                  15

Gly Ser Phe Ala
            20

<210> SEQ ID NO 221
<211> LENGTH: 15
<212> TYPE: PRT
<213> ORGANISM: ARTIFICIAL SEQUENCE
<220> FEATURE:
<223> OTHER INFORMATION: synthetic cellulose acetate-binding peptide

<400> SEQUENCE: 221

Ser Asp Glu Thr Gly Pro Gln Ile Pro His Arg Arg Pro Thr Trp
1               5                   10                  15

<210> SEQ ID NO 222
<211> LENGTH: 12
<212> TYPE: PRT
```

<213> ORGANISM: Artificial Sequence
<220> FEATURE:
<223> OTHER INFORMATION: Carbon black Binding Peptide

<400> SEQUENCE: 222

Ser Val Ser Val Gly Met Lys Pro Ser Pro Arg Pro
1               5                   10

<210> SEQ ID NO 223
<211> LENGTH: 7
<212> TYPE: PRT
<213> ORGANISM: Artificial Sequence
<220> FEATURE:
<223> OTHER INFORMATION: Carbon black Binding and Cellulose Binding
      Peptide

<400> SEQUENCE: 223

Phe His Glu Asn Trp Pro Ser
1               5

<210> SEQ ID NO 224
<211> LENGTH: 7
<212> TYPE: PRT
<213> ORGANISM: Artificial Sequence
<220> FEATURE:
<223> OTHER INFORMATION: Carbon black Binding Peptide

<400> SEQUENCE: 224

Met Pro Pro Pro Leu Met Gln
1               5

<210> SEQ ID NO 225
<211> LENGTH: 12
<212> TYPE: PRT
<213> ORGANISM: Artificial Sequence
<220> FEATURE:
<223> OTHER INFORMATION: Carbon black Binding Peptide

<400> SEQUENCE: 225

Arg Thr Ala Pro Thr Thr Pro Leu Leu Leu Ser Leu
1               5                   10

<210> SEQ ID NO 226
<211> LENGTH: 7
<212> TYPE: PRT
<213> ORGANISM: Artificial Sequence
<220> FEATURE:
<223> OTHER INFORMATION: Cromophtal yellow binding peptide

<400> SEQUENCE: 226

Pro His Ala Arg Leu Val Gly
1               5

<210> SEQ ID NO 227
<211> LENGTH: 7
<212> TYPE: PRT
<213> ORGANISM: Artificial Sequence
<220> FEATURE:
<223> OTHER INFORMATION: Cromophtal yellow Binding Peptide

<400> SEQUENCE: 227

Asn Ile Pro Tyr His His Pro
1               5

<210> SEQ ID NO 228
<211> LENGTH: 7
<212> TYPE: PRT
<213> ORGANISM: Artificial Sequence

```
<220> FEATURE:
<223> OTHER INFORMATION: Cromophtal yellow Binding Peptide

<400> SEQUENCE: 228

Thr Thr Met Pro Ala Ile Pro
1               5

<210> SEQ ID NO 229
<211> LENGTH: 7
<212> TYPE: PRT
<213> ORGANISM: Artificial Sequence
<220> FEATURE:
<223> OTHER INFORMATION: Cromophtal yellow Binding Peptide

<400> SEQUENCE: 229

His Asn Leu Pro Pro Arg Ser
1               5

<210> SEQ ID NO 230
<211> LENGTH: 12
<212> TYPE: PRT
<213> ORGANISM: Artificial Sequence
<220> FEATURE:
<223> OTHER INFORMATION: Cromophtal yellow Binding Peptide

<400> SEQUENCE: 230

Ala His Lys Thr Gln Met Gly Val Arg Gln Pro Ala
1               5                   10

<210> SEQ ID NO 231
<211> LENGTH: 7
<212> TYPE: PRT
<213> ORGANISM: Artificial Sequence
<220> FEATURE:
<223> OTHER INFORMATION: Sunfast Magenta Binding Peptide

<400> SEQUENCE: 231

Tyr Pro Asn Thr Ala Leu Val
1               5

<210> SEQ ID NO 232
<211> LENGTH: 7
<212> TYPE: PRT
<213> ORGANISM: Artificial Sequence
<220> FEATURE:
<223> OTHER INFORMATION: Sunfast Magenta Binding Peptide

<400> SEQUENCE: 232

Val Ala Thr Arg Ile Val Ser
1               5

<210> SEQ ID NO 233
<211> LENGTH: 12
<212> TYPE: PRT
<213> ORGANISM: Artificial Sequence
<220> FEATURE:
<223> OTHER INFORMATION: Sunfast Magenta Binding Peptide

<400> SEQUENCE: 233

His Ser Leu Lys Asn Ser Met Leu Thr Val Met Ala
1               5                   10

<210> SEQ ID NO 234
<211> LENGTH: 7
<212> TYPE: PRT
<213> ORGANISM: Artificial Sequence
<220> FEATURE:
<223> OTHER INFORMATION: Sunfast Magenta Binding Peptide
```

<400> SEQUENCE: 234

Asn Tyr Pro Thr Gln Ala Pro
1               5

<210> SEQ ID NO 235
<211> LENGTH: 7
<212> TYPE: PRT
<213> ORGANISM: Artificial Sequence
<220> FEATURE:
<223> OTHER INFORMATION: Sunfast Magenta Binding Peptide

<400> SEQUENCE: 235

Lys Cys Cys Tyr Ser Val Gly
1               5

<210> SEQ ID NO 236
<211> LENGTH: 22
<212> TYPE: PRT
<213> ORGANISM: Artificial Sequence
<220> FEATURE:
<223> OTHER INFORMATION: synthetic construct

<400> SEQUENCE: 236

Ser Arg Arg Pro Arg Gln Leu Gln Gln Arg Gln Ser Arg Arg Pro Arg
1               5                   10                  15

Gln Leu Gln Gln Arg Gln
            20

<210> SEQ ID NO 237
<211> LENGTH: 16
<212> TYPE: PRT
<213> ORGANISM: Artificial Sequence
<220> FEATURE:
<223> OTHER INFORMATION: synthetic construct

<400> SEQUENCE: 237

Ser Arg Arg Pro Arg Gln Leu Gln Gln Arg Gln His His Gln Gln Gln
1               5                   10                  15

<210> SEQ ID NO 238
<211> LENGTH: 33
<212> TYPE: PRT
<213> ORGANISM: Artificial Sequence
<220> FEATURE:
<223> OTHER INFORMATION: synthetic construct

<400> SEQUENCE: 238

Ser Arg Arg Pro Arg Gln Leu Gln Gln Arg Gln Ser Arg Arg Pro Arg
1               5                   10                  15

Gln Leu Gln Gln Arg Gln Ser Arg Arg Pro Arg Gln Leu Gln Gln Arg
            20                  25                  30

Gln

<210> SEQ ID NO 239
<211> LENGTH: 11
<212> TYPE: PRT
<213> ORGANISM: Artificial Sequence
<220> FEATURE:
<223> OTHER INFORMATION: synthetic construct

<400> SEQUENCE: 239

Ser Arg Arg Pro Arg Gln Leu Gln Gln Arg Gln
1               5                   10

```
<210> SEQ ID NO 240
<211> LENGTH: 37
<212> TYPE: PRT
<213> ORGANISM: Artificial Sequence
<220> FEATURE:
<223> OTHER INFORMATION: synthetic construct

<400> SEQUENCE: 240

Ser Arg Arg Pro Arg Gln Leu Gln Gln Arg Gln Asp Pro Ser Arg Arg
1               5                   10                  15

Pro Arg Gln Leu Gln Gln Arg Gln Asp Pro Ser Arg Arg Pro Arg Gln
            20                  25                  30

Leu Gln Gln Arg Gln
        35

<210> SEQ ID NO 241
<211> LENGTH: 22
<212> TYPE: PRT
<213> ORGANISM: Artificial Sequence
<220> FEATURE:
<223> OTHER INFORMATION: synthetic construct

<400> SEQUENCE: 241

Ser Arg Arg Pro Glu Gln Leu Gln Gln Arg Gln Ser Arg Arg Pro Glu
1               5                   10                  15

Gln Leu Gln Gln Arg Gln
            20

<210> SEQ ID NO 242
<211> LENGTH: 22
<212> TYPE: PRT
<213> ORGANISM: Artificial Sequence
<220> FEATURE:
<223> OTHER INFORMATION: synthetic construct

<400> SEQUENCE: 242

Ser Arg Glu Pro Glu Gln Leu Gln Arg Gln Ser Arg Arg Pro Glu
1               5                   10                  15

Gln Leu Gln Gln Arg Gln
            20

<210> SEQ ID NO 243
<211> LENGTH: 22
<212> TYPE: PRT
<213> ORGANISM: Artificial Sequence
<220> FEATURE:
<223> OTHER INFORMATION: synthetic construct

<400> SEQUENCE: 243

Ser Arg Glu Pro Glu Gln Leu Gln Gln Arg Gln Ser Arg Glu Pro Glu
1               5                   10                  15

Gln Leu Gln Gln Arg Gln
            20

<210> SEQ ID NO 244
<211> LENGTH: 22
<212> TYPE: PRT
<213> ORGANISM: Artificial Sequence
<220> FEATURE:
<223> OTHER INFORMATION: synthetic construct

<400> SEQUENCE: 244

Ser Glu Glu Pro Glu Gln Leu Gln Gln Glu Gln Ser Arg Arg Pro Arg
1               5                   10                  15

Gln Leu Gln Gln Arg Gln
```

```
                20

<210> SEQ ID NO 245
<211> LENGTH: 22
<212> TYPE: PRT
<213> ORGANISM: Artificial Sequence
<220> FEATURE:
<223> OTHER INFORMATION: synthetic construct

<400> SEQUENCE: 245

Ser Arg Glu Pro Glu Gln Leu Gln Gln Glu Gln Ser Arg Glu Pro Glu
1               5                   10                  15

Gln Leu Gln Gln Arg Gln
            20

<210> SEQ ID NO 246
<211> LENGTH: 56
<212> TYPE: PRT
<213> ORGANISM: artificial sequence
<220> FEATURE:
<223> OTHER INFORMATION: synthetic construct

<400> SEQUENCE: 246

Met Gln Gln Arg Phe Gln Trp Gln Phe Glu Gln Gln Pro Arg Gly Gln
1               5                   10                  15

Gln Arg Phe Gln Trp Gln Phe Glu Gln Gln Pro Arg Gly Gln Gln Arg
            20                  25                  30

Phe Gln Trp Gln Phe Glu Gln Gln Pro Glu Gly Gln Gln Arg Phe Gln
        35                  40                  45

Trp Gln Phe Glu Gln Gln Gly Ser
    50                  55

<210> SEQ ID NO 247
<211> LENGTH: 50
<212> TYPE: PRT
<213> ORGANISM: artificial sequence
<220> FEATURE:
<223> OTHER INFORMATION: synthetic construct

<400> SEQUENCE: 247

Met Ala Ser Cys Gly Gln Gln Arg Phe Gln Trp Gln Phe Glu Gln Gln
1               5                   10                  15

Pro Arg Cys Gly Gln Gln Arg Phe Gln Trp Gln Phe Glu Gln Gln Pro
            20                  25                  30

Glu Cys Gly Gln Gln Arg Phe Gln Trp Gln Phe Glu Gln Gln Pro Cys
        35                  40                  45

Gly Ser
    50

<210> SEQ ID NO 248
<211> LENGTH: 64
<212> TYPE: PRT
<213> ORGANISM: artificial sequence
<220> FEATURE:
<223> OTHER INFORMATION: synthetic construct

<400> SEQUENCE: 248

Met Gln Gln Arg Phe Gln Trp Gln Phe Glu Gln Gln Pro Arg Gly Gln
1               5                   10                  15

Gln Arg Phe Gln Trp Gln Phe Glu Gln Gln Pro Arg Gly Gln Gln Arg
            20                  25                  30

Phe Gln Trp Gln Phe Glu Gln Gln Pro Glu Gly Gln Gln Arg Phe Gln
        35                  40                  45
```

```
Trp Gln Phe Glu Gln Gln Gly Ser Cys Cys Pro Gly Cys Cys Gly Ser
         50                  55                  60
```

```
<210> SEQ ID NO 249
<211> LENGTH: 63
<212> TYPE: PRT
<213> ORGANISM: artificial sequence
<220> FEATURE:
<223> OTHER INFORMATION: synthetic construct

<400> SEQUENCE: 249
```

```
Met Ala Ser Cys Gly Gln Gln Arg Phe Gln Trp Gln Phe Glu Gln Gln
1               5                   10                  15

Pro Arg Cys Gly Gln Gln Arg Phe Gln Trp Gln Phe Glu Gln Gln Pro
            20                  25                  30

Arg Cys Gly Gln Gln Arg Phe Gln Trp Gln Phe Glu Gln Gln Pro Glu
        35                  40                  45

Cys Gly Gln Gln Arg Phe Gln Trp Gln Phe Glu Gln Gln Pro Cys
    50                  55                  60
```

```
<210> SEQ ID NO 250
<211> LENGTH: 4945
<212> TYPE: DNA
<213> ORGANISM: artificial sequence
<220> FEATURE:
<223> OTHER INFORMATION: Plasmid PLX121

<400> SEQUENCE: 250
```

| | | | |
|---|---|---|---|
| agatctcgat cccgcgaaat taatacgact cactataggg agaccacaac ggtttccctc | | | 60 |
| tagaaataat tttgtttaac tttaagaagg agatatacat atgtcgtact accatcacca | | | 120 |
| tcaccatcac ctcgaatcaa caagtttgta caaaaaagca ggctccgcgg ccgccccctt | | | 180 |
| caccggatcc atcgatccac gtttccacga aaactggccg tctgccggcg gtacctctac | | | 240 |
| ttccaaagct tccaccacta cgacttctag caaaaccacc actacatcct ctaagactac | | | 300 |
| cacgactacc tccaaaacct ctactacctc tagctcctct acgggcggcg ccactcacaa | | | 360 |
| gacctctact cagcgtctgc tggctgcata atgaaagggt gggcgcgccg acccagcttt | | | 420 |
| cttgtacaaa gtggttgatt cgaggctgct aacaaagccc gaaaggaagc tgagttggct | | | 480 |
| gctgccaccg ctgagcaata actagcataa ccccttgggg cctctaaacg ggtcttgagg | | | 540 |
| ggttttttgc tgaaaggagg aactatatcc ggatatccac aggacgggtg tggtcgccat | | | 600 |
| gatcgcgtag tcgatagtgg ctccaagtag cgaagcgagc aggactgggc ggcggccaaa | | | 660 |
| gcggtcggac agtgctccga gaacgggtgc gcatagaaat tgcatcaacg catatagcgc | | | 720 |
| tagcagcacg ccatagtgac tggcgatgct gtcggaatgg acgatatccc gcaagaggcc | | | 780 |
| cggcagtacc ggcataacca agcctatgcc tacagcatcc agggtgacgg tgccgaggat | | | 840 |
| gacgatgagc gcattgttag atttcataca cggtgcctga ctgcgttagc aatttaactg | | | 900 |
| tgataaacta ccgcattaaa gcttatcgat gataagctgt caaacatgag aattcttgaa | | | 960 |
| gacgaaaggg cctcgtgata cgcctatttt tataggttaa tgtcatgata taatggtttt | | | 1020 |
| cttagacgtc aggtggcact tttcggggaa atgtgcgcgg aacccctatt tgtttatttt | | | 1080 |
| tctaaataca ttcaaatatg tatccgctca tgagacaata accctgataa atgcttcaat | | | 1140 |
| aatattgaaa aggaagagt atgagtattc aacatttccg tgtcgccctt attccctttt | | | 1200 |
| ttgcggcatt ttgccttcct gttttgctc acccagaaac gctggtgaaa gtaaaagatg | | | 1260 |
| ctgaagatca gttgggtgca cgagtgggtt acatcgaact ggatctcaac agcggtaaga | | | 1320 |

```
tccttgagag ttttcgcccc gaagaacgtt ttccaatgat gagcactttt aaagttctgc    1380
tatgtggcgc ggtattatcc cgtgttgacg ccgggcaaga gcaactcggt cgccgcatac    1440
actattctca gaatgacttg gttgagtact caccagtcac agaaaagcat cttacggatg    1500
gcatgacagt aagagaatta tgcagtgctg ccataaccat gagtgataac actgcggcca    1560
acttacttct gacaacgatc ggaggaccga aggagctaac cgcttttttg cacaacatgg    1620
gggatcatgt aactcgcctt gatcgttggg aaccggagct gaatgaagcc ataccaaacg    1680
acgagcgtga caccacgatg cctgcagcaa tggcaacaac gttgcgcaaa ctattaactg    1740
gcgaactact tactctagct tcccggcaac aattaataga ctggatggag gcggataaag    1800
ttgcaggacc acttctgcgc tcggcccttc cggctggctg gtttattgct gataaatctg    1860
gagccggtga gcgtgggtct cgcggtatca ttgcagcact ggggccagat ggtaagccct    1920
cccgtatcgt agttatctac acgacgggga gtcaggcaac tatggatgaa cgaaatagac    1980
agatcgctga gataggtgcc tcactgatta agcattggta actgtcagac caagtttact    2040
catatatact ttagattgat ttaaaacttc attttaatt taaaaggatc taggtgaaga    2100
tcctttttga taatctcatg accaaaatcc cttaacgtga gttttcgttc cactgagcgt    2160
cagaccccgt agaaaagatc aaaggatctt cttgagatcc ttttttctg cgcgtaatct    2220 gctgcttgca acaaaaaaa ccaccgctac cagcggtggt ttgtttgccg gatcaagagc    2280
taccaactct ttttccgaag gtaactggct tcagcagagc gcagatacca atactgtcc    2340 ttctagtgta gccgtagtta ggccaccact tcaagaactc tgtagcaccg cctacatacc    2400
tcgctctgct aatcctgtta ccagtggctg ctgccagtgg cgataagtcg tgtcttaccg    2460
ggttggactc aagacgatag ttaccggata aggcgcagcg gtcgggctga acggggggtt    2520
cgtgcacaca gcccagcttg gagcgaacga cctacaccga actgagatac ctacagcgtg    2580
agctatgaga aagcgccacg cttcccgaag ggagaaaggc ggacaggtat ccggtaagcg    2640
gcagggtcgg aacaggagag cgcacagggg agcttccagg gggaaacgcc tggtatcttt    2700
atagtcctgt cgggtttcgc cacctctgac ttgagcgtcg attttgtga tgctcgtcag    2760 gggggcggag cctatggaaa aacgccagca acgcggcctt tttacggttc ctggccttttt    2820 gctggccttt tgctcacatg ttcttcctg cgttatcccc tgattctgtg ataaccgta    2880 ttaccgcctt tgagtgagct gataccgctc gccgcagccg aacgaccgag cgcagcgagt    2940
cagtgagcga ggaagcggaa gagcgcctga tgcggtattt tctccttacg catctgtgcg    3000
gtatttcaca ccgcatatat ggtgcactct cagtacaatc tgctctgatg ccgcatagtt    3060
aagccagtat acactccgct atcgctacgt gactgggtca tggctgcgcc ccgacacccg    3120
ccaacacccg ctgacgcgcc ctgacgggct tgtctgctcc cggcatccgc ttacagacaa    3180
gctgtgaccg tctccgggag ctgcatgtgt cagaggtttt caccgtcatc accgaaacgc    3240
gcgaggcagc tgcggtaaag ctcatcagcg tggtcgtgaa gcgattcaca gatgtctgcc    3300
tgttcatccg cgtccagctc gttgagtttc tccagaagcg ttaatgtctg gcttctgata    3360
aagcgggcca tgttaagggc ggttttttcc tgtttggtca ctgatgcctc cgtgtaaggg    3420
ggatttctgt tcatgggggt aatgataccg atgaaacgag agaggatgct cacgatacgg    3480
gttactgatg atgaacatgc ccggttactg gaacgttgtg agggtaaaca actggcggta    3540
tggatgcggc gggaccagag aaaaatcact cagggtcaat gccagcgctt cgttaataca    3600
gatgtaggtg ttccacaggg tagccagcag catcctgcga tgcagatccg gaacataatg    3660
gtgcagggcg ctgacttccg cgtttccaga ctttacgaaa cacggaaacc gaagaccatt    3720
```

| | |
|---|---|
| catgttgttg ctcaggtcgc agacgttttg cagcagcagt cgcttcacgt tcgctcgcgt | 3780 |
| atcggtgatt cattctgcta accagtaagg caacccccgcc agcctagccg ggtcctcaac | 3840 |
| gacaggagca cgatcatgcg cacccgtggc caggacccaa cgctgcccga tgcgccgc | 3900 |
| gtgcggctgc tggagatggc ggacgcgatg gatatgttct gccaagggtt ggtttgcgca | 3960 |
| ttcacagttc tccgcaagaa ttgattggct ccaattcttg gagtggtgaa tccgttagcg | 4020 |
| aggtgccgcc ggcttccatt caggtcgagg tggcccggct ccatgcaccg cgacgcaacg | 4080 |
| cggggaggca gacaaggtat agggcggcgc ctacaatcca tgccaacccg ttccatgtgc | 4140 |
| tcgccgaggc ggcataaatc gccgtgacga tcagcggtcc agtgatcgaa gttaggctgg | 4200 |
| taagagccgc gagcgatcct tgaagctgtc cctgatggtc gtcatctacc tgcctggaca | 4260 |
| gcatggcctg caacgcgggc atcccgatgc cgccggaagc gagaagaatc ataatgggga | 4320 |
| aggccatcca gcctcgcgtc gcgaacgcca gcaagacgta gcccagcgcg tcggccgcca | 4380 |
| tgccggcgat aatggcctgc ttctcgccga aacgtttggt ggcgggacca gtgacgaagg | 4440 |
| cttgagcgag ggcgtgcaag attccgaata ccgcaagcga caggccgatc atcgtcgcgc | 4500 |
| tccagcgaaa gcggtcctcg ccgaaaatga cccagagcgc tgccggcacc tgtcctacga | 4560 |
| gttgcatgat aaagaagaca gtcataagtg cggcgacgat agtcatgccc cgcgcccacc | 4620 |
| ggaaggagct gactgggttg aaggctctca agggcatcgg tcgatcgacg ctctccctta | 4680 |
| tgcgactcct gcattaggaa gcagcccagt agtaggttga ggccgttgag caccgccgcc | 4740 |
| gcaaggaatg gtgcatgcaa ggagatggcg cccaacagtc ccccggccac ggggcctgcc | 4800 |
| accataccca cgccgaaaca gcgctcatg agcccgaagt ggcgagcccg atcttcccca | 4860 |
| tcggtgatgt cggcgatata ggcgccagca accgcacctg tggcgccggt gatgccggcc | 4920 |
| acgatgcgtc cggcgtagag gatcg | 4945 |

<210> SEQ ID NO 251
<211> LENGTH: 294
<212> TYPE: DNA
<213> ORGANISM: artificial sequence
<220> FEATURE:
<223> OTHER INFORMATION: synthetic construct

<400> SEQUENCE: 251

| | |
|---|---|
| atgtcgtact accatcacca tcaccatcac ctcgaatcaa caagtttgta caaaaaagca | 60 |
| ggctccgcgg ccgccccctt caccggatcc atcgatccac gtttccacga aaactggccg | 120 |
| tctgccggcg gtacctctac ttccaaagct tccaccacta cgacttctag caaaaccacc | 180 |
| actacatcct ctaagactac cacgactacc tccaaaacct ctactacctc tagctcctct | 240 |
| acgggcggcg ccactcacaa gacctctact cagcgtctgc tggctgcata atga | 294 |

<210> SEQ ID NO 252
<211> LENGTH: 128
<212> TYPE: PRT
<213> ORGANISM: artificial sequence
<220> FEATURE:
<223> OTHER INFORMATION: synthetic construct

<400> SEQUENCE: 252

Met His Thr Pro Glu His Ile Thr Ala Val Val Gln Arg Phe Val Ala
1               5                   10                  15

Ala Leu Asn Ala Gly Glu Leu Glu Gly Ile Val Ala Leu Phe Ala Glu
            20                  25                  30

Glu Ala Thr Val Glu Glu Pro Val Gly Ser Glu Pro Arg Ser Gly Thr
        35                  40                  45

Ala Ala Cys Arg Glu Phe Tyr Ala Asn Ser Leu Lys Leu Pro Leu Ala
            50                  55                  60

Val Glu Leu Thr Gln Glu Cys Arg Ala Val Ala Asn Glu Ala Ala Phe
 65                  70                  75                  80

Ala Phe Thr Val Ser Phe Glu Tyr Gln Gly Arg Lys Thr Val Val Ala
                 85                  90                  95

Pro Cys Glu His Phe Arg Phe Asn Gly Ala Gly Lys Val Val Ser Ile
                100                 105                 110

Arg Ala Leu Phe Gly Glu Lys Asn Ile His Ala Cys Gln Gly Ser Asp
            115                 120                 125

<210> SEQ ID NO 253
<211> LENGTH: 129
<212> TYPE: PRT
<213> ORGANISM: artificial sequence
<220> FEATURE:
<223> OTHER INFORMATION: synthetic construct

<400> SEQUENCE: 253

Pro Ser Ala Gln Ser Gln Leu Pro Asp Lys His Ser Gly Leu His Glu
 1               5                  10                  15

Arg Ala Pro Gln Arg Tyr Gly Pro Glu Pro Glu Pro Glu Pro Glu Pro
                20                  25                  30

Ile Pro Glu Pro Pro Lys Glu Ala Pro Val Val Ile Glu Lys Pro Lys
                35                  40                  45

Pro Lys Pro Lys Pro Lys Pro Lys Pro Pro Ala His Asp His Lys Asn
            50                  55                  60

Gln Lys Glu Thr His Gln Arg His Ala Ala Gly Ser Gly Gly Gly Gly
 65                  70                  75                  80

Ser Pro Trp Ala Pro Glu Lys Asp His Met Gln Leu Met Lys Gly Lys
                 85                  90                  95

Gly Lys Gly Lys Gly Lys Gly Lys Gly Lys Gly Lys Gly Lys Gly Lys
                100                 105                 110

Gly Lys Gly Trp Ala Pro Glu Lys Asp His Met Gln Leu Met Lys Gly
            115                 120                 125

Lys

<210> SEQ ID NO 254
<211> LENGTH: 6368
<212> TYPE: DNA
<213> ORGANISM: artificial sequence
<220> FEATURE:
<223> OTHER INFORMATION: synthetic construct

<400> SEQUENCE: 254
agatctcgat cccgcgaaat taatacgact cactataggg agaccacaac ggtttccctc     60
tagaaataat tttgtttaac tttaagaagg agatatacat atgcacactc agaacatat    120 caccgcagta gtacagcgtt ttgtggcagc tctgaacgcg ggcgagctgg aaggtattgt    180
ggcgctgttc gcggaagaag ccaccgtgga agaaccggtg ggttctgaac cgcgttccgg    240
caccgcagcc tgccgtgaat tttacgcaaa cagcctgaag ctgccgctgg cggttgaact    300
gacccaagaa tgtcgtgcgg tggctaacga agccgctttc gcgttcaccg tgtccttcga    360
ataccagggt cgtaagaccg ttgtggcgcc atgcgaacac tttcgtttca acggcgcagg    420
caaagtggtt tccatccgcg cactgttcgg tgaaaagaac atccatgctt gtcagggatc    480
cgatccgact ccgccgacga atgtactgat gctggcaacc aaaggcggtg gtacgcattc    540

-continued

| | |
|---|---|
| cacgcacaac catggcagcc cgcgccacac gaatgctgac gcaggcaatc cgggcggcgg | 600 |
| caccccacca accaatgtcc tgatgctggc tactaaaggc ggcggcacgc attctaccca | 660 |
| caaccatggt agcccgcgcc atactaatgc agatgccggc aacccgggcg gtggtacccc | 720 |
| gccaaccaac gttctgatgc tggcgacgaa aggtggcggt acccattcca cgcataatca | 780 |
| tggcagccct cgccacacca acgctgatgc tggtaatcct ggtggcggta agaagaaata | 840 |
| ataaggcgcg ccgacccagc tttcttgtac aaagtggttg attcgaggct gctaacaaag | 900 |
| cccgaaagga agctgagttg gctgctgcca ccgctgagca ataactagca taaccccttg | 960 |
| gggcctctaa acgggtcttg aggggttttt tgctgaaagg aggaactata tccggatatc | 1020 |
| cacaggacgg gtgtggtcgc catgatcgcg tagtcgatag tggctccaag tagcgaagcg | 1080 |
| agcaggactg ggcggcggcc aaagcggtcg acagtgctc cgagaacggg tgcgcataga | 1140 |
| aattgcatca acgcatatag cgctagcagc acgccatagt gactggcgat gctgtcggaa | 1200 |
| tggacgatat cccgcaagag gcccggcagt accggcataa ccaagcctat gcctacagca | 1260 |
| tccagggtga cggtgccgag gatgacgatg agcgcattgt tagatttcat acacggtgcc | 1320 |
| tgactgcgtt agcaatttaa ctgtgataaa ctaccgcatt aaagcttgca gtggcggttt | 1380 |
| tcatggcttg ttatgactgt ttttttgggg tacagtctat gcctcgggca tccaagcagc | 1440 |
| aagcgcgtta cgccgtgggt cgatgtttga tgttatggag cagcaacgat gttacgcagc | 1500 |
| agggcagtcg ccctaaaaca aagttaaaca tcatgaggga agcggtgatc gccgaagtat | 1560 |
| cgactcaact atcagaggta gttggcgtca tcgagcgcca tctcgaaccg acgttgctgg | 1620 |
| ccgtacattt gtacggctcc gcagtggatg gcggcctgaa gccacacagt gatattgatt | 1680 |
| tgctggttac ggtgaccgta aggcttgatg aaacaacgcg gcgagctttg atcaacgacc | 1740 |
| ttttggaaac ttcggcttcc cctggagaga gcgagattct ccgcgctgta gaagtcacca | 1800 |
| ttgttgtgca cgacgacatc attccgtggc gttatccagc taagcgcgaa ctgcaatttg | 1860 |
| gagaatggca gcgcaatgac attcttgcag gtatcttcga gccagccacg atcgacattg | 1920 |
| atctggctat cttgctgaca aaagcaagag aacatagcgt tgccttggta ggtccagcgg | 1980 |
| cggaggaact ctttgatccg gttcctgaac aggatctatt tgaggcgcta atgaaacct | 2040 |
| taacgctatg gaactcgccg cccgactggg ctggcgatga gcgaaatgta gtgcttacgt | 2100 |
| tgtcccgcat ttggtacagc gcagtaaccg gcaaaatcgc gccgaaggat gtcgctgccg | 2160 |
| actgggcaat ggagcgcctg ccggcccagt atcagcccgt catacttgaa gctagacagg | 2220 |
| cttatcttgg acaagaagaa gatcgcttgg cctcgcgcgc agatcagttg gaagaatttg | 2280 |
| tccactacgt gaaaggcgag atcaccaagg tagtcggcaa ataatgtcta acaattcgtt | 2340 |
| caagcttatc gatgataagc tgtcaaacat gagaattctt gaagacgaaa gggcctcgtg | 2400 |
| atacgcctat ttttataggt taatgtcatg ataataatgg tttcttagac gtcaggtggc | 2460 |
| acttttcggg gaaatgtgcg cggaaccct atttgtttat ttttctaaat acattcaaat | 2520 |
| atgtatccgc tcatgagaca ataaccctga taaatgcttc aataatattg aaaaaggaag | 2580 |
| agtatgagta ttcaacattt ccgtgtcgcc cttattccct ttttgcggc attttgcctt | 2640 |
| cctgttttg ctcacccaga aacgctggtg aaagtaaaag atgctgaaga tcagttgggt | 2700 |
| gcacgagtgg gttacatcga actggatctc aacagcggta agatccttga gttttcgc | 2760 |
| cccgaagaac gttttccaat gatgagcact tttaaagttc tgctatgtgg cgcggtatta | 2820 |
| tcccgtgttg acgccgggca agagcaactc ggtcgccgca tacactattc tcagaatgac | 2880 |
| ttggttgagt actcaccagt cacagaaaag catcttacgg atggcatgac agtaagagaa | 2940 |

```
ttatgcagtg ctgccataac catgagtgat aacactgcgg ccaacttact tctgacaacg    3000
atcggaggac cgaaggagct aaccgctttt ttgcacaaca tggggggatca tgtaactcgc    3060
cttgatcgtt gggaaccgga gctgaatgaa gccataccaa acgacgagcg tgacaccacg    3120
atgcctgcag caatggcaac aacgttgcgc aaactattaa ctggcgaact acttactcta    3180
gcttcccggc aacaattaat agactggatg gaggcggata agttgcagg accacttctg     3240
cgctcggccc ttccggctgg ctggtttatt gctgataaat ctggagccgg tgagcgtggg    3300
tctcgcggta tcattgcagc actggggcca gatggtaagc cctcccgtat cgtagttatc    3360
tacacgacgg ggagtcaggc aactatggat gaacgaaata cagatcgc tgagataggt      3420
gcctcactga ttaagcattg gtaactgtca gaccaagttt actcatatat actttagatt    3480
gatttaaaac ttcattttta atttaaaagg atctaggtga agatccttt tgataatctc     3540
atgaccaaaa tcccttaacg tgagttttcg ttccactgag cgtcagaccc cgtagaaaag    3600
atcaaaggat cttcttgaga tcctttttt ctgcgcgtaa tctgctgctt gcaaacaaaa     3660
aaaccaccgc taccagcggt ggtttgtttg ccggatcaag agctaccaac tcttttttccg   3720
aaggtaactg gcttcagcag agcgcagata ccaaatactg tccttctagt gtagccgtag    3780
ttaggccacc acttcaagaa ctctgtagca ccgcctacat acctcgctct gctaatcctg    3840
ttaccagtgg ctgctgccag tggcgataag tcgtgtctta ccgggttgga ctcaagacga    3900
tagttaccgg ataaggcgca gcggtcgggc tgaacggggg gttcgtgcac acagcccagc    3960
ttggagcgaa cgacctacac cgaactgaga tacctacagc gtgagctatg agaaagcgcc    4020
acgcttcccg aagggagaaa ggcggacagg tatccggtaa gcggcagggt cggaacagga    4080
gagcgcacga gggagcttcc agggggaaac gcctggtatc tttatagtcc tgtcgggttt    4140
cgccacctct gacttgagcg tcgatttttg tgatgctcgt caggggggcg gagcctatgg    4200
aaaaacgcca gcaacgcggc ctttttacgg ttcctggcct tttgctggcc ttttgctcac    4260
atgttctttc ctgcgttatc ccctgattct gtggataacc gtattaccgc ctttgagtga    4320
gctgataccg ctcgccgcag ccgaacgacc gagcgcagcg agtcagtgag cgaggaagcg    4380
gaagagcgcc tgatgcggta ttttctcctt acgcatctgt gcggtatttc acaccgcata    4440
tatggtgcac tctcagtaca atctgctctg atgccgcata gttaagccag tatacactcc    4500
gctatcgcta cgtgactggg tcatggctgc gccccgacac ccgccaacac ccgctgacgc    4560
gccctgacgg gcttgtctgc tcccggcatc cgcttacaga caagctgtga ccgtctccgg    4620
gagctgcatg tgtcagaggt tttcaccgtc atcaccgaaa cgcgcgaggc agctgcggta    4680
aagctcatca gcgtggtcgt gaagcgattc acagatgtct gcctgttcat ccgcgtccag    4740
ctcgttgagt ttctccagaa gcgttaatgt ctggcttctg ataaagcggg ccatgttaag    4800
ggcggttttt tcctgtttgg tcactgatgc ctccgtgtaa gggggatttc tgttcatggg    4860
ggtaatgata ccgatgaaac gagagaggat gctcacgata cgggttactg atgatgaaca    4920
tgcccggtta ctggaacgtt gtgagggtaa acaactggcg gtatggatgc ggcgggacca    4980
gagaaaaatc actcagggtc aatgccagcg cttcgttaat acagatgtag gtgttccaca    5040
gggtagccag cagcatcctg cgatgcagat ccggaacata atggtgcagg cgctgactt     5100
ccgcgtttcc agactttacg aaacacgaa accgaagacc attcatgttg ttgctcaggt     5160
cgcagacgtt ttgcagcagc agtcgcttca cgttcgctcg cgtatcggtg attcattctg    5220
ctaaccagta aggcaacccc gccagcctag ccgggtcctc aacgacagga gcacgatcat    5280
gcgcacccgt ggccaggacc caacgctgcc cgagatgcgc cgcgtgcggc tgctggagat    5340
```

| | | |
|---|---|---|
| ggcggacgcg atggatatgt tctgccaagg gttggtttgc gcattcacag ttctccgcaa | 5400 | |
| gaattgattg gctccaattc ttggagtggt gaatccgtta gcgaggtgcc gccggcttcc | 5460 | |
| attcaggtcg aggtggcccg gctccatgca ccgcgacgca acgcggggag gcagacaagg | 5520 | |
| tatagggcgg cgcctacaat ccatgccaac ccgttccatg tgctcgccga ggcggcataa | 5580 | |
| atcgccgtga cgatcagcgg tccagtgatc gaagttaggc tggtaagagc cgcgagcgat | 5640 | |
| ccttgaagct gtccctgatg gtcgtcatct acctgcctgg acagcatggc ctgcaacgcg | 5700 | |
| ggcatcccga tgccgccgga agcgagaaga atcataatgg ggaaggccat ccagcctcgc | 5760 | |
| gtcgcgaacg ccagcaagac gtagcccagc gcgtcggccg ccatgccggc gataatggcc | 5820 | |
| tgcttctcgc cgaaacgttt ggtggcggga ccagtgacga aggcttgagc gagggcgtgc | 5880 | |
| aagattccga ataccgcaag cgacaggccg atcatcgtcg cgctccagcg aaagcggtcc | 5940 | |
| tcgccgaaaa tgacccagag cgctgccggc acctgtccta cgagttgcat gataaagaag | 6000 | |
| acagtcataa gtcggcgac gatagtcatg ccccgcgccc accggaagga gctgactggg | 6060 | |
| ttgaaggctc tcaagggcat cggtcgatcg acgctctccc ttatgcgact cctgcattag | 6120 | |
| gaagcagccc agtagtaggt tgaggccgtt gagcaccgcc gccgcaagga atggtgcatg | 6180 | |
| caaggagatg gcgcccaaca gtcccccggc cacggggcct gccaccatac ccacgccgaa | 6240 | |
| acaagcgctc atgagcccga agtggcgagc ccgatcttcc ccatcggtga tgtcggcgat | 6300 | |
| ataggcgcca gcaaccgcac ctgtggcgcc ggtgatgccg ccacgatgc gtccggcgta | 6360 | |
| gaggatcg | 6368 | |

```
<210> SEQ ID NO 255
<211> LENGTH: 777
<212> TYPE: DNA
<213> ORGANISM: artificial sequence
<220> FEATURE:
<223> OTHER INFORMATION: synthetic construct

<400> SEQUENCE: 255
```

| | | |
|---|---|---|
| atgcacactc cagaacatat caccgcagta gtacagcgtt ttgtggcagc tctgaacgcg | 60 | |
| ggcgagctgg aaggtattgt ggcgctgttc gcggaagaag ccaccgtgga agaaccggtg | 120 | |
| ggttctgaac cgcgttccgg caccgcagcc tgccgtgaat tttacgcaaa cagcctgaag | 180 | |
| ctgccgctgg cggttgaact gacccaagaa tgtcgtgcgg tggctaacga agccgctttc | 240 | |
| gcgttcaccg tgtccttcga ataccagggt cgtaagaccg ttgtggcgcc atgcgaacac | 300 | |
| tttcgtttca cggcgcagg caaagtggtt tccatccgcg cactgttcgg tgaaaagaac | 360 | |
| atccatgctt gtcagggatc cgatccttct gctcaatctc aactgcctga taaacattct | 420 | |
| ggtctgcacg agcgcgctcc gcagcgctat ggccctgaac cggaacctga gccagagccg | 480 | |
| attccggaac cgccgaaaga ggcgccagta gttatcgaaa acctaaaccc aaaaccaaaa | 540 | |
| ccgaaaccga aacctccggc ccacgaccac aaaaaccaga agaaacccca tcagcgtcac | 600 | |
| gccgctggtt ctggtggtgg cggtagcccg tgggctccgg aaaaggatca catgcagctg | 660 | |
| atgaaaggca aagtaaggg caaaggtaaa ggtaagggta aagcaaagg caaaggcaag | 720 | |
| ggcaagggtt gggcaccaga gaaagaccac atgcaactga tgaagggtaa ataatga | 777 | |

```
<210> SEQ ID NO 256
<211> LENGTH: 257
<212> TYPE: PRT
<213> ORGANISM: artificial sequence
<220> FEATURE:
<223> OTHER INFORMATION: synthetic construct
```

<400> SEQUENCE: 256

```
Met His Thr Pro Glu His Ile Thr Ala Val Val Gln Arg Phe Val Ala
1               5                   10                  15

Ala Leu Asn Ala Gly Glu Leu Glu Gly Ile Val Ala Leu Phe Ala Glu
            20                  25                  30

Glu Ala Thr Val Glu Glu Pro Val Gly Ser Glu Pro Arg Ser Gly Thr
        35                  40                  45

Ala Ala Cys Arg Glu Phe Tyr Ala Asn Ser Leu Lys Leu Pro Leu Ala
    50                  55                  60

Val Glu Leu Thr Gln Glu Cys Arg Ala Val Ala Asn Glu Ala Ala Phe
65                  70                  75                  80

Ala Phe Thr Val Ser Phe Glu Tyr Gln Gly Arg Lys Thr Val Val Ala
                85                  90                  95

Pro Cys Glu His Phe Arg Phe Asn Gly Ala Gly Lys Val Val Ser Ile
            100                 105                 110

Arg Ala Leu Phe Gly Glu Lys Asn Ile His Ala Cys Gln Gly Ser Asp
        115                 120                 125

Pro Ser Ala Gln Ser Gln Leu Pro Asp Lys His Ser Gly Leu His Glu
    130                 135                 140

Arg Ala Pro Gln Arg Tyr Gly Pro Glu Pro Glu Pro Glu Pro Glu Pro
145                 150                 155                 160

Ile Pro Glu Pro Pro Lys Glu Ala Pro Val Val Ile Glu Lys Pro Lys
                165                 170                 175

Pro Lys Pro Lys Pro Lys Pro Lys Pro Ala His Asp His Lys Asn
            180                 185                 190

Gln Lys Glu Thr His Gln Arg His Ala Ala Gly Ser Gly Gly Gly Gly
        195                 200                 205

Ser Pro Trp Ala Pro Glu Lys Asp His Met Gln Leu Met Lys Gly Lys
    210                 215                 220

Gly Lys Gly Lys Gly Lys Gly Lys Gly Lys Gly Lys Gly Lys Gly Lys
225                 230                 235                 240

Gly Lys Gly Trp Ala Pro Glu Lys Asp His Met Gln Leu Met Lys Gly
                245                 250                 255

Lys
```

<210> SEQ ID NO 257
<211> LENGTH: 53
<212> TYPE: DNA
<213> ORGANISM: artificial sequence
<220> FEATURE:
<223> OTHER INFORMATION: primer

<400> SEQUENCE: 257
gcttgtcagg gatccgatcc tgaccctgat ccatctgctc aatctcaact gcc      53

<210> SEQ ID NO 258
<211> LENGTH: 53
<212> TYPE: DNA
<213> ORGANISM: artificial sequence
<220> FEATURE:
<223> OTHER INFORMATION: primer

<400> SEQUENCE: 258
ggcagttgag attgagcaga tggatcaggg tcaggatcgg atccctgaca agc      53

<210> SEQ ID NO 259
<211> LENGTH: 789
<212> TYPE: DNA

-continued

<213> ORGANISM: artificial sequence
<220> FEATURE:
<223> OTHER INFORMATION: synthetic construct

<400> SEQUENCE: 259

```
atgcacactc cagaacatat caccgcagta gtacagcgtt ttgtggcagc tctgaacgcg      60
ggcgagctgg aaggtattgt ggcgctgttc gcggaagaag ccaccgtgga agaaccggtg     120
ggttctgaac cgcgttccgg caccgcagcc tgccgtgaat tttacgcaaa cagcctgaag     180
ctgccgctgg cggttgaact gacccaagaa tgtcgtgcgg tggctaacga agccgctttc     240
gcgttcaccg tgtccttcga ataccagggt cgtaagaccg ttgtggcgcc atgcgaacac     300
tttcgtttca acggcgcagg caaagtggtt tccatccgcg cactgttcgg tgaaaagaac     360
atccatgctt gtcagggatc cgatcctgac cctgatccat ctgctcaatc tcaactgcct     420
gataaacatt ctggtctgca cgagcgcgct ccgcagcgct atggccctga accggaacct     480
gagccagagc cgattccgga accgccgaaa gaggcgccag tagttatcga aaaacctaaa     540
ccaaaaccaa aaccgaaacc gaaacctccg gcccacgacc acaaaaacca gaaagaaacc     600
catcagcgtc acgccgctgg ttctggtggt ggcggtagcc cgtgggctcc ggaaaaggat     660
cacatgcagc tgatgaaagg caaaggtaag ggcaaaggta aggtaaggg taaaggcaaa     720
ggcaaaggca agggcaaggg ttgggcacca gagaaagacc acatgcaact gatgaagggt     780
aaataatga                                                            789
```

<210> SEQ ID NO 260
<211> LENGTH: 261
<212> TYPE: PRT
<213> ORGANISM: artificial sequence
<220> FEATURE:
<223> OTHER INFORMATION: synthetic construct

<400> SEQUENCE: 260

```
Met His Thr Pro Glu His Ile Thr Ala Val Val Gln Arg Phe Val Ala
1               5                   10                  15

Ala Leu Asn Ala Gly Glu Leu Glu Gly Ile Val Ala Leu Phe Ala Glu
            20                  25                  30

Glu Ala Thr Val Glu Glu Pro Val Gly Ser Glu Pro Arg Ser Gly Thr
        35                  40                  45

Ala Ala Cys Arg Glu Phe Tyr Ala Asn Ser Leu Lys Leu Pro Leu Ala
    50                  55                  60

Val Glu Leu Thr Gln Glu Cys Arg Ala Val Ala Asn Glu Ala Ala Phe
65                  70                  75                  80

Ala Phe Thr Val Ser Phe Glu Tyr Gln Gly Arg Lys Thr Val Val Ala
                85                  90                  95

Pro Cys Glu His Phe Arg Phe Asn Gly Ala Gly Lys Val Val Ser Ile
            100                 105                 110

Arg Ala Leu Phe Gly Glu Lys Asn Ile His Ala Cys Gln Gly Ser Asp
        115                 120                 125

Pro Asp Pro Asp Pro Ser Ala Gln Ser Gln Leu Pro Asp Lys His Ser
    130                 135                 140

Gly Leu His Glu Arg Ala Pro Gln Arg Tyr Gly Pro Glu Pro Glu Pro
145                 150                 155                 160

Glu Pro Glu Pro Ile Pro Glu Pro Lys Glu Ala Pro Val Val Ile
                165                 170                 175

Glu Lys Pro Lys Pro Lys Pro Lys Pro Lys Pro Lys Pro Pro Ala His
            180                 185                 190
```

```
Asp His Lys Asn Gln Lys Glu Thr His Gln Arg His Ala Ala Gly Ser
        195                 200                 205

Gly Gly Gly Gly Ser Pro Trp Ala Pro Glu Lys Asp His Met Gln Leu
    210                 215                 220

Met Lys Gly Lys Gly Lys Gly Lys Gly Lys Gly Lys Gly Lys Gly Lys
225                 230                 235                 240

Gly Lys Gly Lys Gly Lys Gly Trp Ala Pro Glu Lys Asp His Met Gln
            245                 250                 255

Leu Met Lys Gly Lys
        260
```

```
<210> SEQ ID NO 261
<211> LENGTH: 48
<212> TYPE: DNA
<213> ORGANISM: artificial sequence
<220> FEATURE:
<223> OTHER INFORMATION: primer

<400> SEQUENCE: 261
gatccgatcc tgaccctcca gatccaccgt ctgctcaatc tcaactgc            48

<210> SEQ ID NO 262
<211> LENGTH: 48
<212> TYPE: DNA
<213> ORGANISM: artificial sequence
<220> FEATURE:
<223> OTHER INFORMATION: primer

<400> SEQUENCE: 262
gcagttgaga ttgagcagac ggtggatctg gagggtcagg atcggatc             48

<210> SEQ ID NO 263
<211> LENGTH: 795
<212> TYPE: DNA
<213> ORGANISM: artificial sequence
<220> FEATURE:
<223> OTHER INFORMATION: synthetic construct

<400> SEQUENCE: 263
atgcacactc cagaacatat caccgcagta gtacagcgtt ttgtggcagc tctgaacgcg      60
ggcgagctgg aaggtattgt ggcgctgttc gcggaagaag ccaccgtgga agaaccggtg     120
ggttctgaac gcgttccgg caccgcagcc tgccgtgaat tttacgcaaa cagcctgaag      180
ctgccgctgg cggttgaact gacccaagaa tgtcgtgcgg tggctaacga agccgctttc     240
gcgttcaccg tgtccttcga ataccagggt cgtaagaccg ttgtggcgcc atgcgaacac     300
tttcgtttca cggcgcagg caaagtggtt ccatccgcg cactgttcgg tgaaaagaac       360
atccatgctt gtcagggatc cgatcctgac cctccagatc accgtctgc tcaatctcaa     420 ctgcctgata acattctgg tctgcacgag cgcgctccgc agcgctatgg ccctgaaccg     480
gaacctgagc cagagccgat ccggaaccg ccgaaagagg cgccagtagt tatcgaaaaa     540
cctaaaccaa aaccaaaacc gaaaccgaaa cctccggccc acgaccacaa aaaccagaaa     600
gaaacccatc agcgtcacgc cgctggttct ggtggtggcg gtagcccgtg gctccggaa     660 aaggatcaca tgcagctgat gaaaggcaaa ggtaagggca aggtaaagg taagggtaaa     720 ggcaaaggca aggcaaggg caagggttgg gcaccagaga agaccacat gcaactgatg     780 aagggtaaat aatga                                                     795

<210> SEQ ID NO 264
<211> LENGTH: 263
```

```
<212> TYPE: PRT
<213> ORGANISM: artificial sequence
<220> FEATURE:
<223> OTHER INFORMATION: synthetic construct

<400> SEQUENCE: 264
```

| | | | | | | | | | | | | | | | |
|---|---|---|---|---|---|---|---|---|---|---|---|---|---|---|---|
| Met | His | Thr | Pro | Glu | His | Ile | Thr | Ala | Val | Val | Gln | Arg | Phe | Val | Ala |
| 1 | | | | 5 | | | | | 10 | | | | | 15 | |
| Ala | Leu | Asn | Ala | Gly | Glu | Leu | Glu | Gly | Ile | Val | Ala | Leu | Phe | Ala | Glu |
| | | | 20 | | | | | 25 | | | | | 30 | | |
| Glu | Ala | Thr | Val | Glu | Glu | Pro | Val | Gly | Ser | Glu | Pro | Arg | Ser | Gly | Thr |
| | | | 35 | | | | 40 | | | | | 45 | | | |
| Ala | Ala | Cys | Arg | Glu | Phe | Tyr | Ala | Asn | Ser | Leu | Lys | Leu | Pro | Leu | Ala |
| | 50 | | | | | 55 | | | | | 60 | | | | |
| Val | Glu | Leu | Thr | Gln | Glu | Cys | Arg | Ala | Val | Ala | Asn | Glu | Ala | Ala | Phe |
| 65 | | | | | 70 | | | | | 75 | | | | | 80 |
| Ala | Phe | Thr | Val | Ser | Phe | Glu | Tyr | Gln | Gly | Arg | Lys | Thr | Val | Val | Ala |
| | | | | 85 | | | | | 90 | | | | | 95 | |
| Pro | Cys | Glu | His | Phe | Arg | Phe | Asn | Gly | Ala | Gly | Lys | Val | Val | Ser | Ile |
| | | | 100 | | | | | 105 | | | | | 110 | | |
| Arg | Ala | Leu | Phe | Gly | Glu | Lys | Asn | Ile | His | Ala | Cys | Gln | Gly | Ser | Asp |
| | | | 115 | | | | | 120 | | | | | 125 | | |
| Pro | Asp | Pro | Pro | Asp | Pro | Pro | Ser | Ala | Gln | Ser | Gln | Leu | Pro | Asp | Lys |
| | 130 | | | | | 135 | | | | | 140 | | | | |
| His | Ser | Gly | Leu | His | Glu | Arg | Ala | Pro | Gln | Arg | Tyr | Gly | Pro | Glu | Pro |
| 145 | | | | | 150 | | | | | 155 | | | | | 160 |
| Glu | Pro | Glu | Pro | Glu | Pro | Ile | Pro | Glu | Pro | Pro | Lys | Glu | Ala | Pro | Val |
| | | | | 165 | | | | | 170 | | | | | 175 | |
| Val | Ile | Glu | Lys | Pro | Lys | Pro | Lys | Pro | Lys | Pro | Lys | Pro | Lys | Pro | Pro |
| | | | | 180 | | | | | 185 | | | | | 190 | |
| Ala | His | Asp | His | Lys | Asn | Gln | Lys | Glu | Thr | His | Gln | Arg | His | Ala | Ala |
| | | | 195 | | | | | 200 | | | | | 205 | | |
| Gly | Ser | Gly | Gly | Gly | Gly | Ser | Pro | Trp | Ala | Pro | Glu | Lys | Asp | His | Met |
| | 210 | | | | | 215 | | | | | 220 | | | | |
| Gln | Leu | Met | Lys | Gly | Lys | Gly | Lys | Gly | Lys | Gly | Lys | Gly | Lys | Gly | Lys |
| 225 | | | | | 230 | | | | | 235 | | | | | 240 |
| Gly | Lys | Gly | Lys | Gly | Lys | Gly | Lys | Gly | Trp | Ala | Pro | Glu | Lys | Asp | His |
| | | | | 245 | | | | | 250 | | | | | 255 | |
| Met | Gln | Leu | Met | Lys | Gly | Lys | | | | | | | | | |
| | | | | 260 | | | | | | | | | | | |

```
<210> SEQ ID NO 265
<211> LENGTH: 46
<212> TYPE: DNA
<213> ORGANISM: artificial sequence
<220> FEATURE:
<223> OTHER INFORMATION: primer

<400> SEQUENCE: 265
gtcagggatc cgatcctcca gaccctccag atccatctgc tcaatc           46

<210> SEQ ID NO 266
<211> LENGTH: 46
<212> TYPE: DNA
<213> ORGANISM: artificial sequence
<220> FEATURE:
<223> OTHER INFORMATION: primer

<400> SEQUENCE: 266
```
gattgagcag atggatctgg agggtctgga ggatcggatc cctgac                46

<210> SEQ ID NO 267
<211> LENGTH: 795
<212> TYPE: DNA
<213> ORGANISM: artificial sequence
<220> FEATURE:
<223> OTHER INFORMATION: synthetic construct

<400> SEQUENCE: 267

```
atgcacactc cagaacatat caccgcagta gtacagcgtt ttgtggcagc tctgaacgcg      60
ggcgagctgg aaggtattgt ggcgctgttc gcggaagaag ccaccgtgga agaaccggtg     120
ggttctgaac cgcgttccgg caccgcagcc tgccgtgaat tttacgcaaa cagcctgaag     180
ctgccgctgg cggttgaact gacccaagaa tgtcgtgcgg tggctaacga agccgctttc    240
gcgttcaccg tgtccttcga ataccagggt cgtaagaccg ttgtggcgcc atgcgaacac    300
tttcgtttca cggcgcagg caaagtggtt tccatccgcg cactgttcgg tgaaaagaac    360
atccatgctt gtcagggatc cgatcctcca gaccctccag atccatctgc tcaatctcaa    420
ctgcctgata acattctggg tctgcacgag cgcgctccgc agcgctatgg ccctgaaccg    480
gaacctgagc cagagccgat tccggaaccg ccgaaagagg cgccagtagt tatcgaaaaa    540
cctaaaccaa aaccaaaacc gaaaccgaaa cctccggccc acgaccacaa aaaccagaaa    600
gaaacccatc agcgtcacgc cgctggttct ggtggtggcg gtagcccgtg ggctccggaa    660
aaggatcaca tgcagctgat gaaaggcaaa ggtaagggca aggtaaagg taagggtaaa    720
ggcaaaggca aggcaaggg caagggttgg gcaccagaga aagaccacat gcaactgatg    780
aagggtaaat aatga                                                    795
```

<210> SEQ ID NO 268
<211> LENGTH: 263
<212> TYPE: PRT
<213> ORGANISM: artificial sequence
<220> FEATURE:
<223> OTHER INFORMATION: synthetic construct

<400> SEQUENCE: 268

```
Met His Thr Pro Glu His Ile Thr Ala Val Val Gln Arg Phe Val Ala
1               5                   10                  15
Ala Leu Asn Ala Gly Glu Leu Glu Gly Ile Val Ala Leu Phe Ala Glu
            20                  25                  30
Glu Ala Thr Val Glu Glu Pro Val Gly Ser Glu Pro Arg Ser Gly Thr
        35                  40                  45
Ala Ala Cys Arg Glu Phe Tyr Ala Asn Ser Leu Lys Leu Pro Leu Ala
    50                  55                  60
Val Glu Leu Thr Gln Glu Cys Arg Ala Val Ala Asn Glu Ala Ala Phe
65                  70                  75                  80
Ala Phe Thr Val Ser Phe Glu Tyr Gln Gly Arg Lys Thr Val Val Ala
                85                  90                  95
Pro Cys Glu His Phe Arg Phe Asn Gly Ala Gly Lys Val Val Ser Ile
            100                 105                 110
Arg Ala Leu Phe Gly Glu Lys Asn Ile His Ala Cys Gln Gly Ser Asp
        115                 120                 125
Pro Pro Asp Pro Pro Asp Pro Ser Ala Gln Ser Gln Leu Pro Asp Lys
    130                 135                 140
His Ser Gly Leu His Glu Arg Ala Pro Gln Arg Tyr Gly Pro Glu Pro
145                 150                 155                 160
```

-continued

```
Glu Pro Glu Pro Glu Pro Ile Pro Glu Pro Pro Lys Glu Ala Pro Val
            165             170                 175
Val Ile Glu Lys Pro Lys Pro Lys Pro Lys Pro Lys Pro Lys Pro Pro
            180             185                 190
Ala His Asp His Lys Asn Gln Lys Glu Thr His Gln Arg His Ala Ala
            195             200                 205
Gly Ser Gly Gly Gly Ser Pro Trp Ala Pro Glu Lys Asp His Met
        210             215             220
Gln Leu Met Lys Gly Lys Gly Lys Gly Lys Gly Lys Gly Lys Gly Lys
225             230             235                 240
Gly Lys Gly Lys Gly Lys Gly Lys Trp Ala Pro Glu Lys Asp His
            245             250                 255
Met Gln Leu Met Lys Gly Lys
            260
```